US008980861B2

(12) United States Patent
Salogiannis et al.

(10) Patent No.: US 8,980,861 B2
(45) Date of Patent: Mar. 17, 2015

(54) METHOD FOR DETERMINING ACTIVATORS OF EXCITATORY SYNAPSE FORMATION

(75) Inventors: John Salogiannis, Jamaica Plain, MA (US); Michael E. Greenberg, Brookline, MA (US); Seth S. Margolis, Towson, MD (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/881,910

(22) PCT Filed: Oct. 25, 2011

(86) PCT No.: PCT/US2011/057639
§ 371 (c)(1),
(2), (4) Date: Jul. 3, 2013

(87) PCT Pub. No.: WO2012/058201
PCT Pub. Date: May 3, 2012

(65) Prior Publication Data
US 2013/0273076 A1    Oct. 17, 2013

Related U.S. Application Data

(60) Provisional application No. 61/406,757, filed on Oct. 26, 2010.

(51) Int. Cl.
*C12N 15/11*    (2006.01)
*G01N 33/50*    (2006.01)

(52) U.S. Cl.
CPC ........ *G01N 33/5058* (2013.01); *G01N 2500/00* (2013.01)
USPC ..................................................... 514/44 A

(58) Field of Classification Search
USPC ..................................................... 514/44 A
See application file for complete search history.

(56) References Cited

U.S. PATENT DOCUMENTS

| 2003/0027147 A1 | 2/2003 | Worley et al. |
| 2007/0042948 A1 | 2/2007 | Forstner et al. |
| 2010/0242126 A1 | 9/2010 | Iwasato et al. |

OTHER PUBLICATIONS

Fellman et al., Mol. Cell 2011, 41:733-746.*
Xia et al., The Journal of Neuroscience, 16(17):5425-5436 (1996). "Calcium Influx via the NMDA Receptor Induces Immediate Early Gene Transcription by a MAP Kinase/ERK-Dependent Mechanism."
Yashiro et al., Nature Neuroscience, 12(6):777-783 (2009). "Ube3a is required for experience-dependent maturation of the neocortex."
Yen et al., Science, 322:918-923 (2008). "Global Protein Stability Profiling in Mammalian Cells."
Ziv et al., Neuron, 17:91-102 (1996). "Evidence for a Role of Dendritic Filopodia in Synaptogenesis and Spine Formation."
Aoto and Chen, "Bidirectional ephrin/Eph signaling in synaptic functions" Brain Research 1184:72-80 (2006).
Margolis et al., "EphB-mediated degradation of the RhoA GEF ephexin5 relieves a developmental brake on excitatory synapse formation" Cell 143(3):442-455 (2010).
Aghazadeh et al., Cell, 102:625-633 (2000). "Structural Basis for Relief of Autoinhibition of the Dbl Homology Domain of Proto-Oncogene Vav by Tyrosine Phosphorylation."
Calo et al., Journal of Neurochemistry, 98:1-10 (2006). "Interaction between ephrins/Eph receptors and excitatory amino acid receptors: possible relevance in the regulation of synaptic plasticity and in the pathophysiology of neuronal degeneration."
Contractor et al., Science, 296:1864-1869 (2002). "Trans-Synaptic Eph Receptor-Ephrin Signaling in Hippocampal Mossy Fiber LTP."
Cooper et al., The Journal of Biological Chemistry, 279(39):41208-41217 (2004). "Biochemical Analysis of Angelman Syndrome-associated Mutations in the E3 Ubiquitin Ligase E6-associated Protein."
Cowan et al., Neuron, 46:205-217 (2005). "Vav Family GEFs Link Activated Ephs to Endocytosis and Axon Guidance."
Dalva et al., Cell, 103:945-956 (2000). "EphB Receptors Interact with NMDA Receptors and Regulate Excitatory Synapse Formation."
Dalva et al., Nature, 8:206-220 (2007). "Cell adhesion molecules: signalling functions at the synapse."
Dindot et al., Human Molecular Genetics, 17(1):111-118 (2008). "The Angelman syndrome ubiquitin ligase localizes to the synapse and nucleus, and maternal deficiency results in abnormal dendritic spine mophology."
Egea et al., Trends in Cell Biology, 17(5):230-238 (2007). "Bidirectional Eph-ephrin signaling during axon guidance."
Ethell et al., Neuron, 31:1001-1013 (2001). "EphB/Syndecan-2 Signaling in Dendritic Spine Morphogenesis."
Fasen et al., Traffic, 9:251-266 (2008). "Ligand Binding Induces Cbl-Dependent EphB1 Receptor Degradation Through the Lysosomal Pathway."
Flanagan et al., Annu. Rev. Neurosc., 21:309-345 (1998). "The Ephrins and Eph Receptors in Neural Development."
Flavell et al., Science, 311:1008-1012 (2006). "Activity-Dependent Regulation of MEF2 Transcription Factors Suppresses Excitatory Synapse Number."
Fu et al., Nature Neuroscience, 10(1):67-76 (2007). "Cdk5 regulates EphA4-mediated dendritic spine retraction through an ephexin1-dependent mechanism."
Glessner et al., Nature, 459:569-573 (2009). "Autism genome-wide copy of number variation reveals ubiquitin and neuronal genes."
Greer et al., Neuron, 59:846-860 (2008). "From Synapse to Nucleus: Calcium-Dependent Gene Transcription in the Control of Synapse Development and Function."
Greer et al., Cell, 140:704-716 (2010). "The Angelman Syndrome Protein Ube3A Regulates Synapse Development by Ubiquitinating Arc."
Grunwald et al., Neuron, 32:1027-1040 (2001). "Kinase-Independant Requirement of EphB2 Receptors in Hippocampal Synaptic Plasticity."

(Continued)

*Primary Examiner* — Brian Whiteman
(74) *Attorney, Agent, or Firm* — Nixon Peabody LLP

(57) ABSTRACT

The invention provides methods of screening a compound that can increase spine/excitatory synapse formation and/or numbers. The compound is identified by contacting Ephexin5 with a test compound and selecting the compounds that inhibit Rho GEF activity of Ephexin5. Additionally, the invention also provides methods for increasing spine/excitatory synapse formation and/or numbers by contacting a neuron with an Ephexin5 inhibitor.

5 Claims, 33 Drawing Sheets

(56) References Cited

OTHER PUBLICATIONS

Grunwald et al., Nature Neuroscience, 7(1):33-40 (2004). "Hippocampal plasticity requires postsynaptic ephrinBs."

Henkemeyer et al., The Journal of Cell Biology, 163(6):1313-1326 (2003). "Multiple EphB receptor tyrosine kinases shape dendritic spines in the hippocampus."

Hershko et al., Annu. Rev. Biochem., 67:425-479 (1998). "The Ubiquitin System."

Jiang et al., Neuron, 21:799-811 (1998). "Mutation of the Angelman Ubiquitin Ligase in Mice Causes Increased Cytoplasmic p53 and Deficits of Contextual Learning and Long Term Potential."

Jontes et al., Nature Neuroscience, 3(3):231-237 (2000). "Growth cone and dendrite dynamics in zebrafish embryos: early events in synaptogenesis imaged."

Kayser et al., The Journal of Neuroscience, 26(47):12152-12164 (2006). "Intracellular and Trans-Synaptic Regulation of Glutamatergic Synaptogenesis by EphB Receptors."

Kayser et al., Neuron, 59:56-59 (2008). "EphB Receptors Couple Dendritic Filopodia Motility to Synapse Formation."

Kishino, et al., Nature Genetics, 15:70-73 (1997). "UBE3A/E6-AP mutations cause Angelman syndrome."

Klein, Nature Neuroscience, 12(1):15-20 (2009). "Bidirectional modulation of synaptic functions by Eph/ephrin signaling."

Kopec et al., The Journal of Neuroscience, 26(7):2000-2009 (2006). "Glutamate Receptor Exocytosis and Spine Enlargement during Chemically Induced Long-Term Potentiation."

Lai et al., Current Opinion in Neurobiology, 19:275-283 (2009). "Synapse development and plasticity: roles of ephrin/Eph receptor signaling."

Lim et al., Nature, 11(2):160-169 (2008). "Ephrin-B reverse signaling promotes structural and functional synaptic maturation in vivo."

Lin et al., Nature, 455:1198-1203 (2008). "Activity-dependent regulation of inhibitory synapse development by Npas4."

Lois et al., Science, 295:868-872 (2002). "Germline Transmission and Tissue-Specific Expression of Transgenes Delivered by Lentiviral Vectors."

Matsuzaki et al., Nature, 429:761-766 (2004). "Structural basis of long-term potentiation in single dendritic spines."

Micheva et al., Neuron, 55:25-36 (2007). "Array Tomography: A New Tool for Imaging the Molecular Architecture and Ultrastructure of Neural Circuits."

Murai et al., Nature Neuroscience, 6(2):153-160 (2003). "Control of hippocampal dendritic spine morphology through ephrin-A3/EphA4 signaling."

Ogita et al., Circ Res., 93:23-31 (2003). "EphA4-Mediated Rho Activation via Vsm-RhoGEF Expressed Specifically in Vascular Smooth Muscle Cells."

Pak et al., Neuron, 31:289-303 (2001). "Regulation of Dendritic Spine Morphology by SPAR, a PSD-95-Associated RapGAP."

Paradis et al., Neuron, 53:217-232 (2007). "An RNAi-Based Approach Identifies Molecules Required for Glutamatergic and GABAergic Synapse Development."

Penzes et al., Neuron, 37:263-274 (2003). "Rapid Induction of Dendritic Spine Morphogenesis by trans-Synaptic EphrinB-EphB Receptor Activation of the Rho-GEF Kalirin."

Rossman et al., Nature Reviews Molecular Cell Biology, 6:167-180 (2005). "GEF Means Go: Turning on RHO GTPases with Guanine Nucleotide-Exchange Factors."

Sahin et al., Neuron, 46:191-204 (2005). "Eph-Dependent Tyrosine Phosphorylation of Ephexin1 Modulates Growth Cone Collapse."

Schaeren-Wiemers et al., Histochemistry, 100:431-440 (1993). "A single protocol to detect transcripts of various types and expression levels in neural tissue and cultured cells: in situ hybridization using digoxigenin-labelled cRNA probes."

Shaman et al., Cell, 105:233-244 (2001). "EphA Receptors Regulate Growth Cone Dynamics through the Novel Guanine Nucleotide Exchange Factor Ephexin."

Sharfe et al., The Journal of Immunology, 170:6024-6032 (2003). "Ephrin-A1 Induces a c-Cbl Phosphorylation and EphA Receptor Down-Regulation in T Cells."

Snyder et al., Nature Structural Biology, 9(6):468-475 (2002). "Structural basis for the selective activation of Rho GTPases by Dbl exchange factors."

Stoppini et al., Journal of Neuroscience Methods, 37:173-182 (1991). "A simple method for organotypic cultures of nervous tissue."

Takasu et al., Science, 295:491-495 (2002). "Modulation of NMDA Receptor-Dependent Calcium Influx and Gene Expression Through EphB Receptors."

Tashiro et al., Cerebral Cortex, 10:927-938 (2000). "Regulation of Dendritic Spine Morphology by the Rho Family of Small GTPases: Antagonistic Roles of Rac and Rho."

Tolias et al., Neuron, 45:525-538 (2005). "The Rac1-GEF Tiam1 Couples the NMDA Receptor to the Activity-Dependent Development of Dendritic Arbors and Spines."

Tolias et al., PNAS, 104(17):7265-7270 (2007). "The Rac1 guanine nucleotide exchange factor Tiam1 mediates the EphB receptor-dependent dendritic spine development."

* cited by examiner

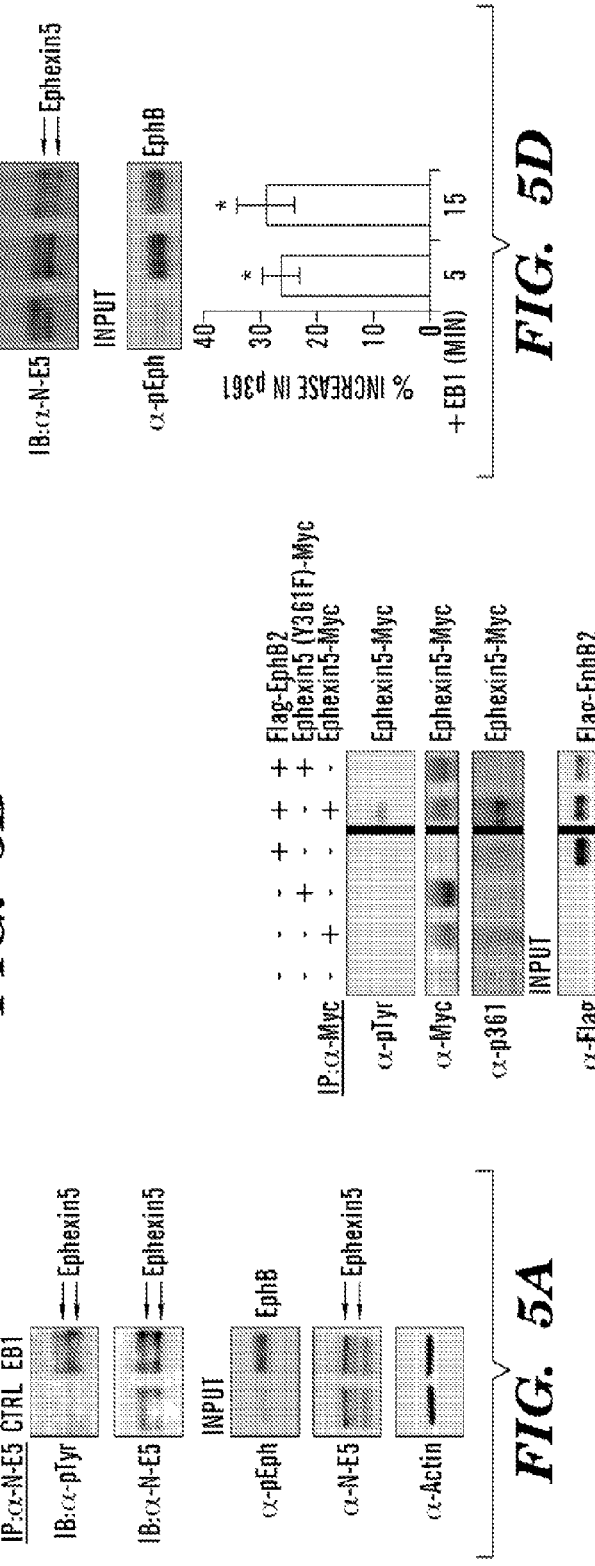

METHOD FOR DETERMINING ACTIVATORS OF EXCITATORY SYNAPSE FORMATION

GOVERNMENT SUPPORT

This invention was made with government support under grant no. RO1 5R01NS045500 awarded by the National Institute of Neurological Disorders and Stroke, and grant no. 5 T32 AG00222-15 awarded by the National Institutes of Health. The government has certain rights in this invention.

CROSS-REFERENCE TO RELATED APPLICATIONS

This application is a 35 U.S.C. §371 National Phase Entry Application of International Application No. PCT/US2011/057639 filed Oct. 25, 2011, which designates the U.S., and claims benefit under 35 U.S.C. §119(e) of the U.S. Provisional Application No. 61/406,757, filed Oct. 26, 2010, content of both of which is incorporated herein by reference in their entirety.

FIELD OF THE INVENTION

The invention relates to methods of screening inhibitors of Ephexin5. The invention further relates to inhibiting Ephexin5 to increase spine/excitatory synapse formation or numbers.

BACKGROUND OF THE INVENTION

A crucial early step in the formation of excitatory synapses is the physical interaction between the developing presynaptic specialization and the postsynaptic dendrite (Jontes et al., 2000; Ziv and Smith, 1996). This step in excitatory synapse development is thought to be mediated by cell surface membrane proteins expressed by the developing axon and dendrite and appears to be independent of the release of the excitatory neurotransmitter glutamate (reviewed in Dalva et al., 2007). Subsequent steps in excitatory synapse development require the release of glutamate at the developing excitatory synapse. For example, glutamate binding to N-methyl-D-aspartate (NMDA) receptors on the postsynaptic neuron stimulates the maturation of dendritic spines, protrusions on dendrites that are the major sites of excitatory synapses in the brain (Kopec et al., 2006; Matsuzaki et al., 2004). In addition, neuronal activity promotes the use-dependent strengthening of some excitatory synapses and the elimination of many weaker excitatory synapses (reviewed in Greer and Greenberg, 2008).

Several recent studies have revealed an important role for Ephrin cell surface-associated ligands and Eph receptor tyrosine kinases in the early cell-cell contact phase that is critical for excitatory synapse formation (Dalva et al., 2000; Ethell et al., 2001; Henkemeyer et al., 2003; Kayser et al., 2006; Kayser et al., 2008; Lai and Ip, 2009; Murai et al., 2003). Ephs can be divided into two classes, EphA and EphB, based on their ability to bind the ligands EphrinA and EphrinB, respectively (reviewed in Flanagan and Vanderhaeghen, 1998). There are five EphBs (EphB1-4, EphB6), three of which (EphB1-3) are highly expressed in neurons (reviewed in Flanagan and Vanderhaeghen, 1998). EphBs have been mainly shown to be expressed postsynaptically on the surface of developing dendrites, while their cognate ligands, the EphrinBs, are expressed on both the developing axon and dendrite (Grunwald et al., 2004; Grunwald et al., 2001; Lim et al., 2008). When an EphrinB encounters an EphB on the developing dendrite, EphB becomes autophosphorylated, thus increasing its catalytic kinase activity (reviewed in Flanagan and Vanderhaeghen, 1998). This then leads to a cascade of signaling events culminating in actin cytoskeleton remodeling that is critical for dendritic spine and excitatory synapse development (reviewed in Klein, 2009). Consistent with a role for EphBs in excitatory synapse development, EphB1/EphB2/EphB3 triple knockout mice have fewer mature excitatory synapses in vivo in the cortex, and fewer dendritic spines on CA1 and CA3 pyramidal neurons in the hippocampus (Henkemeyer et al., 2003; Kayser et al., 2006). In addition, the disruption of EphB function postsynaptically in dissociated hippocampal neurons leads to defects in spine morphogenesis and a decrease in excitatory synapse number (Ethell et al., 2001; Kayser et al., 2006). Conversely, activation of EphBs in cultured mouse hippocampal neurons leads to an increase in both the number of mature dendritic spines and functional excitatory synapses (Henkemeyer et al., 2003; Penzes et al., 2003; Tolias et al., 2005). Taken together, these findings indicate that EphBs are positive regulators of excitatory synapse development.

EphrinB binding to EphB triggers the recruitment of the NMDA sub-type of glutamate receptors, a calcium-permeable glutamate receptor that has been implicated in the initiation of neuronal activity-dependent synaptic development, excitotoxicity, and neuronal plasticity (Dalva et al., 2000; Takasu et al., 2002). In addition, EphB activation facilitates the recruitment of postsynaptic proteins, including the scaffold protein PSD-95 and the AMPA subtype of glutamate receptors that are critical for postsynaptic development and function (Cabo et al., 2006; Contractor et al., 2002; Henkemeyer et al., 2003; Kayser et al., 2006). The molecular mechanisms by which EphB orchestrates these steps in postsynaptic development are thought to involve EphB-PDZ interactions and the EphB-catalyzed phosphorylation/activation of several guanine nucleotide exchange factors (e.g., Tiam1, Kalirin, and Intersectin) which regulate the Rho family of small G proteins, including Rac1 and Cdc42 (Kayser et al., 2006; Klein, 2009). EphB tyrosine phosphorylation of the RacGEFs Tiam1 and Kalirin7 has been shown to correlate with Rac1 activation and the subsequent activation of p21-activated kinase (PAK) (Penzes et al., 2003, Tolias et al., 2005, Tolias et al., 2007). These events promote changes in the actin cytoskeleton that enhance filopodial motility on the developing dendrite (Kayser et al., 2008). This may then result in an increase in the likelihood that dendritic filopodia will encounter a presynaptic partner and form a synapse. EphB activation also leads to changes in the actin cytoskeleton that are critical for spine morphogenesis and the recruitment of essential postsynaptic components such as NMDA receptors, AMPA receptors, and PSD-95 to the dendritic spine (Dalva et al., 2000; Kayser et al., 2006; Klein, 2009; Penzes et al., 2003). Inhibition of Rac1 or PAK activity blocks the ability of activated EphBs to promote excitatory synapse development, in part through blocking EphB-mediated changes in filopodia movement and possibly by disrupting the recruitment of key proteins to the postsynaptic region (reviewed in Dalva et al., 2007)

While there has been considerable progress in characterizing the mechanisms by which EphBs promote excitatory synapse development, it is not known if there are EphB-associated factors that restrict the timing and extent of excitatory synapse development.

Accordingly, there is a need in the art for methods of determining activators of excitatory synapse formation that can act on EphBs and/or EphB associated factors.

SUMMARY OF THE INVENTION

In one aspect, the invention provides a method for screening a compound that increases spine/excitatory synapse formation and/or numbers, the method comprising contacting Ephexin5 with a test compound and selecting the compound that inhibits Rho GEF activity of Ephexin5.

In another aspect, the invention provides a method for increasing spine/excitatory synapse formation and/or numbers, the method comprising contacting a neuron with an Ephexin5 inhibitor.

In yet another aspect, the invention provides a kit for screening compounds and compositions useful as Ephexin5 inhibitors, the kit comprising at least one of the following: a peptide comprising the amino acid sequence of Ephexin5 or a conservative variant thereof; a nucleotide encoding a peptide comprising the amino acid sequence of Ephexin5 or a conservative variant thereof; or a cell comprising a polynucleotide encoding a peptide comprising the amino acid sequence of Ephexin5 or a conservative variant thereof.

BRIEF DESCRIPTION OF THE DRAWINGS

This patent or application file contains at least one drawing executed in color. Copies of this patent or patent application with color drawing(s) will be provided by the Office upon request and payment of necessary fee.

FIG. 1A, Ephexin5 and EphB2 are expressed in the CA1 and dentate gyrus (DG) of the hippocampus at P12. P12 mice were perfused with paraformaldehyde, frozen and sectioned. Adjacent 100 nm brain sections were stained for Ephexin5 or EphB2 using digoxigenin-labelled RNA probes to the sense or anti-sense strands. Image shows staining of CA1 and DG of Ephexin5 or EphB2 using anti-sense probes and not the control sense-probes (above panels). Lower panels show nuclei staining with DAPI. FIG. 1B, Ephexin5 preferentially interacts with EphB. Lysates from HEK293T cells, transfected with various combinations of overexpressing plasmids containing Ephexin1-Myc, Ephexin5-Myc, Flag-EphB2, and Flag-EphA4, were immunoprecipitated with anti-Flag antibody. Following immunoprecipitation, samples were resolved by SDS-PAGE and probed for Ephexin or Eph with Myc or Flag antibodies, respectively. Input Eph and Ephexin levels were determined by immunoblotting lysate with Myc and Flag antibodies, respectively (bottom panels). FIG. 1C, Ephexin5 and EphB2 interact in neurons. E16 mouse cortical cell lysates were lysed and immunoprecipitated with rabbit IgG or anti-C-terminal Ephexin5 (a-C-E5), followed by immunoblotting for EphB2 (a-EphB2) and Ephexin5 (a-N-E5). Input levels of EphB2 and Ephexin5 were determined by immunoblotting whole lysate (right panels). FIG. 1D, Anti-Ephexin5 immunoprecipitation of EphB is dependent on Ephexin5. Whole brain lysates were prepared from wild type (E5+/+) or Ephexin5 knockout (E5−/−) mice. Lysates were incubated with anti-Ephexin5 antibody and precipitated using protein A sepharose. Immunoprecipitated samples were run on SDS-PAGE for western blot analysis using an anti-EphB antibody. Western blotting of input lysates demonstrates similar EphB2 expression levels in both samples. FIG. 1E, Ephexin5 co-localization with EphB along the dendrite changes during development. Dissociated hippocampal neurons transfected with 250 ng of GFP were fixed and stained for endogenous phexin5 using rabbit anti-N-terminal Ephexin5 (a-N-E5) (Blue) and goat anti-EphB2 antibody (Red). A representative image of the quantified puncta is shown on the left with arrows pointing to overlapped EphB and Ephexin5 (GFP not shown). Using MetaMorph analysis, colocalization of EphB and Ephexin5 puncta on the GFP-transfected neurons was determined and represented as % of EphB overlapped with Ephexin5. EphB2 overlap with Ephexin5 was determined at DIV2, DIV4 and DIV8. A statistically significant decrease (***p<0.05) in EphB2 overlap with Ephexin5 is observed from DIV2 to DIV8.

FIG. 2A, Ephexin5 activates RhoA signaling. Lysates from HEK293T cells transfected with empty vector or Ephexin5-Myc overexpressing vector were assayed for endogenous RhoA activity using the RBD pulldown assay and analyzed by immunoblotting with an antibody to RhoA (top panel). Increased endogenous RhoA activity is demonstrated by presence of anti-RhoA signal in RBD pulldown lanes. Total protein levels were assessed by immunoblotting for RhoA, Ephexin5-Myc, and β-Actin (Input panels). FIG. 2B, Ephexin5 does not activate Rac1 or Cdc42. Lysates from HEK293T cells transfected with empty vector, Ephexin5-Myc, or Ephexin1-Myc were assayed for activated Rac1 and Cdc42 using the PBD pulldown assay. Pulldown lanes were immunoblotted with a mouse anti-Rac1 and re-probed with a rabbit anti-Cdc42 (top two panels). Increased endogenous Rac1 or Cdc42 activity is demonstrated by presence of anti-Rac1 or anti-Cdc42 signal in PBD pulldown lanes. Total protein levels were assessed by immunoblotting for Rac1, Cdc42, Ephexin-Myc, and β-Actin (Input panels). FIG. 2C, Sequence alignment of the a5 helix loop of DH domain of known RhoA-specific GEFs using the ClustalW algorithm. Asterisks highlight residues previously shown to be important for activity of these known GEFs. Sequences are FLLLPFQRITRL (SEQ ID NO: 1, Ephexin5), FLDIPRSRLVKY (SEQ ID NO: 2, NET1), IIPTQMQRLTKY (SEQ ID NO: 3, LARG), MLAKPHQRLTKY (SEQ ID NO: 4, TECH), CILLVTQRITKY (SEQ ID NO: 5, LBC), YLLKPVQRITKY (SEQ ID NO: 6, DBS), and FLL+P-QR+TKY (SEQ ID NO: 7, Consensus). FIG. 2D, Amino acids LQR within the a5 helix of the Ephexin5 DH domain are required for Ephexin5 mediated changes in RhoA signaling. Lysates from HEK293T cells transfected with empty vector, Ephexin5-Myc (WT), and Ephexin5-LQR-Myc (LQR) were assayed for activated RhoA using RBD pulldown assay as described in part A (top panel). Total protein levels were assessed by immunoblotting for Ephexin-Myc and β-Actin (Input panels). FIG. 2E, Presence of wild type levels of Ephexin5 is critical for wild type levels of endogenous RhoA signaling in vivo. P7 mouse whole brain lysates from wild type (WT) or Ephexin5−/−(KO) littermates were blinded to condition and subjected to RBD pulldown assays as described in part A (top panel). Total protein levels were assessed by immunoblotting brain lysates for Ephexin5, RhoA, and β-Actin (Input panels). The anti-RhoA signals in the RBD pulldown lanes of three independent experiments were quantified by densitometry and ImagJ. This quantification shows a statistically significant (***p<0.05) 4-fold decrease in anti-RhoA signal from RBD pulldown assays using Ephexin5−/−brain lysates compared to wild type brain lysates. Quantification of each lane is normalized to input RhoA signal.

FIG. 3A, Ephexin5 is required for restricting development of dendritic spines. Ephexin5 shRNA (E5 shRNA) or scrambled shRNA (control shRNA) (10 ng) was co-transfected with GFP into rat hippocampal neurons at DIV14. At DIV18, transfected neurons were fixed and spines quantified by MetaMorph. Representative image illustrates quantified GFP-filled neurons. Data represent three separate experiments. All error bars are SEM; p<0.01, ANOVA. FIG. 3B, Ephexin5 negatively regulates the number of excitatory synapses. 10 ng or 20 ng of two different Ephexin5 shRNA constructs or scrambled shRNA (control shRNA) construct were transfected into rat hippocampal neurons at DIV10. At DIV14, transfected neurons were fixed and stained for excitatory synapse markers (PSD-95/Synapsin). Neurons were imaged using confocal microscopy and overlapping puncta quantified by MetaMorph. Representative image illustrates counted puncta (White). All error bars are SEM; $p<0.01$, *$p<0.005$, ANOVA. FIG. 3C, Ephexin5 restricts excitatory synapse density. At DIV10, rat hippocampal neurons were transfected with increasing concentrations of Ephexin5-Myc plasmid or control plasmid and GFP. At DIV14, neurons were fixed and stained for either anti-Myc or PSD-95/Synapsin to quantify Ephexin5 expression levels and excitatory synapse number, respectively. Representative image illustrates localization of overexpressed Ephexin5 on GFP-labeled neuron (Red). All error bars are SEM; $p<0.01$, ANOVA. FIG. 3D, Ephexin5 GEF activity is required to restrict excitatory synapse density. At DIV10, rat hippocampal neurons were transfected with increasing concentrations of Ephexin5-Myc (Ephexin5-WT) or Ephexin5-LQR-Myc (Ephexin5-LQR) plasmid and GFP. Data represent two independent experiments. All error bars are SEM; $p<0.01$, ANOVA. FIG. 3E, Ephexin5 is required for restricting functional excitatory synapses. DIV10 neurons were transfected with 20 ng of Ephexin5 shRNA or scrambled shRNA (control). At DIV14, several neurons from experimental and control conditions were whole-cell patched and mEPSCs recorded. Cumulative distribution plots and bar graphs show decreases in mEPSC inter-event interval and an increase in amplitude (pA) following knockdown of Ephexin5. This result represents four independent experiments (14 neurons per condition, *$p<0.005$, **$p<0.05$). All error bars are standard deviation of the mean. A representative trace from each condition is shown.

FIG. 4A, Ephexin5 is required for restricting excitatory synapses from Ephexin5 knockout mouse brains. For mouse cultures, E16 animals heterozygous or knocked out for Ephexin5 were dissected and hippocampal cultures dissociated. At DIV10 neurons were transfected with GFP. At DIV14, neurons were fixed and stained for the excitatory markers PSD-95/Synapsin. Two littermate animals were used per condition for each of three independent experiments performed. All error bars are SEM; *$p<0.005$, ANOVA. FIG. 4B, Ephexin5 is required for spine restriction in an intact circuit. Organotypic slices were prepared from P7 Ephexin5$^{+/+}$ and Ephexin5$^{fl/fl}$ littermates and biolistically transfected at DIV3 with Cre or control plasmid and GFP. At DIV7, neurons were fixed and mounted for imaging. Over 200 .m of apical dendrites were imaged per neuron, with 10 neurons imaged per animal totaling over 3000 spines. Data represent at least two animals from a total of two different litter pairs quantified at the same time. These results were verified by blinded counting and quantification from a third party to verify significance. All error bars are SEM; *$p<0.005$, KS test. FIG. 4C, Ephexin5 regulates excitatory synapse development in vivo. Acute hippocampal brain slices were prepared from P12-P14 wild type or Ephexin5$^{-/-}$ mice. Pyramidal neurons were whole cell patched in the CA1 region of the hippocampus. As compared to wild type mouse neurons, the neurons from brains of Ephexin5$^{-/-}$ mice show a decrease in the interval between mEPSCs (left side) and an increase in mEPSC amplitude (pA) (right side). These data represent six independent experiments (12 neurons per condition, *$p<0.005$, $p<0.05$). FIG. 4D, Ephexin5 is required for in vivo development of excitatory synapses. Hippocampi from three independent littermate pairs consisting of a P12 wild type and Ephexin5 knockout mouse were prepared according to materials and methods. For each hippocampus, 50 sections of 100 nm thickness were arrayed on glass coverslips and incubated with primary antibodies (antisynapsin-1 (red) and anti-PSD-95 (green) antibodies) followed by fluorescent secondary antibodies. For each animal we generated five independent image stacks each consisting of 30 consecutive sections in the stratum radiatum of the CA1. Number and overlap of synapsin-1 (red) and PSD-95 (green) puncta were quantified in three-dimensions for each stack and divided by density of volume quantified. Samples from Ephexin5 knockout mice were normalized to wild types for each measurement quantified (*$p<0.05$, Mann-Whitney U-Test). FIG. 4E, Increase in excitatory synapse number following loss of Ephexin5 function requires EphB signaling. Increasing concentrations of EphB2KD plasmid were transfected in rat hippocampal neurons at DIV10 and co-expressed with scrambled control (Control shRNA) or Ephexin5 shRNA. Cells were fixed and stained for PSD-95 and Synapsin at DIV14, imaged and quantified for excitatory synapses. These data are the product of two independent repeats. All error bars are SEM; $p<0.01$, *$p<0.005$, ANOVA. FIG. 4F, Ephexin5 can suppress an EphB-mediated increase in excitatory synapse number. Increasing concentrations of EphB-expressing plasmid were transfected in rat hippocampal neurons at DIV10 and co-expressed with control plasmid or E5 overexpressing plasmid. Cells were fixed and stained for PSD-95 and Synapsin at DIV14, imaged and quantified for excitatory synapses. All error bars are SEM; $p<0.01$, ***$p<0.005$, ANOVA.

FIGS. 5A-5G show that EphB mediates phosphorylation of Ephexin5 at tyrosine-361. FIG. 5A, Endogenous Ephexin5 is tyrosine phosphorylated upon EphrinB1 stimulation in neurons. E16 dissociated mouse hippocampal neurons were cultured for one day in vitro and stimulated with either anti-FC IgG (Ctrl) or pre-clustered FC-EphrinB1 (EB1) for 15 minutes. Neurons were lysed and immunoprecipitated with a rabbit α-N-terminal Ephexin5 (α-N-E5). Immunoprecipitation lanes were immunoblotted for pan-phosphotyrosine (α-pTyr) and Ephexin5. Efficiency of EphrinB1 stimulation was determined by immunoblotting neuronal lysates for phospho-Eph (Input, top panel). Input protein levels were determined by blotting neuronal lysates for Ephexin5 and β-Actin (Input). FIG. 5B, Ephexin5-Y361 is a conserved residue with Ephexin1's previously characterized tyrosine phosphorylation site at amino acid 87 (Sahin et al., 2005). Sequences are RNLIEQIGLLYQTYRDKSTLQE (SEQ ID NO: 8, Ephexin 1(77-98)), WELPLQDEPLYQEYHAAVL-SEE (SEQ ID NO: 9, Ephexin5 (351-372)), and LQLYQYRE (SEQ ID NO: 10, consensus). FIG. 5C, Ephexin5 Y361 is a major EphB2-mediated phosphorylation site. Lysates from HEK293T cells transfected in combination with Ephexin5-Myc, Ephexin5-Myc (Y361F), or Flag-EphB2 were boiled in SDS buffer (to remove EphB interaction with Ephexin5), diluted in lysis buffer, and immunoprecipitated with Myc antibody. Immunoprecipitation lanes were immunoblotted for pan-phosphotyrosine with 4G10 (α-pTyr) and phosphorylated Y361 (α-pY361). To assess Ephexin5 levels, immunoprecipitation lanes were stripped and reprobed with Myc antibody. Levels of EphB2 expression were determined by blotting boiled cell lysates (bottom panel). FIG. 5D, Endogenous Ephexin5 is phosphorylated at Y361 upon EphrinB1 stimulation. E16 dissociated mouse hippocampal neurons were cultured for one day in vitro and stimulated with either anti-FC IgG (ctrl) for 15 minutes or pre-clustered FC-EphrinB1 (EB1) for 5 and 15 minutes. Neurons were lysed and immunoprecipitated with a rabbit α-N-terminal Ephexin5 antibody (α-N-E5). Immunoprecipitation lanes were immunoblotted for Ephexin5-pY361 (α-pY361) and Ephexin5 (α-N-E5). Efficiency of EphrinB1 stimulation was determined by immunoblotting neuronal lysates for phospho-Eph (α-pEph) (Input, top panel). Western blots are quantified using densitometry and represented as percent increase in phosphorylation of EphrinB1-stimulated versus control stimulated (*p<0.05). FIG. 5E, Ephexin5 is phosphorylated at Y361 along developing dendrites. At DIV2 rat hippocampal neurons were transfected with 250 ng of GFP and stimulated with either anti-FC IgG (EphrinB1) or pre-clustered FC-EphrinB1 (+EphrinB1) for 15 minutes, followed by fixing and staining for endogenous Ephexin5 using rabbit α-pY361 (Red). Transfected neurons were imaged and analyzed for Ephexin5-Y361. Ephexin5 pY361 puncta staining is quantified using MetaMorph (*p<0.05). FIG. 5F, Ephexin5 phosphorylation by EphB2 leads to decreased Ephexin5 GEF activity. Lysates from HEK293T cells transfected with a control vector, increasing concentrations of Ephexin5-Myc, Flag-EphB2 alone, or increasing concentrations of Ephexin5-Myc co-expressed with FlagEphB2 were assayed for activated RhoA signaling using RBD pulldown assay (top panel). Total protein levels were assayed by immunoblotting for RhoA, Ephexin-Myc, Flag, and β-Actin (Input panels). FIG. 5G, EphB2 is required for Ephexin5 phosphorylation and degradation in vivo. EphB2 wild type and knock-out brains were lysed and prepared for SDS-PAGE, followed by western analysis of total Ephexin5 protein (α-N-E5) and phosphorylated tyrosine on Ephexin5 at Y361 (α-pY361). Samples were visualized using fluorescently labeled secondary antibodies followed by imaging by Licor fluorescent imager. Western image is representative of three separate wild type EphB2 knockout littermate pairs. Quantification of total Ephexin5 expression is normalized to actin to control for variation in loading of samples and then represented as fold change in Ephexin5 levels compared to Ephexin5 levels from brain lysates of EphB2 wild type mice. Phosphorylated Ephexin5 at Y361 is normalized to actin and Ephexin5 expression. The quantification of Y361-phosphorylated Ephexin5 is represented as fold change in normalized phosphorylated Ephexin5 levels compared to the normalized phosphorylated Ephexin5 levels from brain lysates of EphB2 wild type mice (*p<0.05).

FIG. 6A, Overexpression of EphB2 (α-Flag-Blue) in neurons at DIV10 leads to a decrease in endogenous Ephexin5 (α-N-E5-Red) by DIV14 in the transfected neuron as measured by immunocytochemistry. Images were quantified by MetaMorph. The data represent three independent experiments. EphB2 is labeled as EB2. FIG. 6B, Endogenous Ephexin5 protein level decreases in response to EphrinB1 stimulation. Mouse hippocampal neurons were incubated with pre-clustered FC-EphrinB1 or FC-EphrinA1 for either 30 or 60 minutes, lysed, and immunoblotted for endogenous Ephexin5 (α-N-E5). Western is one representative image and quantification is of three separate experiments. Samples are normalized to β-Actin. Endogenous Ephexin5 protein expression decreases at dendrites upon EphrinB1 stimulation. Rat hippocampal neurons were transfected with eGFP at DIV10, treated with clustered EphrinB1 for 30 minutes, and fixed and stained for Ephexin5 protein. Neurons were imaged for total Ephexin5 protein staining over the total area of neuron imaged. The levels of staining in the dendritic areas were compared to those in the cell soma. FIG. 6C, Endogenous Ephexin5 protein level, but not transcript, decreases in the hippocampus in vivo during postnatal synapse development. Hippocampi were dissected from wild type animals at different time points, immediately lysed, and immunoblotted for Ephexin5 (α-N-E5) (top panel). Lysates from Ephexin5$^{+/+}$ and Ephexin5$^{-/-}$ P14 mouse brains were used to control for antibody recognition (right panel). Northern analysis of wild type brains were also analyzed for changes in Ephexin5 RNA. Schematic of Ephexin5 genomic locus shows location of northern probe (bottom panels). FIG. 6D, EphB mediates decrease of Ephexin5 protein levels, but not Ephexin1. Ephexin5-Myc, or Ephexin1-Myc was co-transfected in HEK293T cells with a control plasmid or a plasmid containing Flag-EphB2. Cell lysates were run on SDS-PAGE, and immunoblotted with anti-Myc to assay Ephexin protein levels (Top panel). For input controls, lysates were immunoblotted for EphB2 and actin with anti-Flag and anti-.actin, respectively. FIG. 6E, Decrease in Ephexin5 protein requires EphB2 kinase activity. Flag-EphB2 or Flag-EphB2KD (EphB kinase dead (KD)) was co-transfected into HEK293T cells in the presence of Ephexin5Myc. Cell lysates were prepared and run on SDS-PAGE for western blot using antibodies to Ephexin5-Myc, Flag-EphB2 and β-Actin. FIG. 6F, Ephexin5 Y361 phosphorylation is the EphB2 target site required for degradation. Coexpression of Ephexin5-Y361F-Myc and Flag-EphB2 in HEK293T cells leads to a suppression of the EphB2-induced decrease of Ephexin5 protein level as measured by immunoblotting with antibodies to Myc and Flag. β-Actin levels were immunoblotted for loading control. FIG. 6G, EphB2-mediated decrease in Ephexin5 requires the proteasome. Overexpression of Ephexin5-Myc in HEK293T cells in the presence (4 hrs.) or absence of the proteasome inhibitor lactacystin were immunoprecipitated with an anti-Myc and run on SDS-PAGE followed by immunoblotting for Ephexin5 (α-N-E5) or ubiquitin (α-ub). In the presence of lactacystin, Ephexin5 is dramatically ubiquitinated (left panels). FIG. 6H, Decrease in Ephexin5 protein level at sites where synapses form is reversed by the proteasome inhibitor lactacystin. As in FIG. 6B, treating the cells with lactacystin (4 hrs) suppressed the EphrinB-mediated decrease in Ephexin5 levels along the dendrite. FIG. 6I, Endogenous Ephexin5 is ubiquitinated. Ephexin5$^{+/+}$ and Ephexin5$^{-/-}$ brains were lysed in RIPA buffer containing N-Methylmalaeimide to preserve ubiquitin species and immunoprecipitated with anti-Ephexin5 antibodies. Samples were run on SDS-PAGE and immunoblotted with α-NE5 and α-ub.

FIG. 7A, Ube3A interacts with Ephexin5. Lysates from HEK293T cells transfected with Ephexin1-Myc, Ephexin5-Myc, and/or HA-C833A (dominant negative Ube3A), HA-Mef2A, HA-Cbl, HA-Ube3A were immunoprecipitated with HA antibody followed by immunoblotting with HA or Myc antibody to assay for immunoprecipitated HA-tagged protein and Ephexins, respectively. FIG. 7B, Ube3A mediates decrease of Ephexin5 protein levels. Overexpression of Ephexin5-Myc in HEK293T cells with Ube3A leads to a marked decrease in protein levels as determined by western blot analysis of total lysates. Cbl does not affect levels of Ephexin5-Myc in HEK293T cells. Levels of Ube3A and Cbl were determined by immunoblotting with antibodies to HA. Loading was controlled by immunoblotting for .actin. FIG. 7C, Endogenous Ephexin5 protein levels decrease in response to EphrinB1 stimulation by a Ube3A-dependent mechanism. Mouse neurons were transfected with GFP and control, Ube3A dominant negative (Ube3A DN) or shRNA for Ube3A at DIV10. Four days later on DIV14, indicated neurons were incubated with clustered EphrinB1 for 30 minutes. Neurons were fixed and stained for Ephexin5. Using MetaMorph, the Ephexin5 puncta were quantified and divided by the area of the transfected neuron to assess Ephexin5 density. Quantification is of relative Ephexin5 puncta density compared to control. All error bars are SEM; p<0.01, ANOVA. FIG. 7D, Endogenous Ephexin5 protein level decreases in the presence of wild type Ube3A, but not dominant negative Ube3A (dnUbe3A). As in C) neurons were transfected on DIV10 and imaged on DIV14. Quantification similar to C). All error bars are SEM; p<0.01, ANOVA. FIG. 7E, Total Ephexin5 protein level is increased in Ube3A knockout brains. Ube3A wild type and knockout brains were lysed and prepared for SDS-PAGE followed by western analysis of Ephexin5 and other neuronal proteins. Samples were visualized using fluorescently labeled secondary antibodies followed by imaging by Licor fluorescent imaging (Odyssey System). Samples were quantified. Image is representative of three separate samples quantified. P8 brains were only blotted for Ephexin5. FIG. 7F, Endogenous Ephexin5 ubiquitination is decreased in Ube3A knockout mouse brains. Ube3A wild type and knockout mouse brains were lysed in RIPA buffer containing N-Methylmalaeimide to preserve ubiquitin species and immunoprecipitated with anti-Ephexin5 antibodies. Samples were run on SDS-PAGE and immunoblotted for Ephexin5 ($\alpha$-N-E5) and ubiquitin ($\alpha$-ub). Input panel shows immunoblot of total lysate, prior to immunoprecipitation, of Ephexin5 ($\alpha$-N-E5) and Ube3A (a-Ube3A). FIG. 7G, EphrinB1-mediated degradation of Ephexin5 requires Ube3A. Hippocampal neurons from Ube3a maternal-deficient mice and wild type littermates were dissociated and cultured. At DIV8 neurons were incubated in the presence or absence of EphrinB1 for 45 minutes. Samples were fixed and stained with anti-Ephexin5 antibody to measure endogenous Ephexin5 expression levels by MetaMorph. Our data indicate a decrease in Ephexin5 expression in wild type neurons treated with EphrinB1 as compared to control. Conversely, there is no decrease in Ephexin5 expression in Ube3A maternal-deficient neurons treated with EphrinB1 as compared to control.

FIG. 8A, Scheme used to generate the Ephexin5$^{-/-}$ and Ephexin5$^{fl/fl}$ mice. FIG. 8B, Southern blot showing the successful removal of exons 4 through 8 in the Ephexin5 gene in mouse ES cells. Genomic DNA was digested with HindIII and hybridized with a 5' probe shown in FIG. 8A. FIG. 8C, PCR analysis of genomic tail DNA showing that the Ephexin5 gene is correctly recombined in Ephexin5$^{-/-}$ and Ephexin5$^{fl/fl}$ mice. FIG. 8D, Western blot showing that Ephexin5 protein is absent in Ephexin5$^{-/-}$ mice. EphB2 and $\beta$-Actin serve as a loading control. FIG. 8E, Immunocytochemistry of dissociated cultures from Ephexin5$^{+/-}$ and Ephexin5$^{-/-}$ mice reveals specific staining of Ephexin5 along the dendrite of the developing neuron, near dendritic spines, and within the soma. FIG. 8F, Ephexin5 is expressed exclusively in the dendrite of the developing hippocampus. Cultured hippocampal neurons were transfected with GFP at DIV8 and fixed and stained two days later for endogenous Ephexin5 expression (red) and the dendritic marker Map2 (Blue). Overlapped Map2/GFP staining indicates dendrites. Conversely, subtraction of Map2-positive processes from GFP-labeled neuronal staining indicates location of axons. To measure Ephexin5 density, the number of Ephexin5 puncta were divided by the area of the GFP dendritic or axonal field. Quantification was done using MetaMorph.

FIG. 10A, Genomic structure of the Ephexin5 gene. The genomic location and shRNA sequence used for Ephexin5 knockdown are shown. Sequence are TAGCCGCCTTATG-GATACAAA (SEQ ID NO: 11, Ephexin5 shRNA 5"), CCCT-GCAGGACGAACCTTTAT (SEQ ID NO: 12, Ephexin5 shRNA 6"), and TCCGAAAGCACTTCCTCAAAT (SEQ ID NO: 13, Ephexin5 shRNA 7"). FIG. 10B, Western blot showing that exogenously expressed Ephexin5 protein can be knocked down in HEK293T cells in the presence of shRNA constructs. Only two of the three shRNA constructs were capable of knocking down Ephexin5 protein expression. FIG. 10C, Rat hippocampal neurons were transfected with GFP and shRNA targeted to Ephexin5 gene at DIV10. At DIV14, neurons were fixed and stained for endogenous Ephexin5 protein. Immunocytochemistry shows that Ephexin5 shRNA-expressing neurons have a dramatic decrease in endogenously expressed Ephexin5. FIG. 10D, Loss of Ephexin5 function does not affect dendritic spine morphology. 10 ng of Ephexin5 shRNA (E5 shRNA) or scrambled shRNA (scr shRNA) was co-transfected with GFP into rat hippocampal neurons at DIV14. At DIV18, transfected neurons were fixed and spines quantified for spine length and head width. Data are plotted as cumulative distribution to identify populations of spines that have changed in length or width. All error bars are SEM; *p<0.002.

FIG. 12A, Both the EphB2 cytoplasmic domain and kinase domain are necessary for Ephexin5 phosphorylation, but only the EphB2 cytoplasmic domain is required for the EphB2 interaction with Ephexin5. HEK293T cell lysates from transfected cells with Ephexin5-Myc with either FlagEphB2, Flag-EphB2-kinase dead (KD), or Flag-EphB2-Acyto were immunoprecipitated with Flag antibody followed by immunoblotting with Flag or with Myc antibodies to assay for immunoprecipitated Ephs and Ephexin5, respectively. Cell lysates were immunoblotted for Myc and pY361. FIG. 12B, Ephexin5 is preferentially phosphorylated by EphB2. HEK293T cell lysates from cells transfected with the indicated Ephs, with or without Ephexin5-Myc were immunoblotted with antibodies to Ephexin5-pY361, Myc, and Actin. FIG. 12C, Ephexin5 is phosphorylated in mouse brain at Y361. Whole brain lysates from P3 wild type (WT) and Ephexin5$^{-/-}$ (KO) littermates were lysed and immunoblotted with $\alpha$-pY361, $\alpha$-Ephexin5 ($\alpha$-N-E5) and $\alpha$-$\beta$-Actin.

FIG. 15A, Ephexin5, via its RhoA GEF activity, restricts early spine and synapse formation along the developing dendrite prior to the EphB-dependent phase of synapse development. FIG. 15B, Presynaptic EphrinB on the incoming axon contacts postsynaptic EphB receptor tyrosine kinases along the developing dendrite. Subsequent autophosphorylation of EphBs leads to the tyrosine phosphorylation and the Ube3a-dependent degradation of Ephexin5 at nascent synaptic sites. This allows EphB-mediated synapse formation to ensue, in part, through the recruitment and activation of Rac GEFs.

DETAILED DESCRIPTION OF THE INVENTION

Figure 1A:
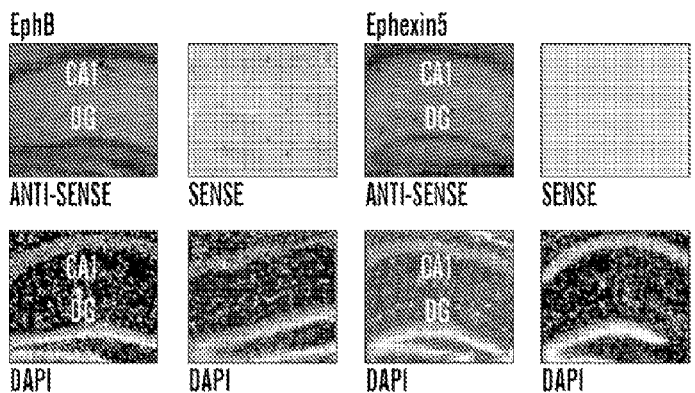
FIGS. 1A-1E show that Ephexin interacts with EphB.

The mechanisms that promote excitatory synapse formation and maturation have been extensively studied. However, the molecular events that limit excitatory synapse development so that synapses form at the right time and place and in the correct numbers are less well understood. Now, the inventors have discovered a RhoA guanine nucleotide exchange factor, Ephexin5, which negatively regulates excitatory synapse development until EphrinB binding to the EphB receptor tyrosine kinase triggers Ephexin5 phosphorylation, ubiquitination, and degradation. Accordingly, in one aspect, the invention provides a method for screening a compound that increases spine/excitatory synapse formation and/or numbers, the method comprising contacting Ephexin5 with a test compound and selecting the compound that inhibits Ephexin5 activity. In some embodiments, Ephexin5 activity is the GEF activity for RhoA.

As used herein, the phrase "GEF activity for RhoA," or "activation of RhoA," or "RhoA GEF activity" means to exchange guanosine 5'-diphosphate (GDP), that is bound to RhoA, for guanosine 5'-triphosphate (GTP), and thereby to convert the RhoA from a GDPbound inactive form to a GTP-bound active form. This exchange reaction comprises a dissociation reaction of GDP from RhoA, and a binding reaction of GTP to the resultant RhoA, without a nucleotide being bound. Specifically, the phrase "GEF activity for RhoA," or "activation of RhoA," or "RhoA GEF activity" means to convert RhoA from an inactive form to an active form via an exchange reaction of RhoA-bound GDP for intracellular GTP.

The cellular activities mediated by Rho GTPases are dependent upon the activation state of the GTPase. When GTP is bound to Rho GTPases they are in an active state and are able to bind to effectors and propagate the signal cascade leading to a particular cellular response. When GDP is bound to Rho GTPases the Rho protein is inactive (Takai et al, 2001, Physiol. Rev, 81: 153-208). Several assays have been developed that monitor the activation state of Rho GTPases. Accordingly, RhoA GEF activity of Ephexin5 can be determined by assaying RhoA activation.

One assay, the Rho effector pull-down assay, was originally developed for RhoA GTPases by Ren et al. (1999, EMBO J, 18: 578-585) and for Rac1/Cdc42 GTPases by Benard et al. (1999, J. Biol. Chem, 274: 13198-13204) and is the classical and most widely used assay. The method involves capture of activated Rho GTPase proteins by effectors bound to beads, release of the GTPase protein from the beads, separation of the beads from the released GTPase protein, followed by SDS-PAGE and analysis of the GTPase protein by western blotting.

There are several cell-based assays that use fluorescent bio-probes to detect activated Rho GTPases (Pertz et al, 2004, J. Cell Sci, 117: 1313-1318). Several versions of this type of assay rely on a reporter system to monitor Rho GTPase activation. Other versions of cell-based assays use effector domains linked directly to an environmental dye to monitor endogenous GTPase activation. An automated cell-based Rho activation assay has also been reported (Teusch et al, 2006, Assay and Drug Devel., 4: 133). It is based on the ability of Rho to regulate the actin cytoskeleton.

An enzymatic based method to detect Rho activation has also been reported (Chen et al, 2003, J. Biol. Chem, 278: 2807). The assay utilizes GST-effector-GBD to affinity precipitate active GTP-Rho. GTP is eluted and converted to ATP in a coupled enzymatic assay. ATP is then measured by the firefly luciferase method.

RhoA activation can also be determined by incubating the RhoA with a protein that preferentially binds to the activated RhoA. For example, the proteins comprising a Rhotekin-Binding Domain are known to bind preferentially with active (GTP-bound) but not inactive (GDP-bound) RhoA. After incubation, the reaction mixture can be separated, e.g., by SDS-PAGE, and RhoA binding to the protein measured, e.g., by immunoblotting or immunostaining with anti-RhoA antibodies. In some embodiments, the protein is a fusion protein comprising a Rhotekin-Binding Domain. In some embodiments, the protein is a GST-fusion protein.

The Ephexin5 used in the screening assay can comprise the Ephexin5 amino acid sequence from any species or conservative variants thereof. Exemplary Ephexin5 amino acid sequences and/or polynucleotides sequences encoding Ephexin5 can be accessed with the following Reference Sequence Nos. and/or identifiers from the NCBI database: Rho guanine nucleotide exchange factor (GEF) 15, ARGEF15, KIAA0915, F1113791, Vsm-RhoGEF, Rho guanine exchange factor (GEF) 15, MGC44868, rho guanine nucleotide exchange factor 15, 155901, 228992, ENSG000001988447,0949893, GC17P008591, GC17P009307, GC17P008156, GC17P008414, MGC102247, MGC144141, MGC144142, D130071N09, D530030K12Rik, RP23-396M19.6, and Arhgef15. Ephexin5 can be obtained from any source known to one of ordinary skill in the art. Generally, Ephexin5 is expressed and purified from a cell expressing Ephexin5. It is to be understood that Ephexin5 does not need to be purified or isolated from the cell extract for use in the screening methods described herein. Without limitations, the Ephexin5 expressing cell can be a neuronal cell or a non-neuronal cell.

In some embodiments, Ephexin5 is human Ephexin5. In some embodiments, the human Ephexin5 can be encoded by the polynucleotide accessed by the NCBI Reference Sequence Nos. NM_173728 or NM_025014.

Epehxin5 is also known by various aliases in the art including, but not limited to, ARGEF15, FLJ13791, KIAA0915, MGC44868, Vsm-RhoGEF, and ARHGEF15. Accordingly, any of these alias can also be used to access Ephexin5 amino acid sequences and/or polynucleotide sequences encoding Ephexin5 from the NCBI database.

Ephexin5 can be expressed from an endogenous gene in the cell or from a vector that is transfected into the cell. When expressed from a vector, Ephexin5 can comprise additional domains or sequences for easy purification, labeling, conjugation etc. These additional domains or sequences can be present at the N-terminal, C-terminal or both terminals of the Ephexin5 sequence. For example, a vector for producing Myc-tagged mouse Ephexin5 can be produced as described in the examples section.

Alternatively, Ephexin5 can be chemically synthesized using methods well established in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N.L. Benoiton, Chemistry of Peptide Synthesis, CRC Press, Boca Raton, Fla. (2005); J. Jones, Amino Acid and Peptide Synthesis, $2^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), content of all of which is herein incorporated by reference in its entirety.

It is known in the art that limited modifications can be made to a peptide without destroying its biological function. Thus, modification of Ephexin5 that do not completely destroy Rho GEF activity are within the definition of the claims as such. Modifications can include, for example, additions, deletions, or substitutions of amino acids residues, substitutions with compounds that mimic amino acid structure or functions, addition of chemical moieties such as amino or acetyl groups, as well as replacement of peptide bonds. When Ephexin5 is modified, it is necessary that the modified Ephexin5 still retain at least 5%, at least 10%, at least 20%, at least 30%, at least 40%, at least 50%, at least 60%, at least 70%, at least 80%, at least 90%, or at least 95%, of Rho GEF activity relative to the Ephexin5.

In some embodiments, Ephexin5 comprises at least one amino acid selected from the group consisting of homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, and derivatives thereof.

In some embodiments, Ephexin5 comprises at least one D-amino acid.

In some embodiments, Ephexin5 comprises at least one beta-amino acid.

In some embodiments, Ephexin5 comprises at least one peptide bond replacement.

In some embodiments, Ephexin5 used in the screening assay is a functional fragment of Ephexin5. As used herein, the term "functional fragment" refers to fragment of Ephexin5 wherein the fragment retains Rho GEF activity as found with the full-length Ephexin5 from which it is derived. Functional fragment of a peptide can be created by deleting amino acids from the N-terminal and/or C-terminal of full length Ephexin5 amino acid sequence.

In some embodiments, Ephexin5 is immobilized on a solid support. Polypeptides can be immobilized using methods known in the art, such as adsorption onto a plastic microtiter plate or specific binding of a GST-fusion protein to a polymeric bead containing glutathione. For example, GST-Ephexin5 is bound to glutathione-Sepharose beads. The immobilized peptide is then contacted with the test compound.

As used herein, the term "test compound" refers to compounds and/or compositions that are to be screened for their ability to inhibit Ephexin5. Test compounds may include a wide variety of different compounds, including chemical compounds, mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the test compound is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular mass equal to or less than 700 Daltons.

The number of possible test compounds runs into millions. Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, graffinity, Panvera, Vitas-M Lab, Biomol International and Oxford. These libraries can be screened using the screening devices and methods described herein. Chemical compound libraries such as those from NIH Roadmap, Molecular Libraries Screening Centers Network (MLSCN) can also be used. A comprehensive list of compound libraries can be found at http://www.broad.harvard-.edu/chembio/platform/screening/compound_libraries/index.htm. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

Depending upon the particular embodiment being practiced, the test compounds may be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

Generally, compounds can be tested at any concentration that can inhibit and/or decrease RhoA activation over an appropriate time period. In some embodiments, compounds are tested at a concentration in the range of from about 0.1 nM to about 1000 mM. Preferably the compound is tested in the range of from about 0.1 µM to about 10 µM.

Additionally, the test compound can be contacted with the Ephexin5 for a sufficient time to allow the test compound to interact with Ephexin5. For a non-limiting example, Ephexin5 is incubated with the test compound for at least 15 minutes before assaying Rho GEF activity.

In some embodiments, screening assay further comprises selecting the compound that inhibits or reduces Rho GEF activity of Ephexin5. The test compound can inhibit Rho GEF activity of Ephexin5 by at least 10%, 20%, 30%, 40%, 50%, 50%, 70%, 80%, 90%, 95% or more relative to a control.

In some embodiments, the screening method is a high-throughput screening. High-throughput screening (HTS) is a method for scientific experimentation that uses robotics, data processing and control software, liquid handling devices, and sensitive detectors. High-Throughput Screening or HTS allows a researcher to quickly conduct millions of biochemical, genetic or pharmacological tests. High-Throughput Screening are well known to one skilled in the art, for example, those described in U.S. Pat. Nos. 5,976,813; 6,472,144; 6,692,856; 6,824,982; and 7,091,048, and contents of each of which is herein incorporated by reference in its entirety.

HTS uses automation to run a screen of an assay against a library of candidate compounds. An assay is a test for specific activity: usually inhibition or stimulation of a biochemical or biological mechanism. Typical HTS screening libraries or "decks" can contain from 100,000 to more than 2,000,000 compounds.

The key labware or testing vessel of HTS is the microtiter plate: a small container, usually disposable and made of plastic, that features a grid of small, open divots called wells. Modern microplates for HTS generally have either 384, 1536, or 3456 wells. These are all multiples of 96, reflecting the original 96 well microplate with 8×12 9 mm spaced wells.

To prepare for an assay, the researcher fills each well of the plate with the appropriate reagents that he or she wishes to conduct the experiment with, such as Ephexin5. After some incubation time has passed to allow the reagent to absorb, bind to, or otherwise react (or fail to react) with the compounds in the wells, measurements are taken across all the plate's wells, either manually or by a machine. Manual measurements are often necessary when the researcher is using microscopy to (for example) seek changes that a computer could not easily determine by itself. Otherwise, a specialized automated analysis machine can run a number of experiments on the wells such as colorimetric measurements, radioactivity counting, etc. In this case, the machine outputs the result of each experiment as a grid of numeric values, with each number mapping to the value obtained from a single well. A high-capacity analysis machine can measure dozens of plates in the space of a few minutes like this, generating thousands of experimental data points very quickly.

In another aspect, the invention provides a compound selected by the screening assay described herein. It is to be understood that analogs, derivatives, and isomers of the compounds selected by the screening assays described herein are also claimed herein.

Method of Increasing Synapse Numbers

In another aspect, the invention provides a method for increasing spine/excitatory synapse formation and/or numbers, the method comprising contacting a cell with an Ephexin5 inhibitor. In some embodiments, the cell is a neuronal cell.

The term "contacting" or "contact" as used herein in connection with contacting a cell includes subjecting the cell to an appropriate culture media which comprises the indicated Ephexin5 inhibitor. Where the cell is in vivo, "contacting" or "contact" includes administering the Ephexin5 inhibitor in a pharmaceutical composition to a subject via an appropriate administration route such that the Epehxin5 inhibitor contacts the cell in vivo.

For in vivo methods, a therapeutically effective amount of an Ephexin5 inhibitor modulator can be administered to a subject. Methods of administering compounds to a subject are known in the art and easily available to one of skill in the art.

As described herein, inhibiting Ephexin5 can lead to an increase in spine/excitatory synapse formation and/or numbers. Accordingly, inhibition of Ephexin5 in a subject can lead to treatment, prevention or amelioration of a number of conditions and/or disorders associated with decreased spine/excitatory synapse formation and/or numbers.

Without limitations, the Ephexin5 inhibitor can inhibit Ephexin5 by a number of different ways. For example, the inhibitor can decrease the amount of Ephexin5 present and/or inhibit Ephexin5 activity without decreasing the amount of Ephexin5 present. Furthermore, Ephexin5 inhibitor can be a small organic or inorganic molecule, a peptides, a protein, a peptide analog or derivative, a nucleic acid, a nucleic acid analog or derivative, an antibody, or fragment of an antibody. In some embodiments, the Ephexin5 inhibitor is a compound selected by a screening assay described herein.

In some embodiments, the Ephexin5 inhibitor is a siRNA or shRNA comprising a nucleotide sequence selected from the group consisting of TAGCCGCCTTATGGATACAAA (SEQ ID NO:11, Ephexin5 shRNA 5"), CCCTGCAGGAC-GAACCTTTAT (SEQ ID NO: 12, Ephexin5 shRNA 6"), and TCCGAAAGCACTTCCTCAAAT (SEQ ID NO: 13, Ephexin5 shRNA 7").

For administration to a subject, the Ephexin5 inhibitor can be provided in pharmaceutically acceptable compositions. These pharmaceutically acceptable compositions comprise an Ephexin5 inhibitor, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising an aggregate which is effective for producing some desired therapeutic effect in at least a sub-population of cells in an animal at a reasonable benefit/risk ratio applicable to any medical treatment. For example, an amount of an Ephexin5 inhibitor administered to a subject that is sufficient to produce a statistically significant, measurable inhibition of Rho GEF activity of Ephexin5.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more of the composition being delivered to a specific location as compared to the entire body of the subject, whereas, systemic administration results in delivery to essentially the entire body of the subject.

An Ephexin5 inhibitor can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments of the aspects described herein, the compositions are administered by intravenous infusion or injection.

As used herein, a "subject" means a human or animal. Examples of subjects include primates (e.g., humans, and monkeys). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of conditions or disorders associated with decreased spine/excitatory synapse formation and/or numbers. In addition, the methods and compositions described herein can be used to treat domesticated animals and/or pets.

A subject can be one who has been previously diagnosed with or identified as suffering from or having a disease or disorder characterized by decreased spine/excitatory synapse formation and/or numbers.

A subject can be one who has been previously diagnosed with or identified as suffering from or having an Autism Spectrum Disorder.

In some embodiments, the subject is previously diagnosed with or identified as suffering from or having Angelman syndrome.

In some embodiments, the method further comprising diagnosing a subject for a disease or disorder characterized by decreased spine/excitatory synapse formation and/or numbers before onset of treatment with a method described herein.

The amount of an Ephexin5 inhibitor that can be combined with a carrier material to produce a single dosage form will generally be that amount of the compound that produces a therapeutic effect. Generally out of one hundred percent, this amount will range from about 0.01% to 99% of the compound, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that an Ephexin5 inhibitor is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that Ephexin5 inhibitor or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the Ephexin5 inhibitor. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The Ephexin5 inhibitor can be administrated to a subject in combination with one or more pharmaceutically active agents. Exemplary pharmaceutically active compound include, but are not limited to, those found in *Harrison's Principles of Internal Medicine*, 13th Edition, Eds. T. R. Harrison et al. McGraw-Hill N.Y., N.Y.; Physicians Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

The Ephexin5 inhibitor and the pharmaceutically active agent can be administrated to the subject in the same pharmaceutical composition or in different pharmaceutical compositions (at the same time or at different times). When administrated at different times, the Ephexin5 inhibitor and the pharmaceutically active agent can be administered within 5 minutes, 10 minutes, 20 minutes, 60 minutes, 2 hours, 3 hours, 4, hours, 8 hours, 12 hours, 24 hours of administration of the other. When the Ephexin5 inhibitor and the pharmaceutically active agent are administered in different pharmaceutical compositions, routes of administration can be different.

In yet another aspect the invention provide an anti-Ephexin5 antibody. In some embodiments, the antibody binds to a peptide comprising the amino acids 1-418 of mouse Ephexin5. In some embodiments, the antibody binds to an epitope within residues 1-418 of the mouse Ephexin5 amino acid sequence.

In one embodiment, amino acid sequence of Ephexin5 is PTLKPPRIIRPRPPSRHRAPHSPGPLH-NGSSPKALPQISNDASASVCTSIFWEPPTASLKP PALL-PPSVSRTSLDSQTSPDSPSSTPSPSPVS-RRSISPEPAPCSPVPPPKPSGSSRTPLPSG PTPLQDGSASAPGTVRRLAGKFEWGAE-GKAQSSDSLERCSQGSTEVNGEKETPEAAL SGNG-SQENGTPDAALACPPCCPCVCHVAKP-GLELRWVPVGSSEDILRIPCRASPLRAS RSRINPPVISHPPVVLTSYRSTAERKLL-PPLKPPKPTKVRQDISTSEELPQPDLKLPSED GIQTAT-KAWEGDRPEGAPLNAPPVALEGREEE-GLDGLKGLQWELPLQDEPLYQTYR AAVLSEELWGVGEDGGPSPANPGEAPTF-SRLPGPRNTLWQELPAVRGSGLLES (SEQ ID NO: 18).

In some embodiments, the antibody binds to a peptide comprising the amino acid sequence EHERRKHLRQHUK (SEQ ID NO: 19), corresponding to amino acids 720-732 of mouse Ephexin5. In some embodiments, the antibody binds to an epitope within residues 720-732 of the mouse Ephexin5 amino acid sequence.

In some embodiments, the antibody binds to a peptide comprising the amino acid sequence PLQDEPL(pY)QTYRAAV (SEQ ID NO: 20), wherein in pY is a phosphorylated tyrosine, corresponding to amino acids 354-368 of mouse Ephexin5. In some embodiments, the antibody binds to an epitope within the amino acid sequence PLQDEPL(pY)QTYRAAV (SEQ ID NO: 20), wherein pY is a phosphorylated tyrosine.

The term "antibody" refers to immunoglobulin molecules and immunologically active portions of immunoglobulin molecules (molecules that contain an antigen binding site which specifically binds an antigen), including monoclonal antibodies (including full length monoclonal antibodies), polyclonal antibodies, multispecific antibodies (for example, bispecific antibodies), chimeric antibodies, CDR-grafted antibodies, humanized antibodies, human antibodies, and single chain antibodies (scFvs). The term "antibody" may also include but is not limited to types of antibodies such as IgA, IgD, IgE, IgG and/or IgM, and/or the subtypes IgG1, IgG2, IgG3, IgG4, IgA1 and/or IgA2.

The term "monoclonal antibody" or "monoclonal antibody composition", as used herein, refers to a population of antibody molecules that contain only one species of an antigen binding site capable of recognizing and binding to a particular epitope of a target antigen, for example, an epitope(s) of Ephexin5. A monoclonal antibody composition thus typically displays a single binding specificity and affinity for a particular target antigen with which it immunoreacts.

The term "single-chain antibody" refers to a protein having a two-polypeptide chain structure consisting of a heavy and a light chain, said chains being stabilized, for example, by interchain peptide linkers, which has the ability to specifically bind antigen. Techniques for producing single chain antibodies specific to target antigen are described, for example, in U.S. Pat. No. 4,946,778.

The term "antibody fragment" includes F(ab')2 fragments, Fab fragments, Fab' fragments, Fd fragments, Fv fragments, and single domain antibody fragments (DAbs). Immunologically active portions of immunoglobulins include, for example, F(ab) and F(ab')2 fragments. Methods for the construction of Fab fragments are described, for example, Huse, et al. (1989) 45 Science 246:1275 1281). Other antibody fragments may be produced by techniques known in the art including, but not limited to: (i) an F(ab')2 fragment produced by pepsin digestion of an antibody molecule; (ii) a Fab fragment generated by reducing the disulfide bridges of an F(ab')2 fragment; (iii) a Fab' fragment generated by the treatment of the antibody molecule with papain and a reducing agent and (iv) Fv fragments. Various fragments can also be produced by art-recognized recombinant engineering techniques. Non-human antibodies can be "humanized" by techniques described, for example, in U.S. Pat. No. 5,225,539. In one method, the non-human CDRs are inserted into a human antibody or consensus antibody framework sequence.

Kits

In yet another aspect, the invention provides a kit for screening compounds and compositions useful as Ephexin5 inhibitors, the kit comprising at least one of the following: a peptide comprising the amino acid sequence of Ephexin5 or a conservative variant thereof; a nucleotide encoding a peptide comprising the amino acid sequence of Ephexin5 or a conservative variant thereof; or a cell comprising a polynucleotide encoding a peptide comprising the amino acid sequence of Ephexin5 or a conservative variant thereof.

The kit can also comprise reagents for carrying out the screening assay, e.g., reagents and/or buffers for determining RhoA activation. Exemplary reagents for determining RhoA activation include, but are not limited to, RhoA or a conservative variant thereof, GTP, protein comprising a binding domain for activated RhoA, and anti-RhoA antibodies.

In addition to the above described components, the kit can include informational material. The informational material can be descriptive, instructional, marketing or other material that relates to the methods described herein and/or the use of the compound for the methods described herein. For example, the informational material describes methods for screening a compound for Ephexin5 inhibition.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the kit components and/or its use in the methods described herein. Of course, the informational material can also be provided in any combination of formats.

In some embodiments the individual components of the kit can be provided in one container. Alternatively, it can be desirable to provide the components of the kit separately in two or more containers, e.g., one container for Ephexin5 and at least another for reagents and/or buffers for determining RhoA activation.

The components of the kit can be provided in any form, e.g., liquid, dried or lyophilized form. When the formulation is provided as a dried form, reconstitution generally is by the addition of a suitable solvent. The solvent, e.g., sterile water or buffer, can optionally be provided in the kit.

DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

By "treatment", "prevention" or "amelioration" of a condition, disease and/or disorder associated with reduced spine/excitatory synapse formation and/or numbers is meant delaying or preventing the onset, reversing, alleviating, ameliorating, inhibiting, slowing down or stopping the progression, aggravation or deterioration the progression or severity of a condition, disease and/or disorder associated with reduced spine/excitatory synapse formation and/or numbers. In some embodiments, at least one symptom associated with a condition, disease and/or disorder associated with reduced spine/excitatory synapse formation and/or numbers is alleviated by at least 5%, at least 10%, at least 20%, at least 30%, at least 40%, or at least 50% relative to before onset of treatment.

In some embodiments, the number of spine/excitatory synapse is increased by at least 5%, at least 10%, at least 20%, at least 30%, at least 40%, or at least 50% relative to before onset of treatment.

As used herein, the term "neuronal cell" refers to a cell that is a morphologic and functional unit of the nervous system. The cell comprises a nerve cell body, the dendrites, and the axon. The terms neuron, nerve cell, neuronal, neurone, and neurocyte can be used interchangeably. Neuronal cell types can include, but are not limited to a typical nerve cell body showing internal structure, a horizontal cell (of Cajal) from cerebral cortex; Martinottic cell, biopolar cell, unipolar cell, Pukinje cell, and a pyramidal cell of motor area of cerebral cortex. Furthermore, the cell can express the Ephexin5 from an endogenous gene or from a vector transfected into the cell.

As used herein, the term "peptide" is used in its broadest sense to refer to compounds containing amino acids, amino acid equivalents or other non-amino groups, while still retaining the desired functional activity of a peptide. Peptide equivalents can differ from conventional peptides by the replacement of one or more amino acids with related organic acids (such as PABA), amino acids or the like or the substitution or modification of side chains or functional groups. The peptides can be linear or cyclic. A peptide can be modified to include one or more of D-amino acids, beta-amino acids, chemically modified amino acids, naturally occurring non-proteogenic amino acids, rare amino acids, and chemically synthesized compounds that have properties known in the art to be characteristic of an amino acid. As used herein, the term "proteogenic" indicates that the amino acid can be incorporated into a protein in a cell through well-known metabolic pathways.

The term "peptide bond" means a covalent amide linkage formed by loss of a molecule of water between the carboxyl group of one amino acid and the amino group of a second amino acid. Exemplary peptide bond replacements include, but are not limited to, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group. In some embodiments, the peptide comprises at least one peptide bond replacement.

As used herein, a "conservative variant" is an amino acid sequence in which a first amino acid is replaced by a second amino acid or amino acid analog having at least one similar biochemical property, which can be, for example, similar size, charge, hydrophobicity or hydrogen bonding capacity. For example, a first hydrophobic amino acid can be conservatively substituted with a second (non-identical) hydrophobic amino acid such as alanine, valine, leucine, or isoleucine, or an analog thereof. Similarly, a first basic amino acid can be conservatively substituted with a second (non-identical) basic amino acid such as arginine or lysine, or an analog thereof. In the same way, a first acidic amino acid can be conservatively substituted with a second (non-identical) acidic amino acid such as aspartic acid or glutamic acid, or an analog thereof or an aromatic amino acid such as phenylalanine can be conservatively substituted with a second aromatic amino acid or amino acid analog, for example tyrosine.

As used herein, the term "nucleic acid" or "oligonucleotide" or grammatical equivalents herein means at least two nucleotides, including analogs or derivatives thereof, that are covalently linked together. Exemplary oligonucleotides include, but are not limited to, single-stranded and double-stranded siRNAs and other RNA interference reagents (RNAi agents or iRNA agents), shRNA (short hairpin RNAs), antisense oligonucleotides, aptamers, ribozymes, and microRNAs (miRNAs). The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. The nucleic acids can comprise one or more backbone modifications, e.g., phosphoramide (Beaucage et al., Tetrahedron 49(10):1925 (1993) and references therein; Letsinger, J. Org. Chem. 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); and Nielsen, Nature, 365:566 (1993), content of all of which is herein incorporated by reference. The nucleic acids can also include modifications to nucleobase and/or sugar moieties of nucleotides. Examplary sugar modifications at the sugar moiety include replacement of 2'-OH with halogens (e.g., fluoro), O-mehtyl, O-methoxyethyl, $NH_2$, SH and S-methyl.

As used herein, the term "polysaccharide" refers to macromolecular carbohydrates whose molecule consists of a large number of monosaccharide molecules which are joined to one another by glycosidic linkage. The term polysaccharide is also intended to embrace an oligosaccharide. The polysaccharide can be homopolysaccharides or heteropolysaccharides. Whereas the homopolysaccharides contain only one kind of unit, the heteropolysaccharides consist of monomer units of different kinds.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "analog" as used herein refers to a compound that results from substitution, replacement or deletion of various organic groups or hydrogen atoms from a parent compound. As such, some monoterpenoids can be considered to be analogs of monoterpenes, or in some cases, analogs of other monoterpenoids, including derivatives of monoterpenes. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

The invention can also be described by one or more of the numbered paragraphs:

1. A method for determining activators of spine/excitatory synapse formation, comprising contacting Ephexin5 with a test compound and selecting the compound that inhibits Ephexin5 RhoA GEF activity.
2. The method of paragraph 1, wherein Ephexin5 RhoA GEF activity is determined by assaying RhoA activation and selecting the test compound that decreases RhoA activation relative to a control.
3. The method of paragraph 2, wherein RhoA activation is determined by binding of GTP to RhoA.
4. The method of any of paragraphs 2-3, wherein RhoA activation is determined by assaying the GTPase activity of RhoA.
5. The method of any of paragraphs 2-4, wherein RhoA activation is determined by assaying binding of a protein to RhoA, which protein preferentially binds to activated RhoA.
6. The method of paragraph 5, wherein said assaying is by immuno-staining.
7. The method of any of paragraphs 5-6, wherein the protein comprises a Rhotekin-Binding Domain (RBD).
8. The method of any of paragraphs 5-7, wherein the protein is a fusion protein.
9. The method of any of paragraphs 5-8, wherein the protein is a GST-fusion protein comprising a Rhotekin-Binding Domain.
10. The method of any of paragraphs 1-9, wherein the Ephexin5 comprises an amino acid sequence or a conservative variant thereof encoded by a polynucleotide sequence selected from the group consisting of NCBI Sequence Reference Nos. and/or identifier Rho guanine nucleotide exchange factor (GEF) 15, ARGEF15, KIAA0915, F1113791, Vsm-RhoGEF, Rho guanine exchange factor (GEF) 15, MGC44868, rho guanine nucleotide exchange factor 15, 155901, 228992, ENSG000001988447, O949893, GC17P008591, GC17P009307, GC17P008156, GC17P008414, MGC102247, MGC144141, MGC144142, D130071N09, D530030K12Rik, RP23-396M19.6, NM_173728, NM_025014, and Arhgef15.
11. The method of any of paragraphs 1-10, wherein the Ephexin5 is purified from a cell expressing the Ephexin5.
12. The method of paragraph 11, wherein the cell is a neuronal cell.
13. The method of paragraph 11, wherein the cell is a non-neuronal cell.
14. The method of paragraph 11, wherein the cell is a HEK293T cell.
15. The method of any of paragraphs 11-14, wherein the Ephexin5 is expressed from an endogenous gene in the cell.
16. The method of any of paragraphs 11-14, wherein the Ephexin5 is expressed from a vector transfected in the cell.

17. The method of any of paragraphs 1-16, wherein the Ephexin5 is chemically synthesized.
18. The method of any of paragraphs 1-17, wherein the test compound is selected from the group consisting of small organic or inorganic molecules; peptides; proteins; peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof.
19. The method of paragraph 18, wherein the test compound has a molecular weight of less than 5000 Daltons (5 kD).
20. The method of any of paragraphs 1-19, wherein the test compound is tested at a concentration in the range of about 0.1 nM to about 1000 mM.
21. The method of any of paragraphs 1-20, wherein the method is a high-throughput screening method.
22. A compound selected by the method of any of paragraphs 1-21 and analogs, isomers and derivatives thereof.
23. A method of promoting spine/excitatory synapse formation, the method comprising contacting a neuron with an Ephexin5 inhibitor selected by the method of any of paragraphs 1-21.
24. A method of promoting spine/excitatory synapse formation, the method comprising contacting a neuron with an Ephexin5 inhibitor.
25. The method of paragraph 24, wherein the Ephexin5 inhibitor inhibits the RhoA GEF activity of Ephexin5 and/or decreases the level of Ephexin5.
26. The method of paragraph any of paragraphs 23-25, wherein the Ephexin5 inhibitor is selected from the group consisting of small organic or inorganic molecules, peptides, proteins, peptide analogs, nucleic acids, nucleic acid analogs, antibodies, and antibody fragments.
27. The method of any of paragraphs 23-26, wherein the Ephexin5 inhibitor has a molecular weight of less than 5000 Daltons (5 kD).
28. The method of any of paragraphs 23-27, wherein the nucleic acid is an antisense oligonucleotide, an aptamer, a siRNA, a shRNA, or a ribozyme.
29. The method of any of paragraphs 23-28, wherein the Ephexin5 inhibitor is a shRNA comprising a nucleotide sequence selected from the group consisting of TAGCCGCCTTATGGATACAAA (SEQ ID NO: 11, Ephexin5 shRNA 5"), CCCTGCAGGACGAACCTTTAT (SEQ ID NO: 12, Ephexin5 shRNA 6"), and TCCGAAAGCACTTCCTCAAAT (SEQ ID NO: 13, Ephexin5 shRNA 7").
30. The method of any of paragraphs 23-29, wherein said contacting is in vitro.
31. The method of any of paragraphs 23-30 wherein said contacting is in vivo.
32. The method of paragraph 30, wherein in vivo contacting is in a mammal.
33. The method of any of paragraphs 31-32, wherein said in vivo contacting is in a rodent.
34. The method of any of paragraphs 31-32, wherein said in vivo contacting is in a human.
35. The method of any of paragraphs 31-34, wherein said in vivo contacting is in a subject, which subject suffers from or has a neurological disorder characterized by decreased spine/excitatory synapse formation and/or decreased spine/excitatory synapse numbers.
36. The method of any of paragraphs 31-35, wherein said in vivo contact is in a subject, which subject suffers from or is diagnosed with an Autism Spectrum Disorder.
37. The method of any of paragraphs 31-36, wherein said in vivo contacting is in subject, which subject suffers from or is diagnosed with Angelman syndrome.
38. A kit for screening compounds and compositions useful as Ephexin5 inhibitors, the kit comprising at least one of the following: a peptide comprising an amino acid sequence of Ephexin5 or a conservative variant thereof; a nucleotide encoding a peptide comprising an amino acid sequence of Ephexin5 or a conservative variant thereof; or a cell comprising a polynucleotide encoding a peptide comprising an amino acid sequence of Ephexin5 or a conservative variant thereof.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Materials and Methods

Figure 9:
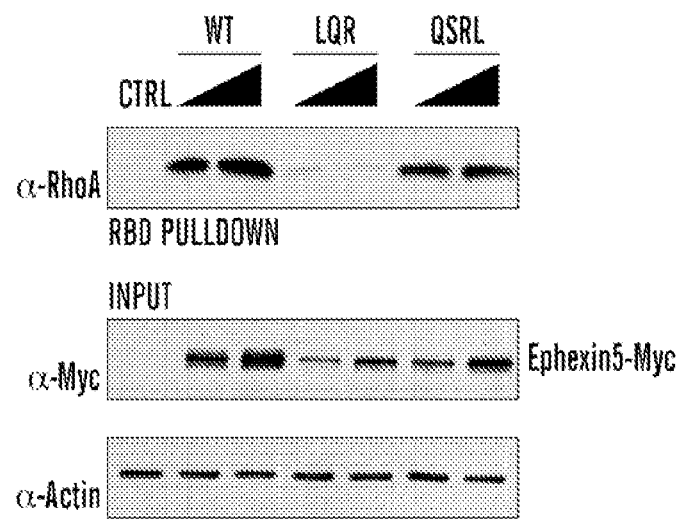
FIG. 9 shows the Ephexin5 QSRL mutant. Lysates from HEK293T cells transfected with empty vector, Ephexin5-Myc (WT), Ephexin5LQR-Myc (LQR), or Ephexin5-QSRL-Myc (QSRL) were assayed for activated RhoA using RBD pulldown assay as described in FIG. 2. Total protein levels were assessed by immunoblotting for Ephexin-Myc and $\beta$-Actin (Input panels).

DNA Constructs:

The full-length mouse Ephexin5, NCBI Reference Seq. No. NM_177566, was generated by RT-PCR from RNA isolated from mouse E16 cortical neurons at 7 days in vitro and subcloned into EcoRI/XhoI sites of the pEF1-Myc-HisA vector (Invitrogen). Ephexin5 GEF and phosphorylation mutants (LQR, QSRL, and Y361F) were generated using the QuickChange site-directed mutagenesis kit (Stratagene). All constructs were verified by DNA sequencing. The following plasmid constructs have been described previously: Flag-EphB2, Flag-EphB2KD, Flag-EphB2.Cyto (Dalva et al., 2000), Ephexin1-Myc (Sahin et al., 2005), HA-Ube3A (Greer et al, 2010), HA-Mef2 (Flavell et al., 2006), HA-Cbl-b (Cowan et al., 2005), eGFP (Paradis et al., 2007), Cre-recombinase (Lin et al., 2008). The pLenti-Lox-Ephexin5 RNAi constructs were designed as previously described. (Line et al, 2008). Briefly, the following oligonucleotides were annealed with their complimentary sequence and inserted into the BglII site of pLenti-Lox vector: TAGCCGCCTTATGGATACAAA (SEQ ID NO: 11) and TCCGAAAGCACTTCCTCAAAT (SEQ ID NO: 13) (FIG. 9). These regions were not homologous to Ephexin1 or any other known genes as indicated by Blast search.

Generation of Ephexin5$^{-/-}$ Mice:

An Ephexin5 targeting vector was electroporated into 129 J1 ES cells, and positive clones were identified by Southern hybridization with two separate probes. To obtain constitutive deletion of the ephexin5 exons, a Cre-recombinase expressing plasmid (pOG231Cre or pMC-CreN) was electroporated into ES cells carrying the homologous recombination. Constitutive knockout and conditional floxed ES cells were identified by replicate plating for G418 sensitivity followed by Southern hybridization and genomic PCR. Positive clones were grown without G418 and expanded for genotyping.

Antibodies:

The following rabbit polyclonal antibodies were generated against the indicated amino acids of mouse Ephexin5 and then affinity purified: anti-N-Ephexin5 (α-N-E5) was raised against a GST-fusion protein containing amino acids 1-418. Anti-C-Ephexin5 (α-C-ES) was raised against a C-terminal peptide sequence corresponding to amino acids 720-732 (EHERRKHLRQHUK, SEQ ID NO: 19). AntiEphexin5 phosphoY361 (α-p361) was raised against a peptide sequence corresponding to amino acids 354-368 (PLQDEPL (pY)QTYRAAV, SEQ ID NO: 20), in which tyrosine residue 361 was phosphorylated (denoted as pY in peptide sequence). The specificity of the Ephexin5 antibodies was tested by western blotting using brain lysates from WT and Ephexin5 knockout littermates. Rabbit polyclonal anti-EphB2 (α-EphB2) and anti-phospho-Eph (α-pEph) were used as previously described (Dalva et al., 2000). The following antibodies are commercially available and used according to manufacturer's suggestions for western blotting, immunocytochemistry and immunoprecipitations: anti-Myc (Abcam), anti-Flag (Sigma), anti-RhoA (Santa Cruz Biotechnology), goat anti-EphB2 (Santa Cruz), anti-Rac1 (Millipore), anti-Cdc42 (Millipore), anti-β-actin (Abcam), anti-PSD95 (ABR Affinity Bioreagents), anti-Synapsin (Chemicon), anti-HA (Santa Cruz Biotechnology), anti-pan-phosphotyrosine 4G10 (Millipore), anti-ubiquitin (Biomol International), and anti-E6AP (Ube3A) (Biomol).

Mice, Cell Culture, Transfections, and Ephrin Stimulations:

Ube3a knockout mice were obtained from The Jackson Laboratory, strain 129-Ube3a$^{tm1Alb}$/J, from stock number 004477. HEK293T cells were cultured in DMEM supplemented with 10% fetal bovine serum, 2 mM glutamine (Sigma), and penicillin/streptomycin (100 U/mL and 100 μg/mL, respectively; Sigma). Rat hippocampal neurons were prepared from E18 Long-Evans rat embryos (Charles River) as previously described (Xia et al., 1996). Mouse hippocampal neurons were prepared from E16 C57/B6 mouse embryos as previously described (Tolias et al., 2005). Hippocampal neurons were maintained in Neurobasal Medium (Invitrogen) supplemented with 2% B27 (Invitrogen), penicillin/streptomycin (100 U/mL and 100 μg/mL, respectively), and 2 mM glutamine. For synapse assays using immunofluorescence staining, hippocampal neurons were plated on glia isolated as previously described (Flavell et al., 2006). Organotypic hippocampal slice cultures were prepared from P6 Ephexin5 conditional mice as previously described (Stoppini et al., 1991). Slices were biolistically transfected with a Helios Gene Gun (Biorad) after 2 days. Bullets for the gene gun were 1.6-μm gold particles coated with 15 μg eGFP and 30 μg Cre. Empty vector plasmid was added to bring the total DNA to 60 μg in each case. Cultures were fixed, stained, and quantified for spine number at DIV6. HEK293T cells were transfected for 24 or 48 hours using the calcium phosphate method as previously described (Lois et al., 2002). Dissociated neurons were transfected using the Lipofectamine method (Invitrogen) according to the manufacturer's suggestions. For Ephrin stimulations in dissociated cultured neurons, mouse EphrinB1-FC (1 μg/μL; R & D Systems) was pre-clustered with goat anti-human IgG FC (1.3 μg/μL; Jackson Immunoresearch) at room temperature in 1×PBS in a 1:3 ratio prior to stimulation. Pre-clustered EphrinB1-FC was added to Neurobasal/B27 medium at 5 μg/mL and applied to cultured neurons. For controls, clustered goat anti-human IgG FC in Neurobasal/B27 was applied to neurons.

Cell Lysis, Immunoprecipitations, GEF Pulldown Assays and Western Blots:

Whole rat or mouse brains or cultured cells were collected and homogenized in RIPA buffer (50 mM Tris pH 8.0, 150 mM NaCl, 1% Triton X-100, 0.5% Sodium Deoxycholate, 0.1% SDS, 5 mM EDTA, 10 mM NaF, complete protease inhibitor cocktail tablet (Roche), 1 mM sodium orthovanadate, 1 mM β-glycerophosphate). For time course studies, hippocampus was freshly dissected out of whole brain and homogenized as described above. For immunoprecipitations, cells were lysed in RIPA buffer and centrifuged at 50,000×g. Supernatants were incubated with appropriate antibody (1-3 μg) for 2 hours at 4° C., followed by addition of Protein-A or Protein-G beads (Santa Cruz Biotechnology) for 1 hour, and washed three times with ice-cold RIPA buffer. For the phosphotyrosine detection experiment in HEK293T cells, samples were boiled for 10 minutes in 1% SDS buffer to disrupt the Ephexin5/EphB2 interaction and diluted 1:5 in 1.25×RIPA buffer prior to immunoprecipitation of Ephexin5-Myc. RBD and PBD pulldown assays were conducted according to the manufacture's suggestions (Upstate Cell Signaling Solutions). Briefly, HEK293T cells were grown to ~60% confluence, transfected with plasmids for 48 hours, lysed in Mg2+/lysis buffer (25 mM HEPES pH 7.5, 125 mM NaCl, 1% NP-40, 10 mM MgCl2, 1 mM EDTA, and 10% glycerol supplemented with complete protease inhibitor tablets from Roche), and incubated with either RBD or PBD agarose for 45 minutes at 4 degrees. For western blots, samples were boiled for 5 minutes in SDS sample buffer, resolved by SDS PAGE, transferred to nitrocellulose, and immunoblotted.

In Situ Hybridization:

To generate probes for in situ hybridization, mouse Ephexin5 and EphB2 cDNA were subcloned into pBluescript II SK (+). Bluescript plasmids containing Ephexin5 or EphB2 cDNA were linearized using the restriction enzyme BssHII. Sense and antisense probes were generated using DIG RNA labeling mix (Roche) according to manufacturer's instructions. Full-length DIG-labeled probes were subjected to alkaline hydrolysis as previously described (Wiemers and Gerfin-Moser, 1993). Probe sizes were checked by running non-hydrolyzed and hydrolyzed probes on a 1% formaldehyde agarose gel. In situ hybridization was performed as previously described (Schaeren-Wiemers and Gerfin-Moser, 1993). Briefly, P10 whole brains were embedded in Tissue-Tec and kept at −20° C. Tissue sections 14 μm-thick were sectioned onto Superfrost Plus Slides (Merck), fixed for 10 minutes with 4% paraformaldehyde in PBS, and subsequently washed 3 times in PBS. Acetylation of tissue sections was performed for 10 minutes with constant stiffing in glass staining jars, and subsequently washed 3× with PBS. Slides were incubated with pre-hybridization solution (50% formamide, 5×SSC, 5×Denhardts solution (Sigma), Yeast tRNA) at room temperature for 6 hours to overnight. DIG-labeled probes were hydrolyzed in an alkaline hydrolysis buffer as previously described (Schaeren-Wiemers and Gerfin-Moser, 1993). Probes were diluted in pre-hybridization buffer at a concentration of 200 ng/mL and denatured for 5 minutes at 85° C. prior to hybridization. Slides were incubated in 100 μL, covered by plastic coverslips (Invitrogen), and hybridization was performed overnight at 72° C. Color reaction was performed as previously described (Schaeren-Wiemers and Gerfin-Moser, 1993), except a BCIP/NBT mixture (Roche) was used according to manufacturer's instructions. Slides were mounted in Slowfade Gold antifade reagent with DAPI (Invitrogen) and covered with Glass Coverslides (Fisher). Sections were imaged using a Zeiss Imager.Z1 microscope with a Photometrics CoolSNAP HQ2 camera on a PLAN APO 63×/1.4 objective.

Immunocytochemistry:

Neurons were fixed for 8 minutes at 25° C. with 4% paraformaldehyde/4% sucrose in PBS. For synapse density measurement, fixed neurons were incubated with anti-PSD-95 and anti-Synapsin antibodies (1:200 each) in 1×GDB (30 mM phosphate buffer [pH 7.4] containing 0.2% gelatin, 0.5% Triton X-100, and 0.8 M NaCl) overnight at 4° C. Goat anti-mouse Cy3 and goat anti-rabbit Cy5 (1:200 each in 1×GDB for 1 hour at 25° C.) antibodies were used to visualize the primary antibodies. For protein co-localization experiments fixed neurons were similarly treated using anti-EphB2 antibodies raised in goat (1:200) and the rabbit anti-N-terminal Ephexin5 antibodies (1:200) or anti-pY361-Ephexin5. For over-expression studies, transfected neurons were fixed and stained as described above using anti-Myc and anti-N-terminal Ephexin5 antibodies to visualize overexpressed Ephexin5 protein in the context of the GFP-labeled neurons to visualize the localization of Ephexin5 protein. Samples on coverslips were mounted on glass slides using Fluoromount-G (Southern Biotech). Neurons were imaged using a laser scanning Zeiss Pascal microscope.

Image Analysis and Quantification:

For dissociated neurons, images were obtained using a Zeiss Pascal confocal microscope, using a 63× objective with sequential acquisition settings at 1024×1024 pixel resolution. Images for the colocalization analysis were taken with the same exposure parameters. On average, 5 stacks at 0.5 µm were taken for each neuron image. Images were collected from 10 to 15 neurons per coverslip, with two coverslips required for each condition. Synapse density was measured using Metamorph software as previously described (Universal Imaging Corporation) (Paradis et al., 2007). Because synapse density and immunostaining vary significantly between experiments, it was necessary to normalize each experiment before combining the data from individual experiments. Normalization and error propagation were performed as previously described (Paradis et al., 2007). The number of overlapping red and blue puncta greater than 2 pixels in size and localized to the transfected neuron was divided by the total dendritic area being measured. For Ephexin5 levels, the total intensity of Ephexin5 puncta over the area of the neuron was used to determine the density of Ephexin5 expression in the neuron. Statistical significance was determined by Student's t test.

For dendritic spine assays, a z series projection of each neuron was made using approximately six sections (0.45 µm/section), each averaged four times. To measure spine density, an experimenter blinded to the condition measured at least three dendritic segments totaling at least 200 µm of dendritic length/neuron, and the number of spines was counted. Between eight and ten transfected neurons were chosen randomly for quantification per experiment, and several pairs of littermates were quantified individually. For quantification of spine size, images blinded to the experimenter were analyzed using Metamorph (Universal Imaging Corporation) by manually tracing the length for at least 1000 spines per animal (Pak et al., 2001). Statistical significance was calculated using Student's t test or ANOVA.

For densitometry measurements we analyzed western blots in the linear range using ImageJ. Each western lane is normalized to loading controls.

Array Tomography:

Array tomography was performed as described previously (Micheva and Smith, 2007). In summary, acute hippocampal slices (300 µm thick) were fixed in 4% paraformaldehyde for 1 hour at room temperature and embedded in LR White resin using the benchtop protocol. Ribbons of between 30-50 serial 100 nm-thick wild type sections prepared from wild type and Ephexin5 mutant mice were mounted side by side on subbed glass coverslips. Coverslips were immunostained with anti-synapsin1 (ms, Chemicon, 1:100) and anti-PSD95 (Rb, ABR Affinity Bioreagents, 1:100) antibodies as described. Serial sections were imaged using a Zeiss Imager.Z1 microscope with a Photometrics CoolSNAP HQ2 camera on a PLAN APO 63×/1.4 objective. Tissue volumes were aligned using ImageJ (NIH) with the multistackreg plugin (Brad Busse). Reconstructed tissue volumes were cropped to include only stratum radiatum of CA1; and, three dimensional models of the synaptic puncta were built using Bitplane Imaris and analyzed using custom software to count synapses. This software computes the distance from the center of every synapsin puncta to the center of every PSD-95 puncta, and a synapse was counted if the distance between the centers was equal to or less than the sum of the radii of the two puncta plus an empirically determined scaling factor of 0.15 µm. All experiments were carried out and analyzed blinded to genotype.

Electrophysiology:

Whole-cell voltage clamp recordings were obtained using an Axopatch 200B amplifier at 25° C. Rat hippocampal neurons were transfected with 250 ng of eGFP and 25 ng of shRNA to Ephexin5 or scrambled shRNA as a control. Four days after transfection, neurons were perfused with artificial cerebrospinal fluid containing 127 mM NaCl, 25 mM $NaHCO_3$, 1.25 mM $Na_2HPO_4$, 2.5 mM KCl, 2 mM $CaCl_2$, 1 mM $MgCl_2$, 25 mM glucose, and saturated with 95% $O_2$, 5% $CO_2$. The internal solution for mEPSC analysis contained 120 mM cesium methane sulfonate, 10 mM HEPES, 4 mM $MgCl_2$, 4 mM $Na_2ATP$, 0.4 mM $Na_2GTP$, 10 mM sodium phosphocreatine and 1 mM EGTA. Osmolarity and pH were adjusted to 300 mOsm and 7.3 with Millipore water and CsOH, respectively.

The mEPSCs were isolated by exposing neurons to 0.5 µM tetrodotoxin, 50 µM picrotoxin (Tocris Bioscience), and 10 µM cyclothiazide. Cells with series resistance larger than 25 MΩ during the recordings were discarded. Data were analyzed in IgorPro (Wavemetrics) using custom-written macros. For each trace, the event threshold was set at 1.5 times the root-meansquare current. Currents were counted as events if they crossed the event threshold, had a rapid rise time (1.5 pA $ms^{-1}$) and had an exponential decay ($\tau$<50 ms for mEPSC).

Statistical significance was determined by two methods. First, 50 random points selected from each cell were concatenated to describe the cumulative distributions of events in each condition and then compared by a Kolmogorov-Smirnov test. Second, a Monte Carlo simulation was performed in which points were randomly sampled from each condition and the mean of these samples compared at least 1,000 times. $P<0.05$ from both tests was considered significant.

Example 1

Ephexin5 Interacts with EphB2

To identify mechanisms that restrict the ability of EphBs to promote an increase in excitatory synapse number, the inventors searched for RhoA guanine nucleotide exchange factors (GEFs) that are predicted to specifically activate RhoA signaling, to be expressed in the same population of neurons that express EphB, to be expressed at the same time during development as EphB, and to interact with EphB. The inventors' previous experiments demonstrated that Ephexin1 is an activator of RhoA that selectively interacts with EphAs but not EphBs (Shamah et al., 2001). The inventors focus their efforts on Ephexin5, the only other Ephexin family member that is highly expressed in the brain (Sahin et al., 2005; Shamah et al., 2001). Structure-function studies of a variety of GEFs have led to the identification of amino acid residues in the activation domain of Rho family GEFs that specifically identify the GEFs as activators of RhoA rather than Rac or Cdc42. Applying this criterion, fourteen GEFs were identified that specifically activate RhoA (Rossman et al., 2005). Of these GEFs, the inventors discovered, by in situ hybridization, that Ephexin5 displayed a similar expression pattern to EphB in developmentally matched CA1 and dentate gyrus regions of the hippocampus (FIG. 1A). These findings raised the possibility that Ephexin5 can mediate the effect of EphB on developing synapses.

Figure 1B:
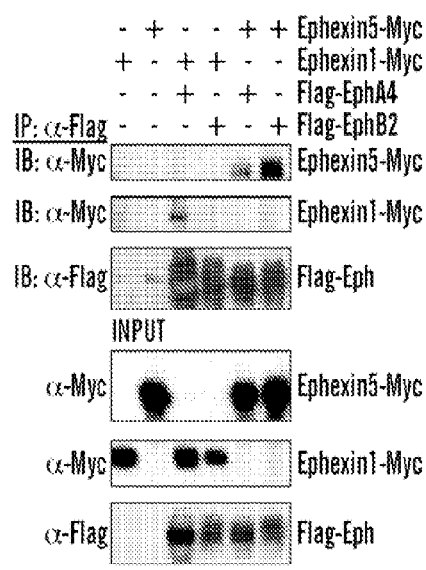

The inventors next tested if Ephexin5 interacts physically with EphB. The inventors transfected HEK293T cells with plasmids encoding Myc-tagged Ephexin5, Ephexin1, or a vector control together with Flag-tagged EphB2 or EphA4 and checked if these proteins co-immunoprecipitate with one another. Twenty-four hours after transfection, extracts were prepared from the HEK293T cells and EphA4 or EphB2 immunoprecipitated with anti-Flag antibodies. The immunoprecipitates were subjected to SDS polyacrylamide gel electrophoresis (SDS-PAGE) and blotted with an anti-Myc antibody. The inventors discovered that Ephexin5 preferentially co-immunoprecipitated with EphB2 but not with EphA4 (FIG. 1B). The relatively weak Ephexin5 interaction with EphA4 was consistent with previously published experiments (Ogita et al., 2003). By contrast, as shown previously, Ephexin1 was co-immunoprecipitated by EphA4 but not EphB2 (Shamah et al., 2001). These findings show that Ephexin5 interacts preferentially with EphB2.

Figure 1C:
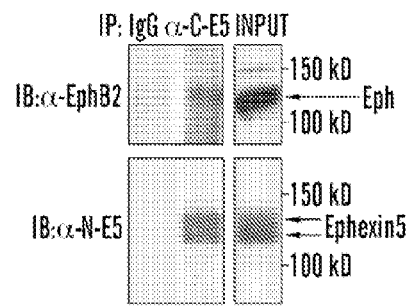
Figure 1D:
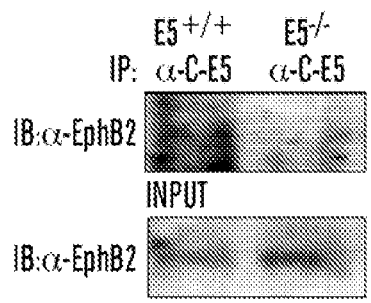

To extend this analysis, the inventors also investigated whether EphB2 interacts with Ephexin5 in neurons. Neurons from embryonic day 16 (E16) mouse brains were lysed in RIPA buffer and the lysates incubated with affinity purified anti-C-terminal Ephexin5 (α-C-E5) or control antibodies (IgG). The immunoprecipitates were then resolved by SDS-PAGE and immunoblotted with affinity purified anti-N-terminal Ephexin5 (α-N-E5) antibodies and antiEphB2 antibodies (FIG. 1C). This analysis revealed that endogenous, neuronal EphB2 was immunoprecipitated by anti-Ephexin5 antibodies but not control antibodies and showed that EphB and Ephexin5 interact. Moreover, using lysates from brains of wild type or Ephexin5 knockout mice (Ephexin5$^{-/-}$ mice) (See FIG. 8 for a description of the generation of Ephexin5$^{-/-}$ mice), the inventors found that their Ephexin5 antibodies immunoprecipitated EphB only from brain lysates when Ephexin5 protein was present (FIG. 1D). Taken together, these findings demonstrate that EphB specifically interacts with Ephexin5 in neurons.

Figure 1E:
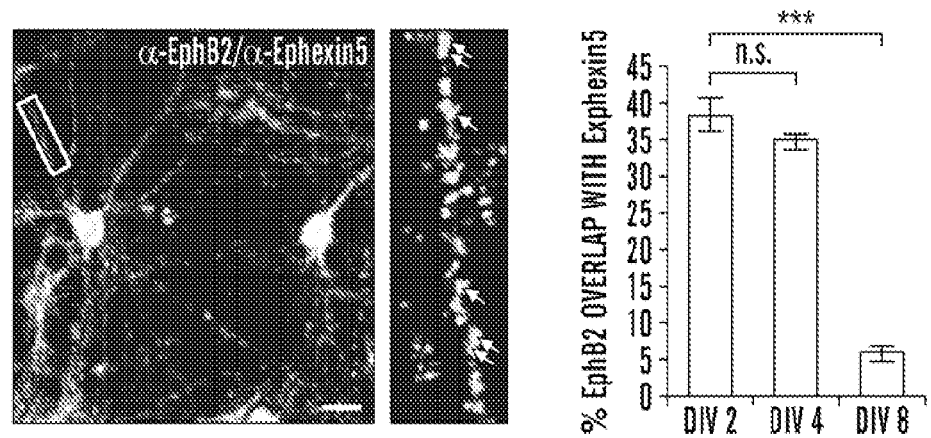

As an independent means of assessing if EphB and Ephexin5 interact with one another, the inventors used immunofluorescence microscopy to determine if these two proteins co-localize in neurons. Cultured mouse hippocampal neurons were transfected with a plasmid expressing green fluorescent protein (GFP). The GFP-expres sing neurons were then imaged and quantified for the co-localization of EphB2 and Ephexin5 puncta by staining with anti-Ephexin5 and anti-EphB2 specific antibodies. This analysis revealed that EphB2 and Ephexin5 colocalize along the dendrite (FIG. 1E). The inventors observed that approximately 40% of EphB staining overlaps with anti-Ephexin5 antibody staining early during the development of excitatory synapses. After eight days in vitro (DIV) the overlap of EphB with Ephexin5 within neuronal dendrites decreased to below the level that would be detected by random chance. This change demonstrates that EphB can interact with Ephexin5 early during development, possibly to inhibit EphB synapse formation. Later during development it appears that EphB and Ephexin5 no longer interact with one another.

Example 2

Ephexin5 is a Guanine Nucleotide Exchange Factor that Activates RhoA Signaling

Figure 2A:
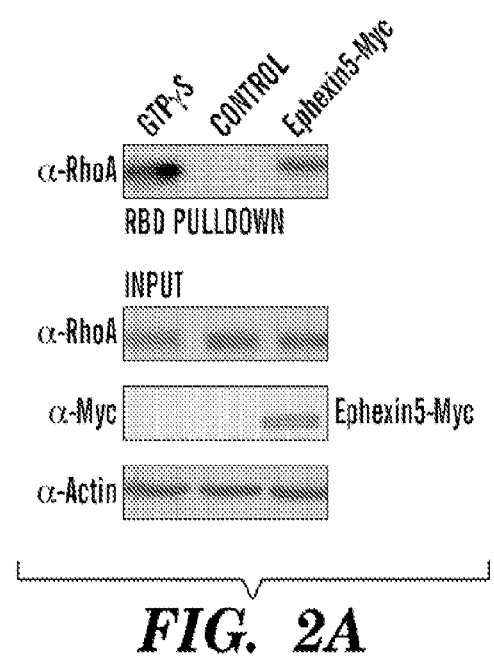
FIG. 2A-2E show that Ephexin5 is a guanine nucleotide exchange factor that activates RhoA signaling.

To determine if Ephexin5 activates RhoA, the inventors transfected HEK293T cells with a control plasmid or a plasmid that drives the expression of Myc-tagged mouse Ephexin5. The inventors then prepared extracts from the transfected cells and incubated the extracts with a GST-fusion protein that includes the Rhotekin-Binding Domain (GST-RBD), a protein domain that selectively interacts with active (GTP-bound) but not inactive (GDP-bound) RhoA. Following SDS-PAGE of the proteins in the extract that bind to GST-RBD, RhoA binding to GST-RBD was measured by immunoblotting with anti-RhoA antibodies. The inventors found that cells expressing Ephexin5 exhibited higher levels of activated RhoA compared to cells transfected with a control plasmid, indicating that Ephexin5 activates RhoA (FIG. 2A).

Figure 2B:
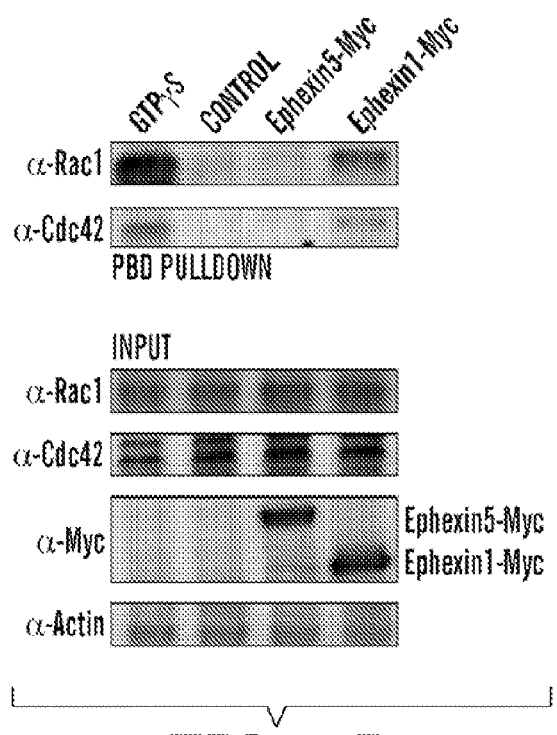

When a similar series of experiments were performed using a GST-fusion Pak-Binding Domain (GST-PBD) which specifically interacts with active forms of two other Rho GTPases, Rac1 and Cdc42, the inventors found that Ephexin5 does not induce the binding of GST-PBD to Rac1 or Cdc42. In contrast, Ephexin1-expressing cells displayed enhanced binding of Rac1 and Cdc42 to GST-PBD. Thus, without wishing to be bound by a theory, Ephexin5 activates RhoA but not Rac1 or Cdc42 (FIG. 2B).

Figure 2C:
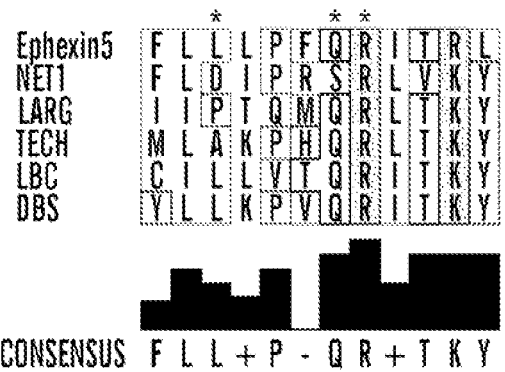
Figure 2D:
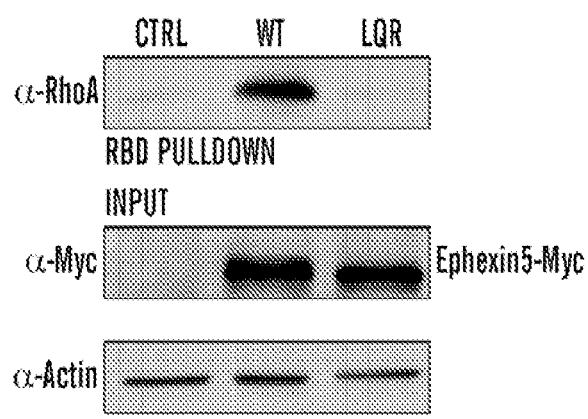

To determine whether Ephexin5 activation of RhoA requires the GEF activity of Ephexin5, the inventors generated a mutant form of Ephexin5 in which its guanine nucleotide exchange activity was impaired. To identify the residues required for Ephexin5 guanine nucleotide exchange activity the inventors compared its Dbl-homology (DH) domain to the DH domain of other RhoA specific GEFs (FIG. 2C) (Snyder et al., 2002). The inventors identified within the α5 helix of Ephexin5's DH domain three amino acids that are conserved in other GEFs that, like Ephexin5, activate RhoA but not Rac1 and Cdc42. To generate a form of Ephexin5 predicted to be inactive as a GEF, the inventors mutated these three conserved amino acids to alanine (i.e., L562, Q566, and R567 (Ephexin5-LQR)). Using the GST-RBD pull down assay the inventors found that although Ephexin5-WT and Ephexin5-LQR were expressed at similar levels, the Ephexin5-LQR mutant was significantly impaired relative to WT in its ability to activate RhoA (FIG. 2D). As a control, the inventors mutated other conserved residues within the α5 DH region to alanine (Q547, 5548, R555, and L556). When the inventors tested this mutant they saw no defect in RhoA activation, indicating that the Ephexin5-LQR mutation specifically disrupts the GEF activity of Ephexin5 and that the inability of the LQR mutant to activate RhoA is not a general consequence of disrupting the α5 region of Ephexin5 (FIG. 9). Taken together, these findings indicate that Ephexin5 requires an intact conserved GEF domain to promote RhoA activity in HEK293T cells, and Ephexin5 functions as a RhoA GEF.

Figure 2E:
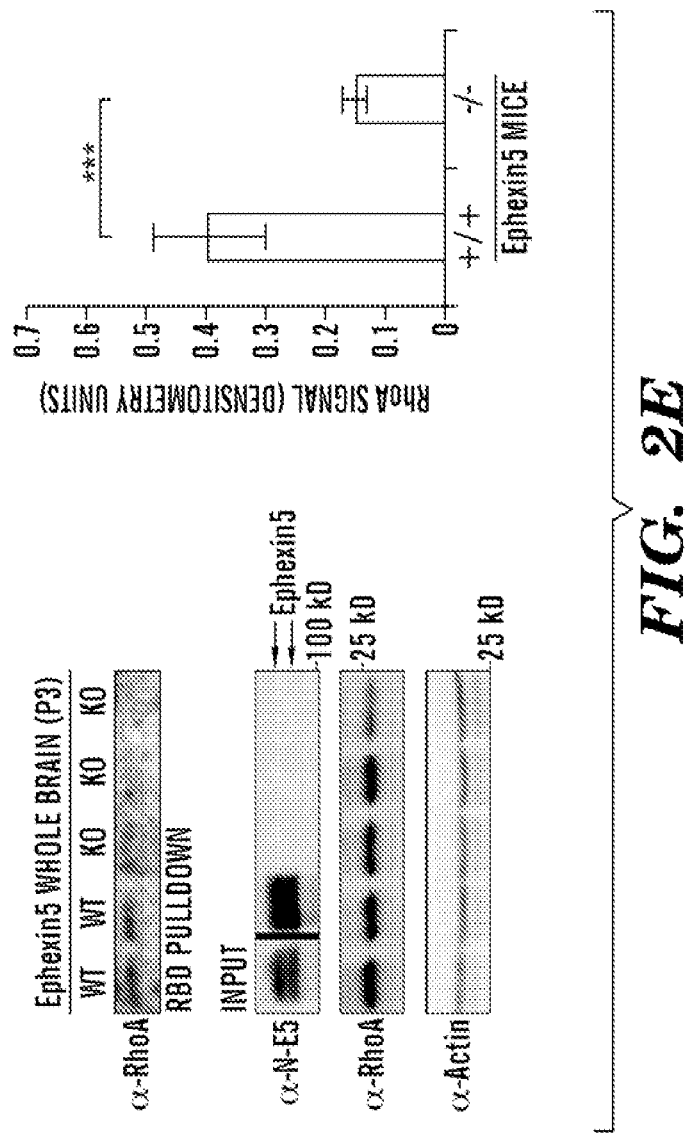

The inventors next asked if Ephexin5 expression affects RhoA activity in the brain. They lysed P3 whole brains from wild type or Ephexin5 knockout (Ephexin5$^{-/-}$) mice and performed a GST-RBD pull down assay. This analysis revealed a statistically significant decrease in RhoA activation in brain extracts from Ephexin5$^{-/-}$ mice compared to wild type mice, indicating that Ephexin5 is required to maintain wild type levels of RhoA activity in the brain (FIG. 2E).

Example 3

Ephexin5 Negatively Regulates Excitatory Synapse Number

Figure 10A:
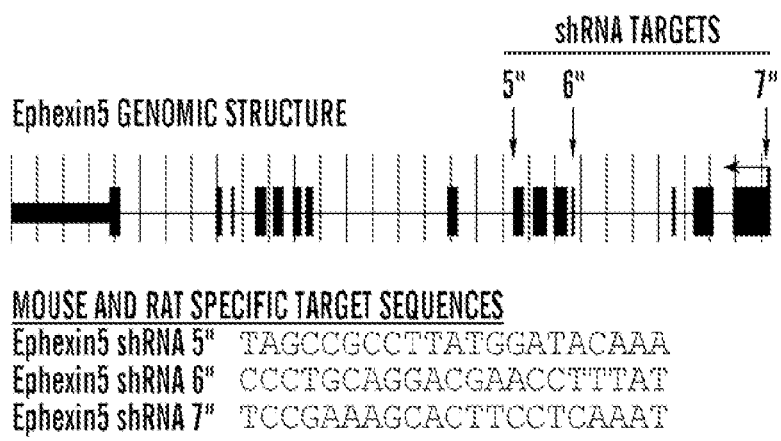
FIGS. 10A-10D show Ephexin5 knockdown by shRNA.
Figure 10B:
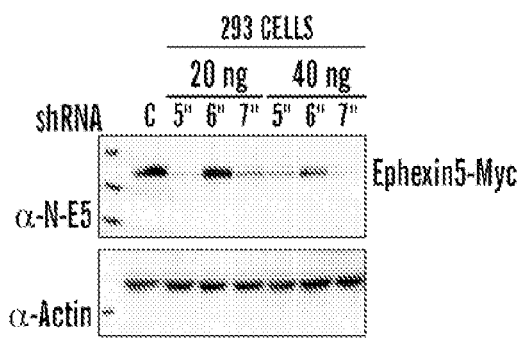
Figure 10C:
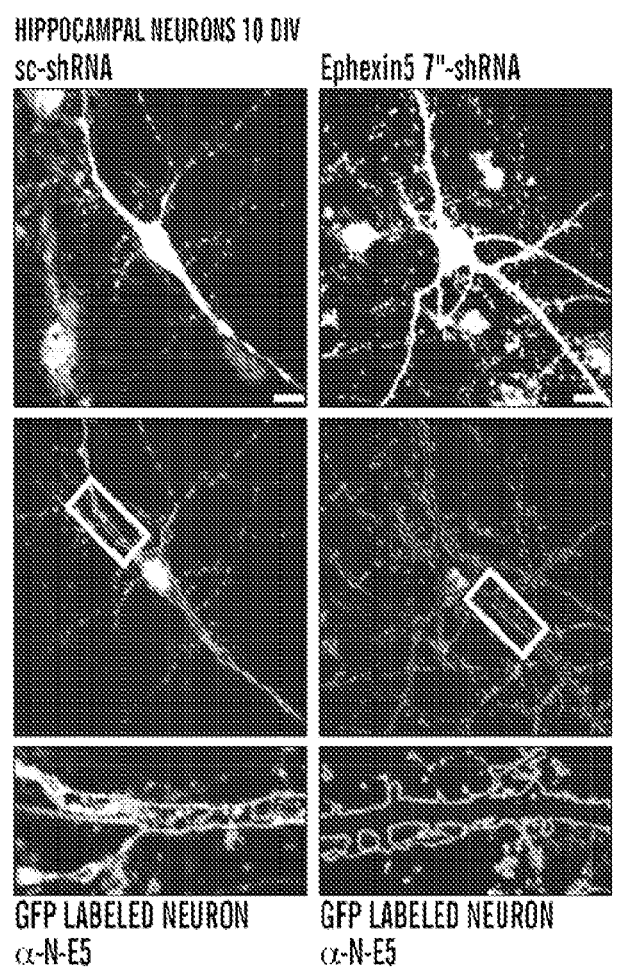

The inventors' findings indicated that Ephexin5 interacts with EphB, a key regulator of excitatory synapse development. Thus, they next asked whether Ephexin5 plays a role in the development of excitatory synapses. Towards this end, they generated two short hairpin RNA constructs that each effectively knocks down Ephexin5 protein levels when expressed in HEK293T cells (FIGS. 10A and 10B). These shRNAs were introduced into cultured hippocampal neurons together with a plasmid that drives expression of green fluorescent protein (GFP) to allow detection of the transfected cells. The inventors found by staining with an anti-N-terminal Ephexin5 antibody that the Ephexin5 shRNAs (E5-shRNA), but not control shRNAs, efficiently knocked down Ephexin5 expression selectively in the transfected neurons (FIG. 10C).

Figure 3A:
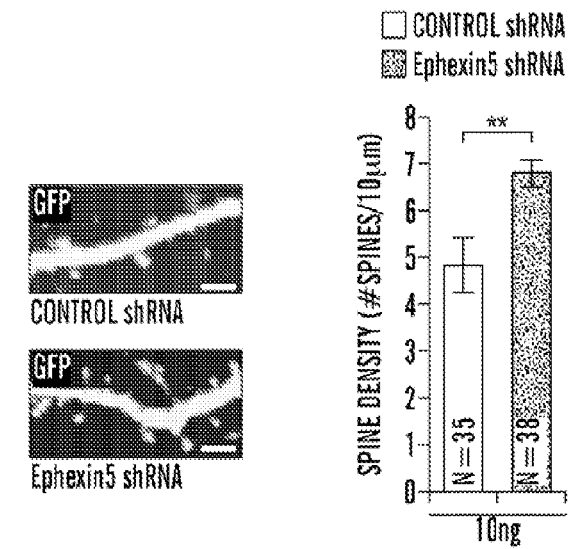
FIGS. 3A-3E show that Ephexin5 negatively regulates excitatory synapses number.
Figure 3B:
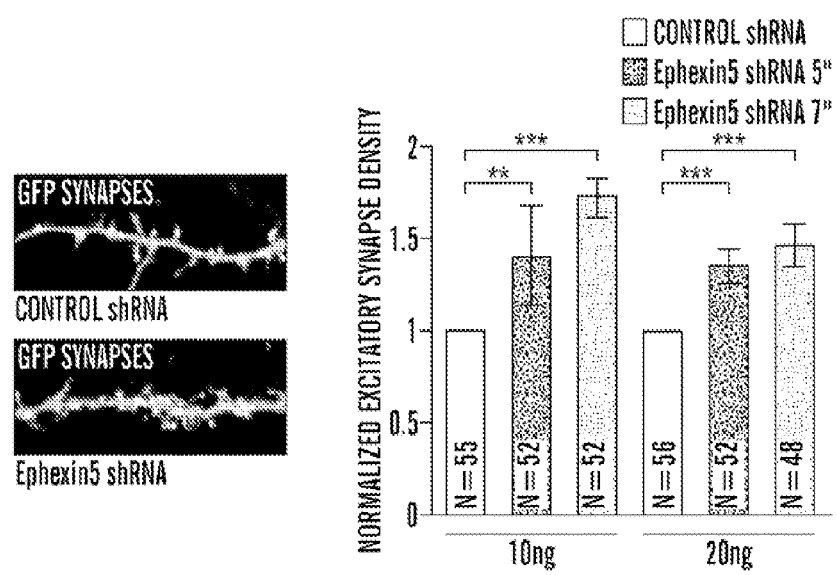
Figure 3C:
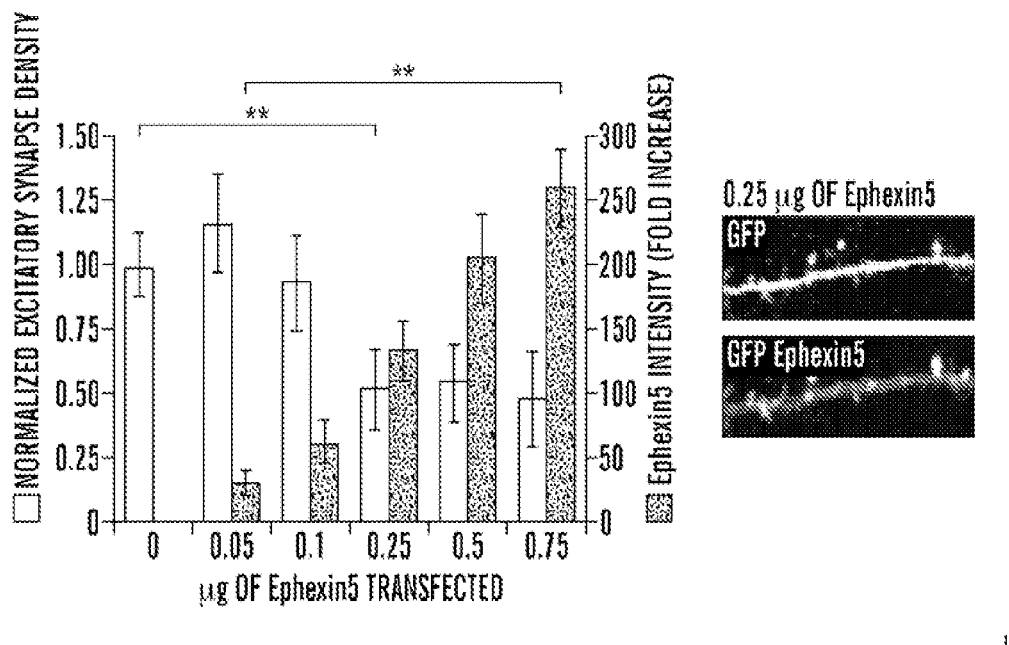
Figure 3D:
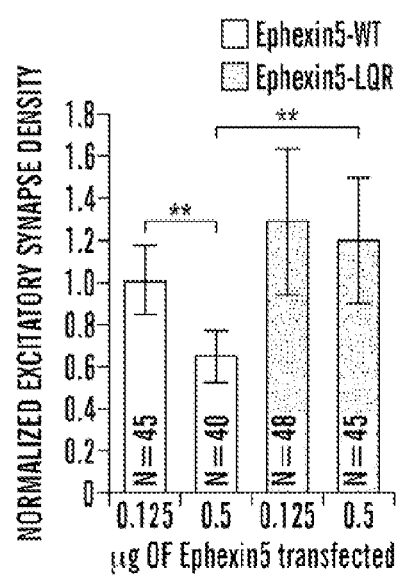
Figure 10D:
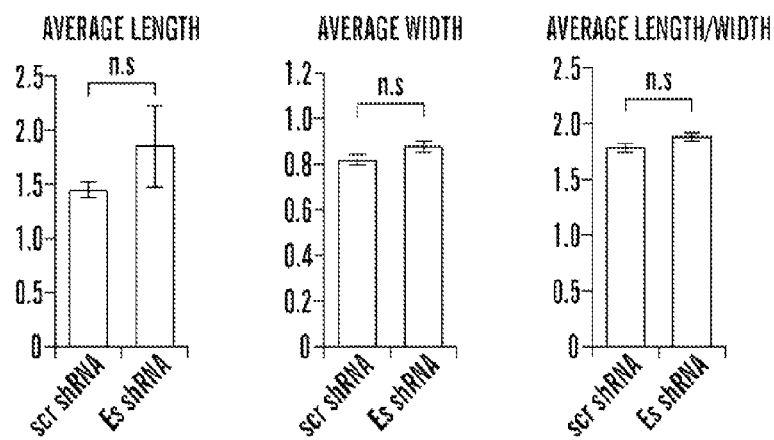
Figure 10D:
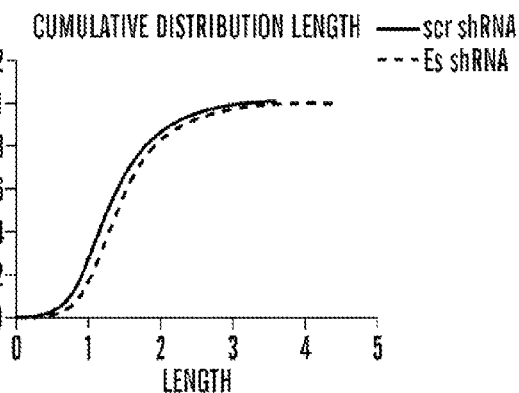
Figure 10D:
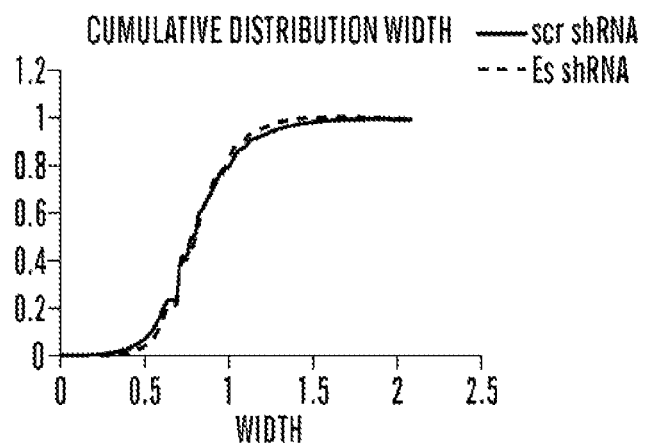
Figure 10D:
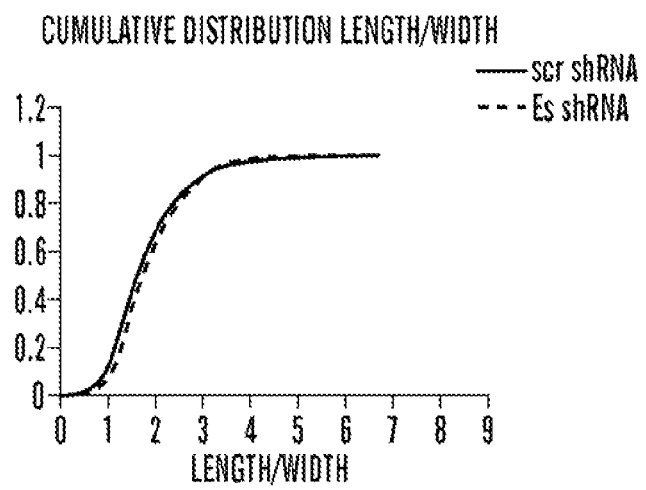

The inventors' method for introducing shRNAs results in the transfection of a low percentage of the neurons, thus facilitating quantification of the number of synapses/dendritic spines that are present on the transfected neuron (Paradis et al., 2007). The number of dendritic spines that are present on a shRNA-expressing neuron was quantified by first marking each dendritic spine found on the developing dendrites of the transfected neuron and then using MetaMorph analysis tools to tally the number of marked spines that were present on a given length of dendrite. The number of excitatory synapses that were present on a shRNA-expressing neuron was determined by staining with the postsynaptic excitatory synaptic marker PSD-95 and the presynaptic excitatory synaptic marker Synapsin. Using MetaMorph analysis tools, the inventors quantified the number of overlapping pre- and post-synaptic puncta on the transfected green fluorescing neuron to determine excitatory synapse density. The inventors observed a significant increase in the number of excitatory synapses and dendritic spines that were present on the E5-shRNAexpressing neurons compared to neurons expressing control shRNAs (FIGS. 3A and 3B). In contrast to the increases in dendritic spine and excitatory synapse density, the inventors failed to detect a significant change in dendritic spine length or width under these conditions (FIG. 10D). These findings indicate that Ephexin5 functions to restrict spine/excitatory synapse number but has no significant effect on spine morphology. Consistent with these conclusions, the inventors found that overexpression of Ephexin5 in hippocampal neurons lead to a decrease in the number of excitatory synapses that were present on the Ephexin5-overexpressing neurons (FIG. 3C). This ability of Ephexin5 to negatively regulate excitatory synapse number required its RhoA GEF activity, as overexpression of Ephexin5-LQR had no effect on synapse number (FIG. 3D).

Figure 3E:
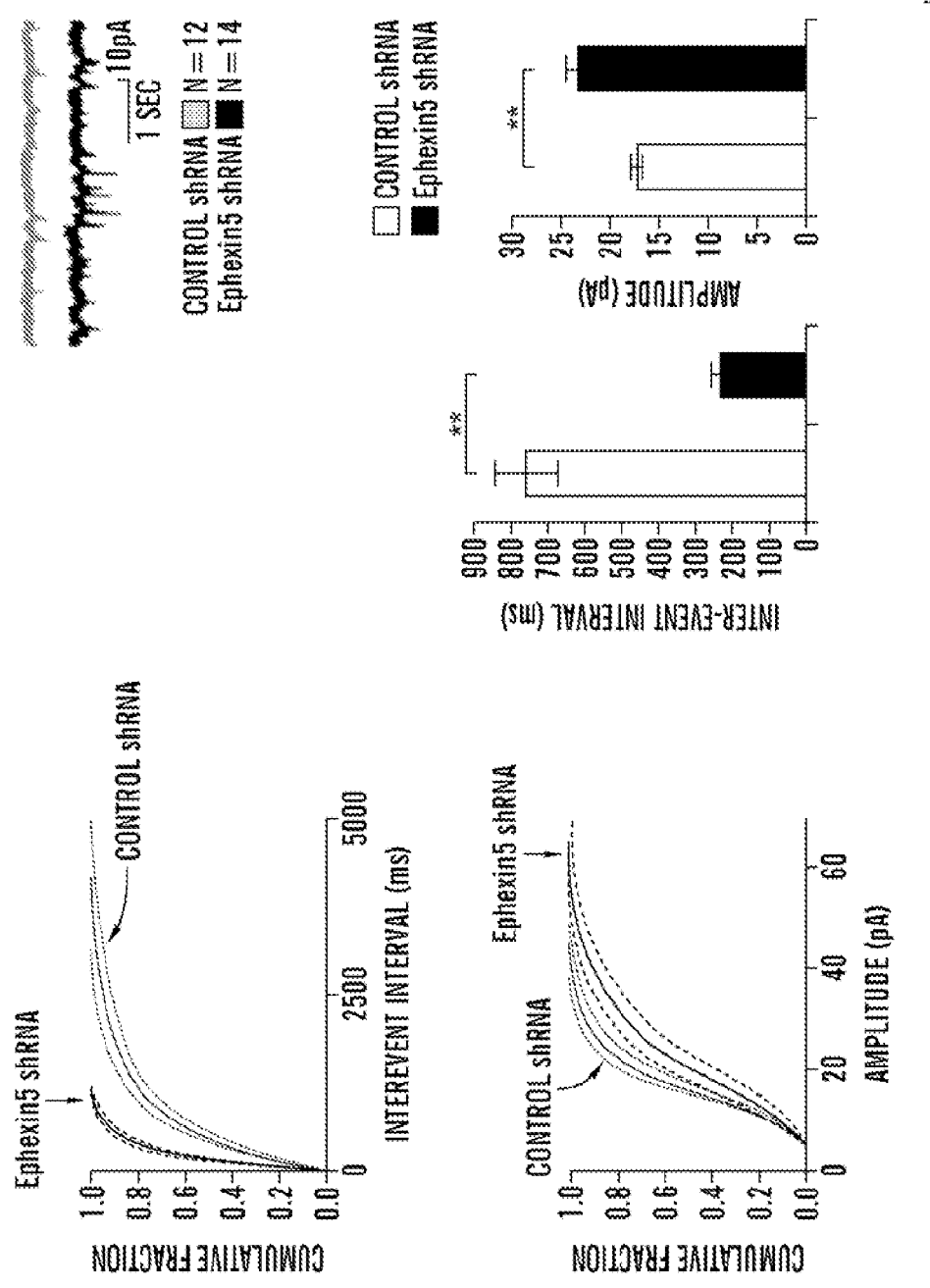
Figure 8A:
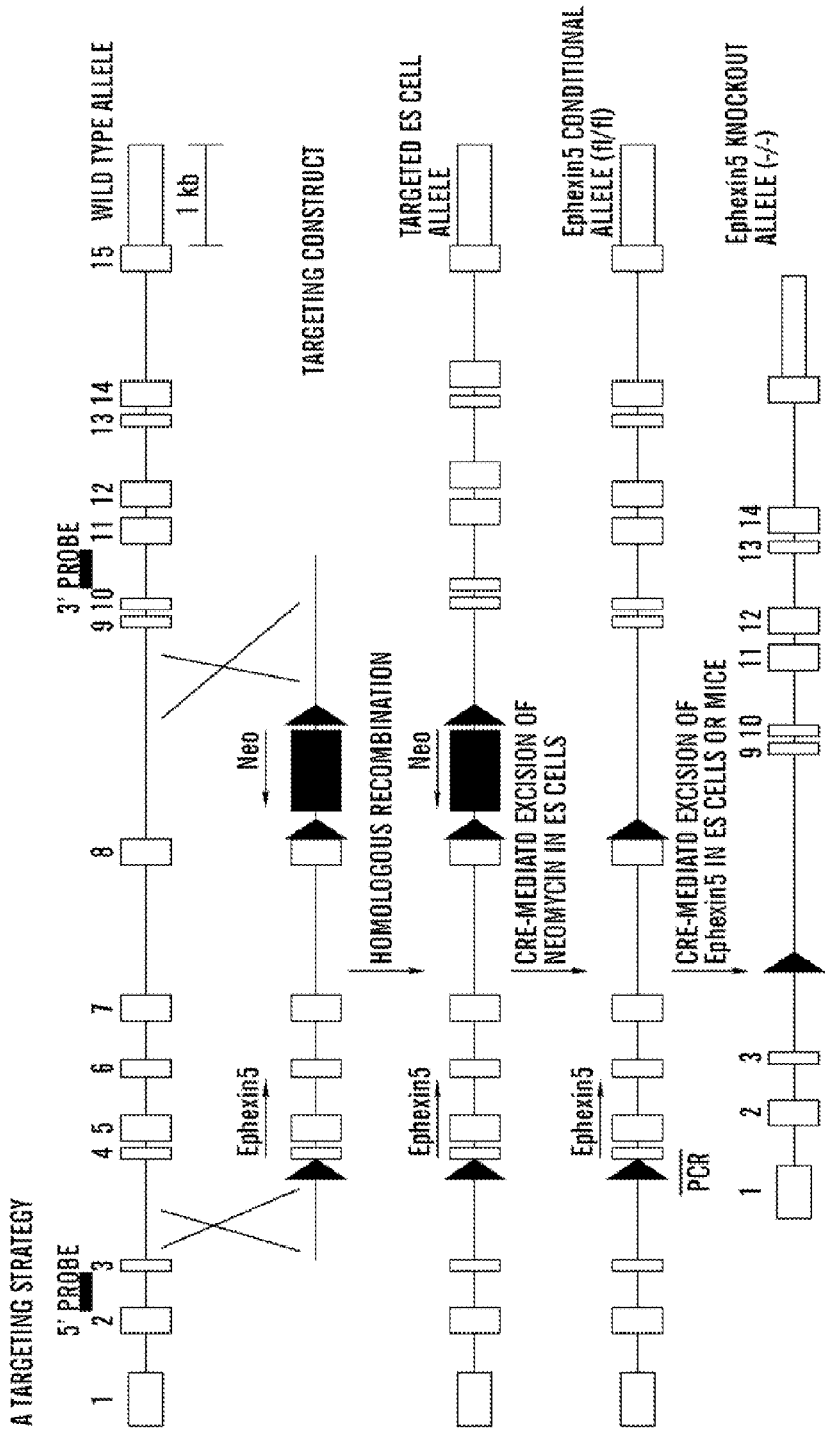
FIGS. 8A-8F show the construction and validation of the Ephexin5 and Ephexin5 mice.
Figures 8B, 8C, 8D:
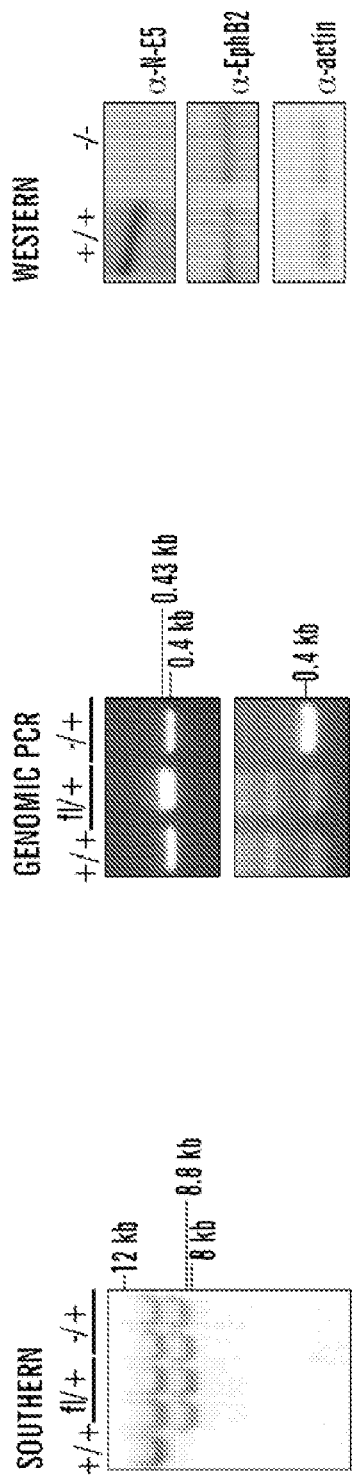
Figure 8F:
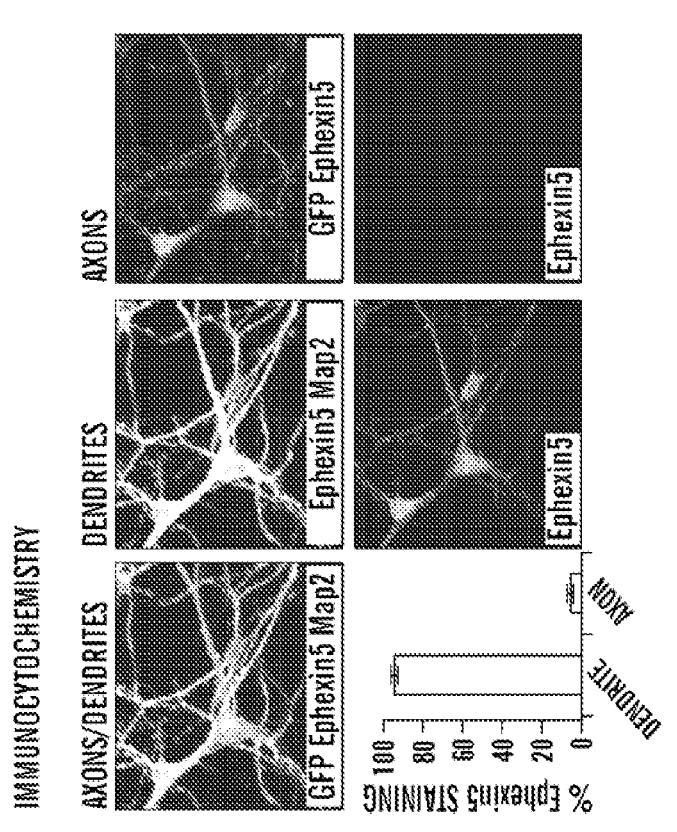
Figure 8E:
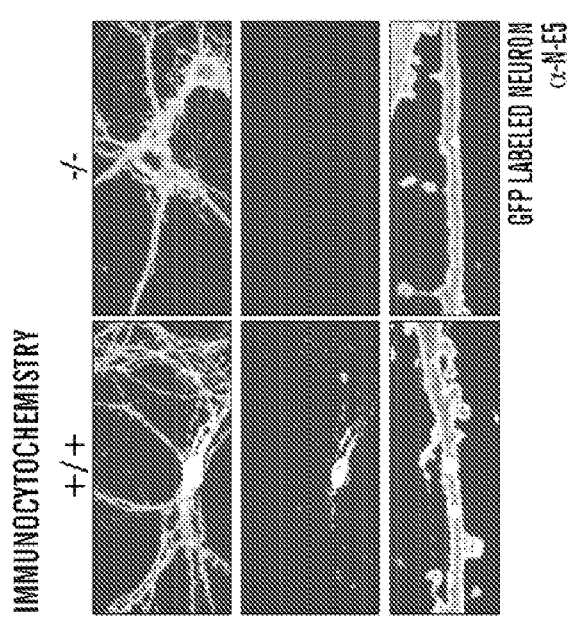

To assess the effect of reducing Ephexin5 levels on the functional properties of excitatory synapses, the invnetors performed electrophysiological recordings. They recorded miniature excitatory postsynaptic currents (mEPSCs) from cultured hippocampal neurons transfected with E5-shRNA or control shRNA. The inventors observed an increase in the frequency and amplitude of mEPSCs on neurons expressing E5-shRNA compared to a scrambled hairpin control (FIG. 3E). An increase in the average mEPSC amplitude by a reduction in Ephexin5 levels indicated that Ephexin5 acts postsynaptically to restrict excitatory synapse function. The increase in mEPSC frequency can be due to an increase in presynaptic vesicle release onto the transfected neuron or an increase in the number of excitatory synapses that are present on the transfected neuron. Without wishing to be bound by a specific mechanistic model, the inventors' data suggests that mEPSC frequency is due to an increase in the number of excitatory synapses that are present on the transfected neuron because inventors' transfection protocol selectively reduced Ephexin5 levels postsynaptically and also because an increase in synapse number was most consistent with the increase in co-staining of pre- and post-synaptic markers that the inventors observed when the level of Ephexin5 was reduced. This mechanistic model, Ephexin5 functions postsynaptically, is further supported by immunofluorescence staining experiments demonstrating that Ephexin5 was enriched in dendrites relative to axons (FIG. 8F).

Figure 4A:
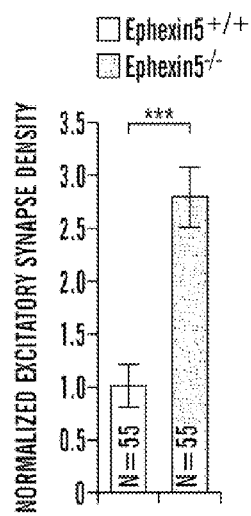
FIGS. 4A-4F show that Ephexin5 restricts EphB control of excitatory synapse formation.

As an independent means of assessing the importance of Ephexin5 in the control of excitatory synapse number, the inventors generated Ephexin5 knockout mice (FIG. 8). The inventors cultured hippocampal neurons from Ephexin5$^{-/-}$ mice or their wild type littermates for 10 days in vitro and then, following transfection of a GFP-expressing plasmid into these neurons, the inventors quantified the number of excitatory synapses present on the transfected neuron at DIV14. Consistent with thier observations using shRNA to knock down Ephexin5 expression, the inventors observed a three-fold increase in the number of synapses that were present on Ephexin5$^{-/-}$ neurons compared to heterozygous Ephexin5$^{+/-}$ neurons (FIG. 4A). Taken together with the Ephexin5 shRNA knockdown and Ephexin5 overexpression analyses, these findings indicated that Ephexin5 acts postsynaptically to reduce excitatory synapse number.

Figure 4B:
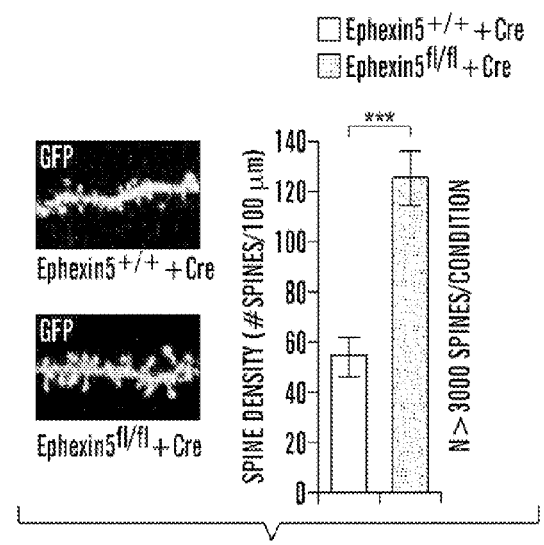
Figure 11:
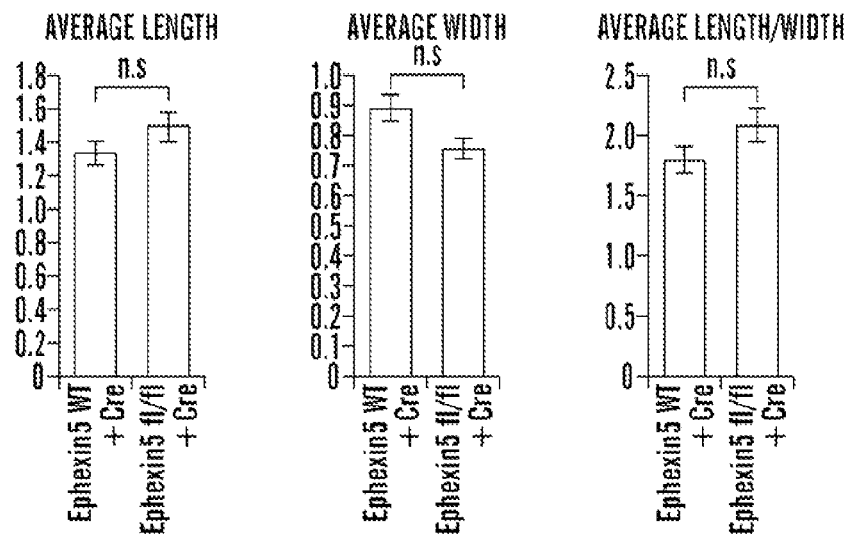
FIG. 11 shows the effect of Ephexin 5 knockdown on spine length and width. Loss of Ephexin5 function does not affect dendritic spine morphology in an intact circuit. Organotypic slices were prepared from P7 WT and Ephexin5 conditional littermates and at DIV3 biolistically transfected with Cre or control plasmid and GFP. At DIV7 (analogous to DIV14 in dissociated cultures) neurons were fixed and mounted for imaging. Over 200 μm of dendrite was imaged per neuron with 10 neurons imaged per animal totaling over 3000 spines. The data represent at least two animals from a total of two different litter pairs quantified at the same time. These results were verified by blinded counting and quantification from a third party to verify significance. Data is plotted as cumulative distribution to identify populations of spines that have changed in length or width.
Figure 11:
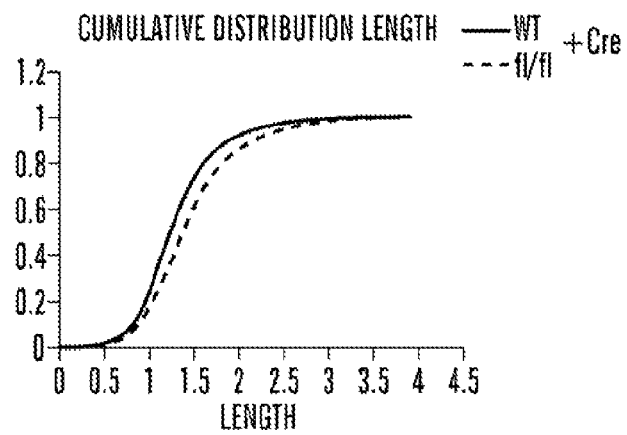
Figure 11:
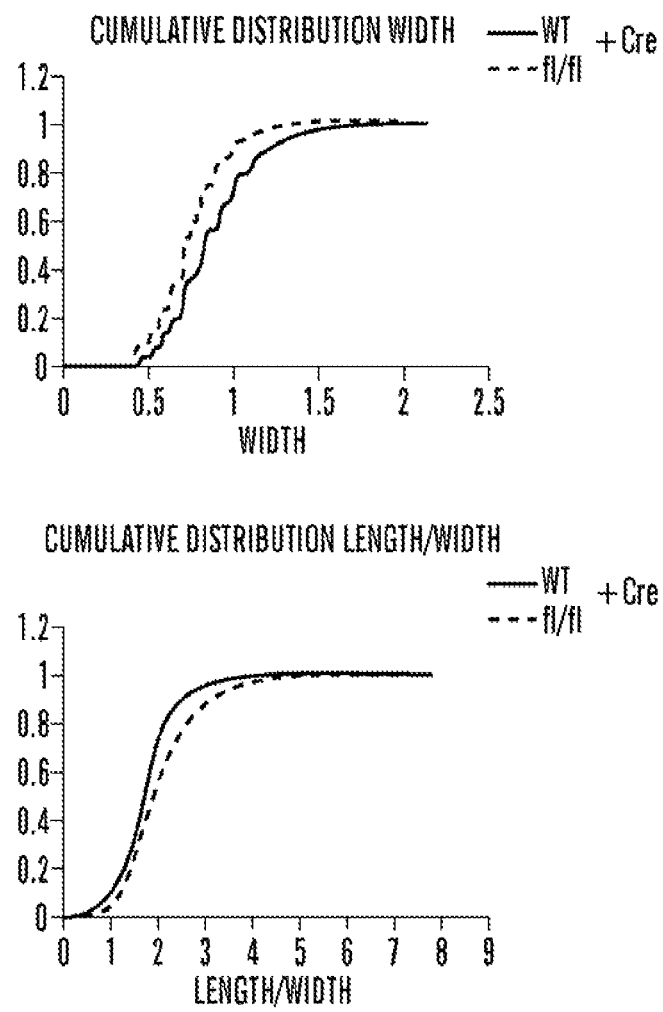

The inventors next tested to see if Ephexin5 regulates synapse number in the context of an intact developing neuronal circuit. Towards this end, they generated conditional Ephexin5 (Ephexin5$^{fl/fl}$) animals in which LoxP sites were inserted within the Ephexin5 gene (FIG. 8). Upon introduction of Cre recombinase into cells, exons 4-8 of the Ephexin5 gene are excised resulting in a cell that no longer produces Ephexin5 protein (data not shown). Organotypic slices were prepared from the hippocampus of the Ephexin5$^{fl/fl}$ mice or their wild type littermates. Using the biolistic transfection method, a plasmid expressing Cre recombinase was introduced into a low percentage of neurons in the slices. The inventors discovered that introduction of a Cre-expressing plasmid into Ephexin5$^{fl/fl}$ neurons in the hippocampal slice led to a significant increase in the density of dendritic spines present on the Cre-expres sing neurons (FIG. 4B). In contrast, expression of Cre in neurons of a wild type hippocampal slice had no effect on dendritic spine density. The length and width of dendritic spines analyzed in these experiments showed no statistically significant difference between wild type and Ephexin5$^{-/-}$ neurons (FIG. 11). Thus, the elimination of Ephexin5 expression in neurons in the context of an intact neuronal circuit leads to an increase in the number of mature dendritic spines.

Figure 4C:
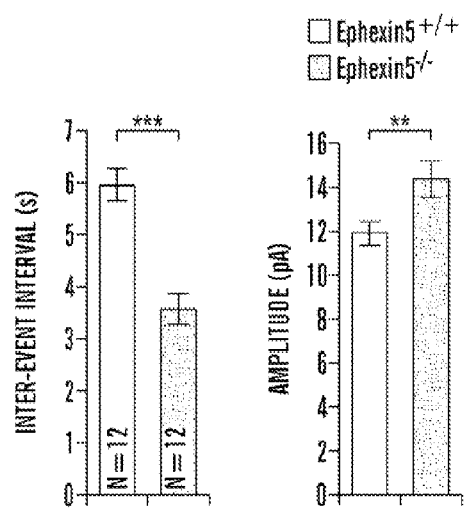
Figure 4D:
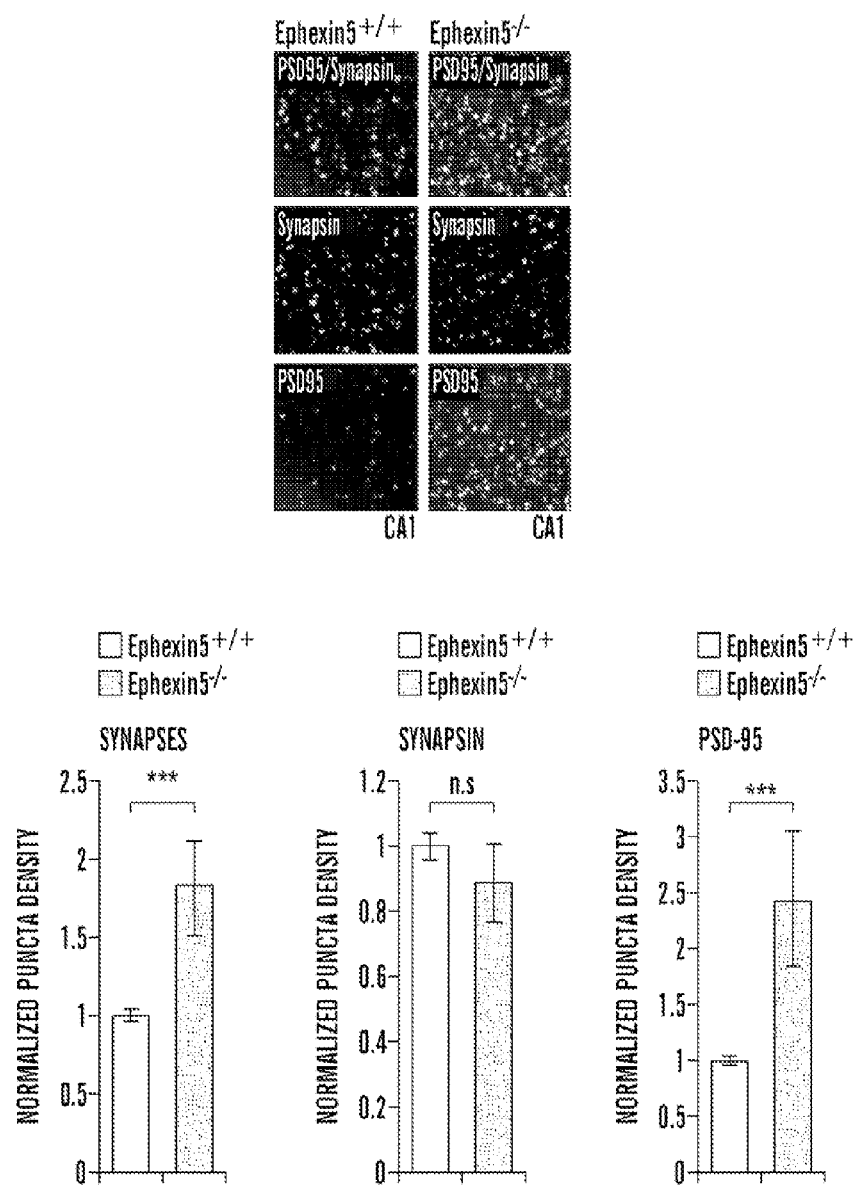

To assess the role of Ephexin5 in hippocampal circuit development in vivo, the inventors performed acute slice physiology experiments in the CA1 region of the hippocampus from wild type or Ephexin5$^{-/-}$ mice. They found that relative to wild type neurons Ephexin5 knockout CA1 pyramidal neurons there were more frequent excitatory events that have larger amplitude (FIG. 4C). A possible explanation for these findings is that when Ephexin5 function is disrupted during in vivo development more excitatory synapses form resulting in more excitatory postsynaptic events. To test this possibility, the inventors used array tomography to quantify the number of excitatory synapses that form in the CA1 stratum radiatum of wild type and Ephexin5$^{-/-}$ mice. Inventors observed a ~2-fold increase in the number of excitatory synapses within the CA1 region of the Ephexin5$^{-/-}$ hippocampus compared to wild type mice (FIG. 4D). Specifically, in the array tomography analysis the number of juxtaposed synapsin and PSD-95 puncta was quantified and considered a measurement of the number of excitatory synapses that formed within the CA1 region of the hippocampus in vivo. This analysis revealed a significant increase in the number of PSD-95 puncta but no change in overall number of synapsin puncta density (FIG. 4D). This indicated that the increase in excitatory synapse number in the stratum radiatum of Ephexin5$^{-/-}$ mice was likely due to the absence of Ephexin5 post-synaptically and that when Ephexin5 is present within dendrites it functions to negatively regulate synapse number in vivo. Accordingly, based on these results and inventors' studies using dissociated cultured neurons, a key function of Ephexin5 is to restrict excitatory synapse number during the development of neuronal circuits.

Example 4

Ephexin5 Restricts EphB2 Control of Excitatory Synapse Formation

The inventors next considered the possibility that the ability of Ephexin5 to restrict excitatory synapse number might be controlled by EphB2 signaling. Specifically, they hypothesized that by binding to EphB2, Ephexin5 may restrict excitatory synapse development at locations within the plasma membrane where EphBs are present. The binding of EphrinBs to EphB2 might then be required to initiate a signaling cascade that results in Ephexin5 inactivation or degradation, thus allowing EphB2 to positively regulate excitatory synapse development. If this hypothesis is correct then the increase in excitatory synapse number that the inventors detect when Ephexin5 levels are reduced would require EphB2 signaling.

Figure 4E:
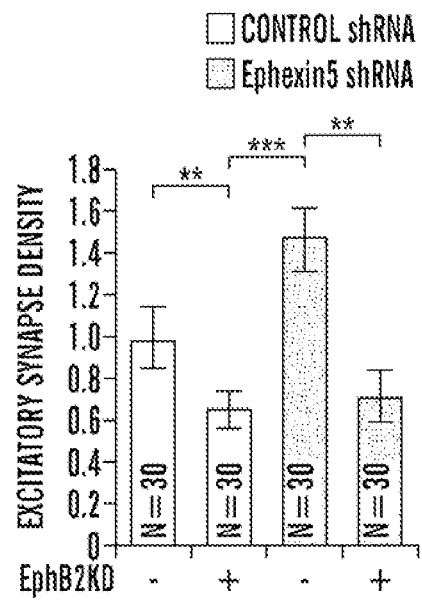
Figure 4F:
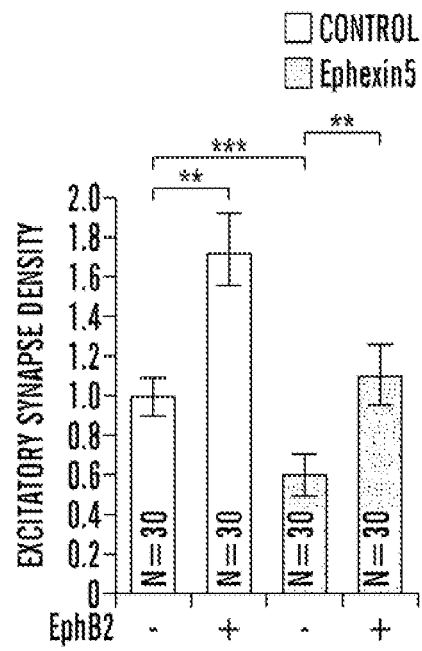

To test this idea, the inventors asked whether reducing EphB2 signaling eliminates the increase in excitatory synapse number detected when Ephexin5 levels are knocked down by expression of E5-shRNA. To block EphB2 activation, the inventors introduced into neurons a kinase dead version of EphB2 (EphB2-KD) which has been previously shown to block EphB2 signaling (Dalva et al., 2000). As described above, expression of E5-shRNA in neurons lead to a significant increase in the number of synapses that were present on the E5-shRNA-expressing neuron. However, this increase was reversed if the E5-shRNA was co-transfected with a plasmid that drives expression of EphB2-KD, but was not affected by co-transfection of a control plasmid (FIG. 4E). These findings indicated that the increase in excitatory synapse number that occurs when Ephexin5 levels were reduced requires EphB signaling. Consistent with this conclusion, the inventors found that if they overexpressed wild type EphB2 in neurons more synapses were present on the EphBexpressing neuron. However, this effect was reduced if Ephexin5 was overexpressed in neurons together with EphB (FIG. 4F). It is possible that the ability of overexpressed Ephexin5 to suppress the synapse-promoting effect of EphB2 reflects independent actions of these two signaling molecules. However, given that EphB2 and Ephexin5 interact with one another in neurons, the most likely interpretation of these results is that Ephexin5 functions directly to restrict the synapse-promoting effects of EphB2. Based on this data, the inventors predicted that for EphB2 to positively regulate excitatory synapse development it would be necessary to inactivate and/or degrade Ephexin5.

Example 5

EphB Mediates Phosphorylation of Ephexin5 at Tyrosine-361

The inventors next considered the possibility that since EphB2 is a tyrosine kinase it may inhibit the guanine nucleotide exchange activity or expression of the Ephexin5 protein by catalyzing the tyrosine phosphorylation of Ephexin5. In support of this possibility, stimulation of dissociated mouse hippocampal neurons with EphrinB1 for 15 minutes led to an increase in the level of Ephexin5 tyrosine phosphorylation as detected by probing immunoprecipitated Ephexin5 with the anti-pan-phospho-tyrosine antibody, 4G10 (FIG. 5A).

To assess the effect of tyrosine phosphorylation on Ephexin5 function the inventors first sought to identify the specific tyrosine residues on Ephexin5 that become newly phosphorylated upon binding of EphrinB to EphB. The inventors had previously shown that EphrinA1 stimulation of cultured neurons leads to the tyrosine phosphorylation of Ephexin1 at tyrosine 87 (Sahin et al., 2005). On the basis of this finding, the inventors hypothesized that exposure of neurons to EphrinB1 might promote the phosphorylation of the analogous tyrosine residue (Y361) on Ephexin5 (FIG. 5B) and that phosphorylation at this site may lead to Ephexin5 inactivation. To address this possibility, the inventors overexpressed EphB2 in HEK293T cells together with wild type Ephexin5 or a mutant form of Ephexin5 in which Y361 is converted to a phenylalanine (Ephexin5-Y361F). Lysates were prepared from the transfected cells and after SDS-PAGE were immunoblotted with anti-phosphotyrosine (4G10) antibody (FIG. 5C). The inventors discovered that in the presence of EphB2, Ephexin5-WT, but not Ephexin5-Y361F, become tyrosine phosphorylated. This indicates that EphB2 catalyzes the tyrosine phosphorylation of Ephexin5 primarily at Y361.

Figure 12A:
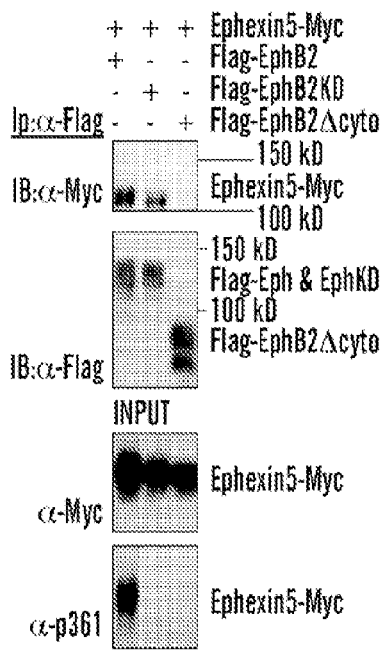
FIGS. 12A-12C show that EphB mediates phosphorylation of Ephexin5 at tyrosine-361.
Figure 12B:
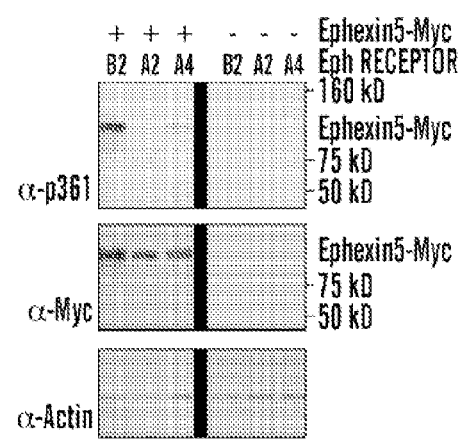

To show definitively that Ephexin5 Y361 is tyrosine phosphorylated, the inventors generated antiEphexin5 phospho-Y361 antibodies (anti-pY361). To demonstrate that these antibodies specifically recognize the Y361-phosphorylated form of Ephexin5, the inventros immunoblotted cell lysates prepared from HEK293T cells that express EphB2 and either Ephexin5-WT or Ephexin5-Y361F with the anti-pY361 antibodies. This analysis demonstrated that the antipY361 antibodies bind to wild type Ephexin5 but not Ephexin5-Y361F (FIG. 5C). Furthermore, using these antibodies the invnetors found that when wild type EphB2, but not a kinase dead or cytoplasmic truncated version of EphB2, was expressed in HEK293T cells together with Ephexin5, Ephexin5 become tyrosine phosphorylated at Y361 (FIG. 12A). In contrast, when EphA4 or EphA2 were expressed in HEK293T cells they detected little to no phosphorylation of Ephexin5 at Y361 (FIG. 12B). This result was consistent with inventors' finding that Ephexin5 does not preferentially interact with EphAs. These findings indicate that EphB2, but not EphAs, is required for Ephexin5 Y361 phosphorylation.

Figure 5E:
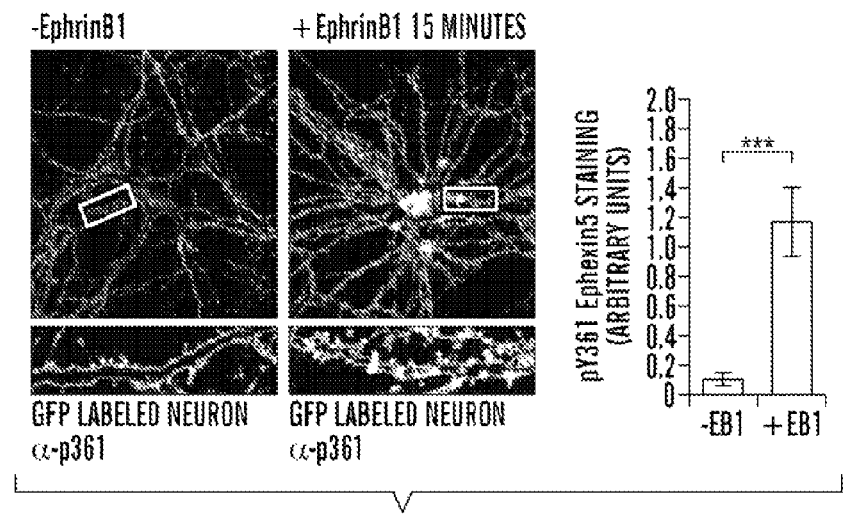
Figure 12C:
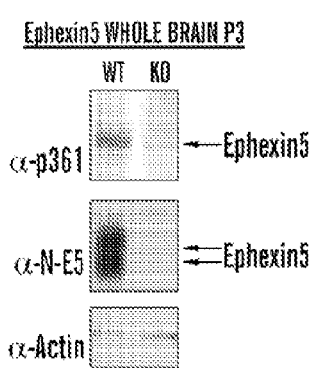

The inventors also found by immunoblotting with the anti-pY361 antibodies that Ephexin5 was phosphorylated at Y361 in the hippocampus of wild type but not Ephexin5 knockout mice (FIG. 12C), and that EphrinB1 stimulation of cultured hippocampal neurons lead to Ephexin5 Y361 phosphorylation (FIG. 5D). By immunofluorescence microscopy the inventors detected punctate anti-pY361 antibody staining along the dendrites of EphrinB1-treated wild type neurons, but detected significantly less staining in untreated neurons (FIG. 5E). This result indicated that Ephexin5 become newly phosphorylated at Y361 upon exposure of hippocampal neurons to EphrinB1.

Example 6

EphB2-Mediated Degradation of Ephexin5 is Kinase and Proteasome Dependent

Figure 5F:
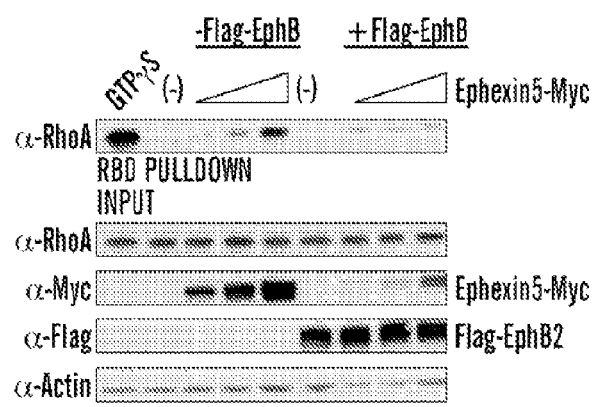
Figure 5G:
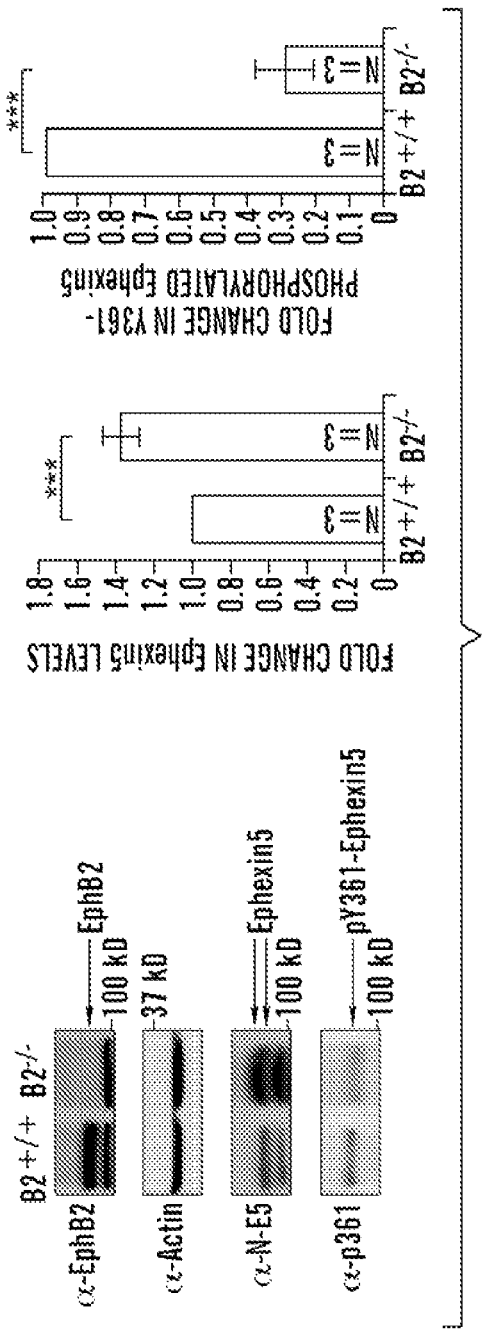
Figure 6A:
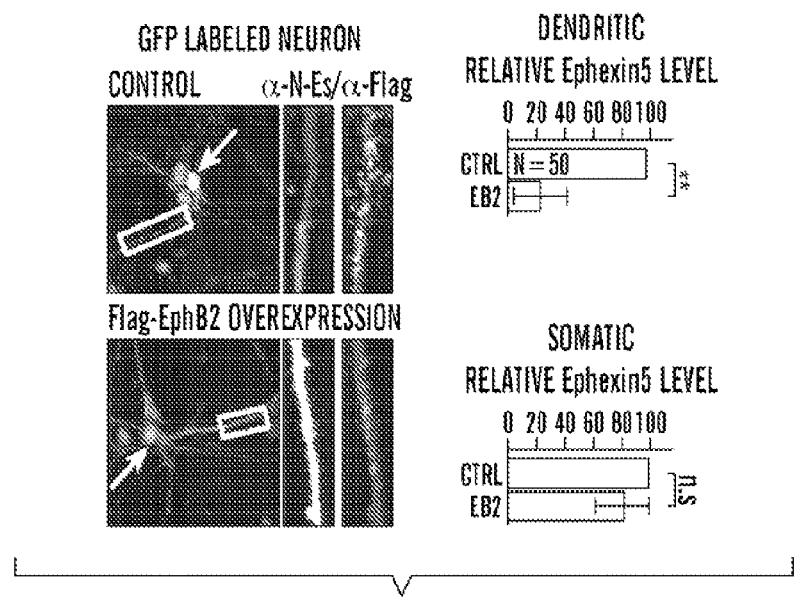
FIGS. 6A-6I show that EphB2-mediated degradation of Ephexin5 is kinase and proteasome dependent.
Figure 6B:
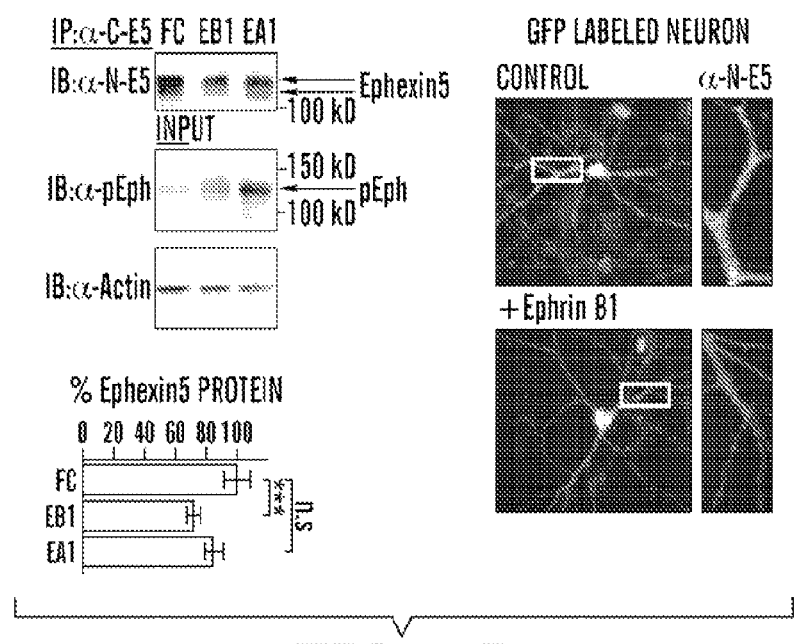
Figure 6C:
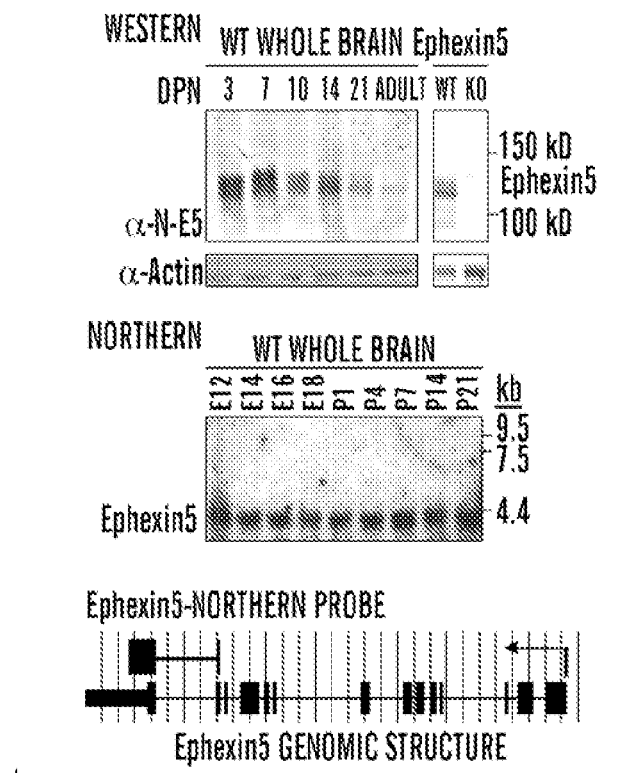
Figures 6D, 6E:
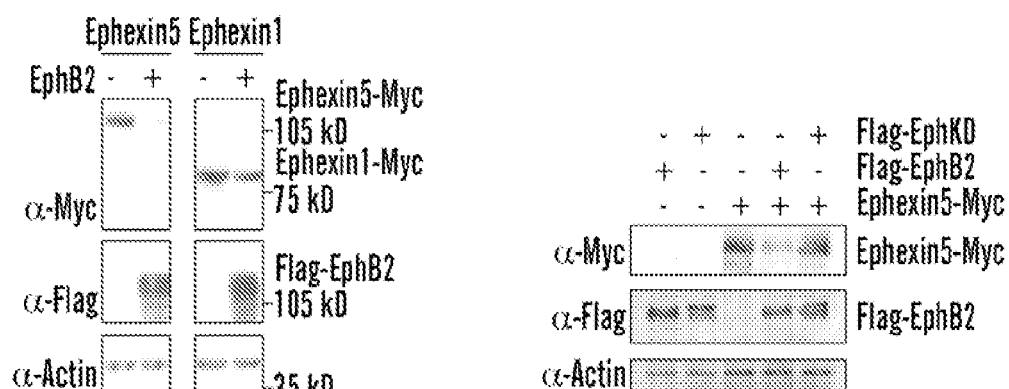
Figure 13:
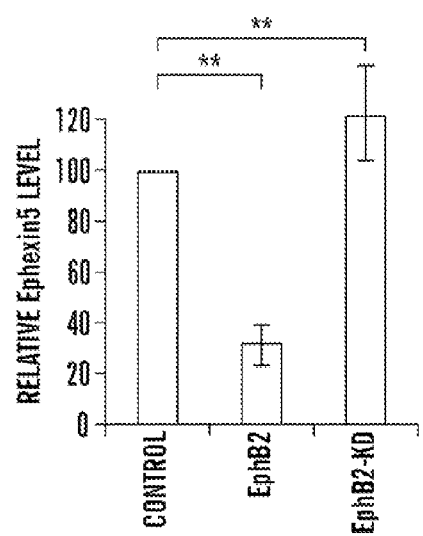
FIG. 13 shows that EphB2-mediated degradation of Ephexin5 is kinase dependent. Overexpression of EphB2 or EphB2-KD in neurons at DIV10 leads to a decrease in endogenous Ephexin5 expression by DIV14 in transfected neurons as measured by immunocytochemistry. Images were quantified by MetaMorph. The data represents three independent experiments.

The inventors next tested to see if EphrinB1 stimulation of Ephexin5 Y361 phosphorylation leads to a change in Ephexin5 activity or expression. To begin to investigate this possibility the inventors first checked if EphB suppresses Ephexin5-dependent RhoA activation in a phosphorylation-dependent manner. They transfected HEK293T cells with Ephexin5 in the presence or absence of EphB2 and measured RhoA activity using the RBD pull down assay (FIG. 5F). They found that Ephexin5-dependent RhoA activation was significantly reduced in HEK293T cells expressing EphB2 and Ephexin5 compared to cells expressing Ephexin5 alone. These findings were consistent with the possibility that EphB2-mediated tyrosine phosphorylation of Ephexin5 either leads to a suppression of Ephexin5's ability to activate RhoA, or alternatively may trigger a decrease in Ephexin5 protein expression resulting in a decrease in RhoA activation in EphB2expressing cells. Without wishing to be bound by a particular mechanistic model, data presented herein indicates that EphB2-mediated tyrosine phosphorylation of Ephexin5 triggers a decrease in Ephexin5 protein expression resulting in a decrease in RhoA activation in EphB2expressing cells (FIG. 5F, Ephexin5 loading control). In support of the idea that EphB2 mediates Ephexin5 phosphorylation and decreased Ephexin5 expression the inventors found that when lysates from the brains of wild type or EphB2$^{-/-}$ mice were compared that Ephexin5 phosphorylation at Y361 decreased while the levels of Ephexin5 expression increased in the lysates from EphB2$^{-/-}$ mice (FIG. 5G). These data indicate that EphB2 may function to phosphorylate and degrade Ephexin5. Consistent with the idea that Ephexin5 expression is destabilized in the presence of EphB, the inventors observed that in the dendrites of cultured hippocampal neurons overexpressing EphB2, endogenous Ephexin5 expression levels were significantly reduced compared to control transfected neurons or neurons transfected with a kinase dead version of EphB2 (FIGS. 6A and 13). When neurons were exposed to EphrinB1 for varying periods of time (0, 15, 30, and 60 min), the inventors found by immunoblotting of neuronal extracts, or immunofluorescence staining with anti-Ephexin5 antibodies, that exposure to EphrinB1 led to a decrease in Ephexin5 protein expression within 15-30 minutes (FIG. 6B). The lack of complete loss of Ephexin5 expression by western blot may be due to the fact that EphrinB1 stimulation leads to dendritic and not somatic loss of Ephexin5 expression. Moreover, immunofluorescence staining revealed a loss of Ephexin5 puncta specifically within the dendrites of EphrinB1-stimulated neurons, consistent with the possibility that EphrinB1/EphB-mediated degradation of Ephexin5 may relieve an inhibitory constraint that suppresses excitatory synapse formation on dendrites. In support of this idea, the inventor found by immunoblotting of extracts from mouse hippocampi with antiEphexin5 antibodies that endogenous Ephexin5 protein levels were highest at postnatal day 3 prior to the time of maximal synapse formation and then decrease as synapse formation peaks in the postnatal period (FIG. 6D). Northern blotting revealed that this decrease in Ephexin5 protein was not due to a change in the level of Ephexin5 mRNA expression (FIG. 6C). Given that Ephexin5 protein levels decrease dramatically during the time period P7-P21 when synapse formation is maximal, these findings indicate that prior to synapse formation Ephexin5 may need to be degraded.

Figures 6F, 6G:
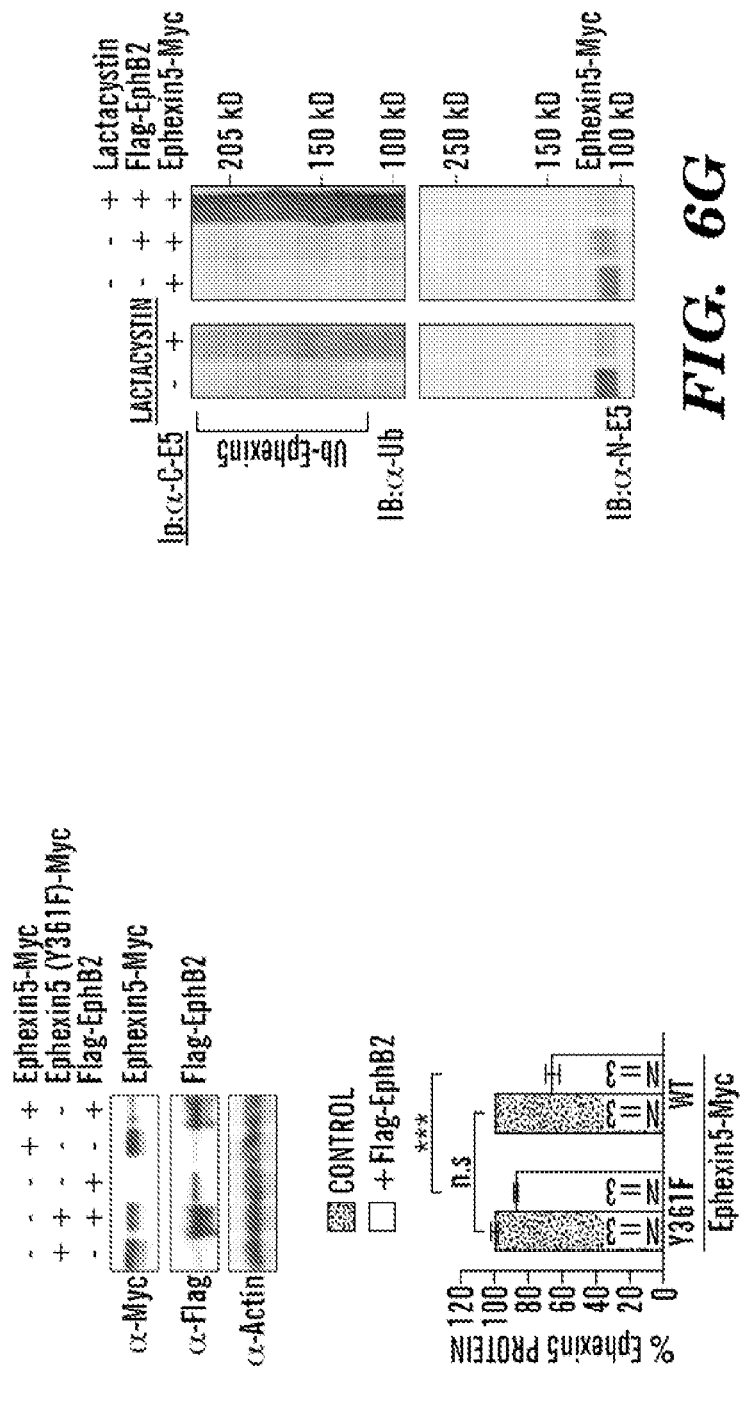

The invnetors asked whether EphB-mediated degradation of Ephexin5 could be reconstituted in heterologous cells. When EphB and Myc-tagged Ephexin5 were co-expressed in HEK293T cells the inventors observed a significant decrease in Ephexin5 protein expression in the presence of EphB2. The presence of EphB2 had no effect on the level of expression of a related GEF, Ephexin1 (FIG. 6D). The inventors next asked whether EphB-mediated degradation of Ephexin5 depends upon Y361 phosphorylation. They found that in HEK293T cells overexpres sing Myctagged Ephexin5, the co-expression of EphB2, but not EphB2-KD, resulted in a significant decrease in Ephexin5 levels (FIG. 6E). This indicated that EphB tyrosine kinase activity was required for Ephexin5 degradation. The EphB-mediated reduction in Ephexin5 levels was dependent on Y361 phosphorylation, as EphB2 expression had no effect on the level of Ephexin5 Y361F expression (FIG. 6F). This indicated that the phosphorylation of Ephexin5 at Y361 triggered Ephexin5 degradation.

Figure 6H:
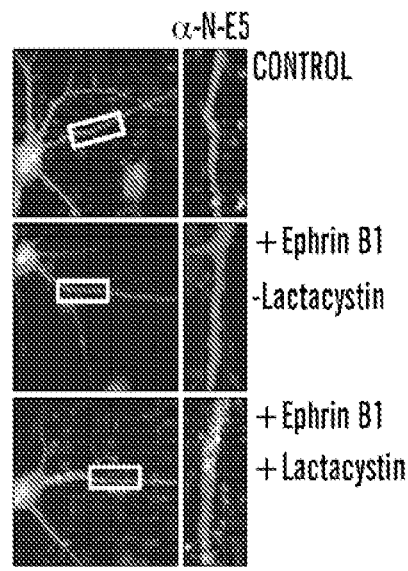

The inventors next considered the possibility that the Y361 phosphorylation-dependent decrease in Ephexin5 protein levels may be due to EphB-dependent stimulation of Ephexin5 proteasomal degradation. Consistent with this possibility the inventors found that addition of the proteasome inhibitor lactacystin to HEK293T cells lead to a reversal of the EphB-dependent decrease in Ephexin5 protein levels, as measured by an increase in total ubiquitinated Ephexin5 (FIG. 6G). In addition, in neuronal cultures the EphrinB1 induced decrease in Ephexin5 protein expression was blocked when the neurons were exposed to the proteasome inhibitor lactacystin prior to EphrinB1 addition (FIG. 6H). Notably, in the presence of lactacystin, Ephexin5 was ubiquitinated, further supporting the idea that Ephexin5 is degraded by the proteasome.

Figure 6I:
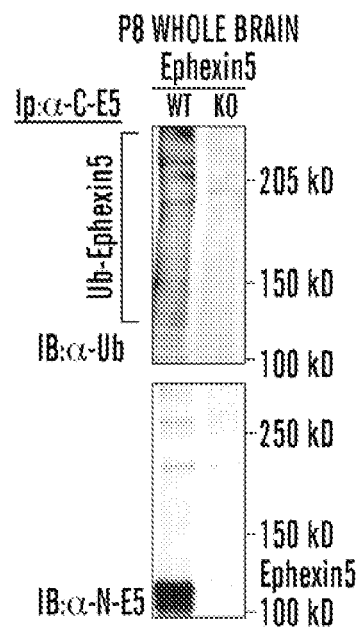

To test whether Ephexin5 is ubiquitinated in the brain, the inventors incubated wild type or Ephexin5 knockout mouse brain lysates with anti-Ephexin5 antibodies and after immunoprecipitation and SDS-PAGE, probed with anti-ubiquitin antibodies. This analysis detected the presence of ubiquitinated species in anti-Ephexin5 immunoprecipitates prepared from wild type but not Ephexin5$^{-/-}$ brain lysates (FIG. 6I). Taken together, these findings indicated that Ephexin5 is ubiquitinated in the brain.

The invnetors also found by yeast two-hybrid analysis that Ephexin5 binds Ubiquitin-B and Ubiquitin-C proteins as well as several ubiquitin E2 family members (data not shown). Moreover, the results of a recent unbiased screen for targets of the proteasome identified Ephexin5 as one of only several GEFs targeted by the ubiquitin proteasome (Yen et al., 2008). These findings, taken together with the observations that Ephexin5 is ubiquitinated, and that lactacystin treatment blocks the EphrinB-induced decrease in Ephexin5 expression, indicate that EphB induction of Ephexin5 Y361 phosphorylation triggers Ephexin5 degradation via the ubiquitin proteasome. Given the key role that Ephexin5 plays in suppressing excitatory synapse development, the inventors next sought to determine the mechanism by which EphrinB1/EphB-mediated Ephexin5 Y361 phosphorylation triggers Ephexin5 degradation.

Example 7

EphB2-Mediated Degradation of Ephexin5 Requires Ube3A

Figure 7A:
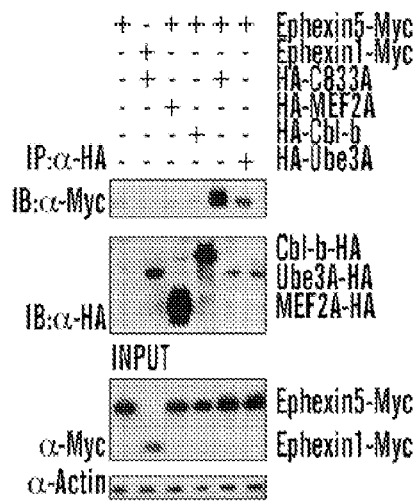
FIGS. 7A-7G show that EphB-mediated degradation of Ephexin5 requires Ube3A.
Figure 7B:
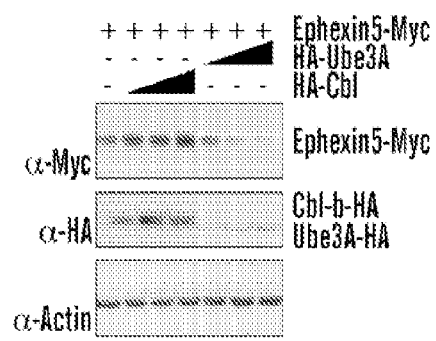
Figure 14:
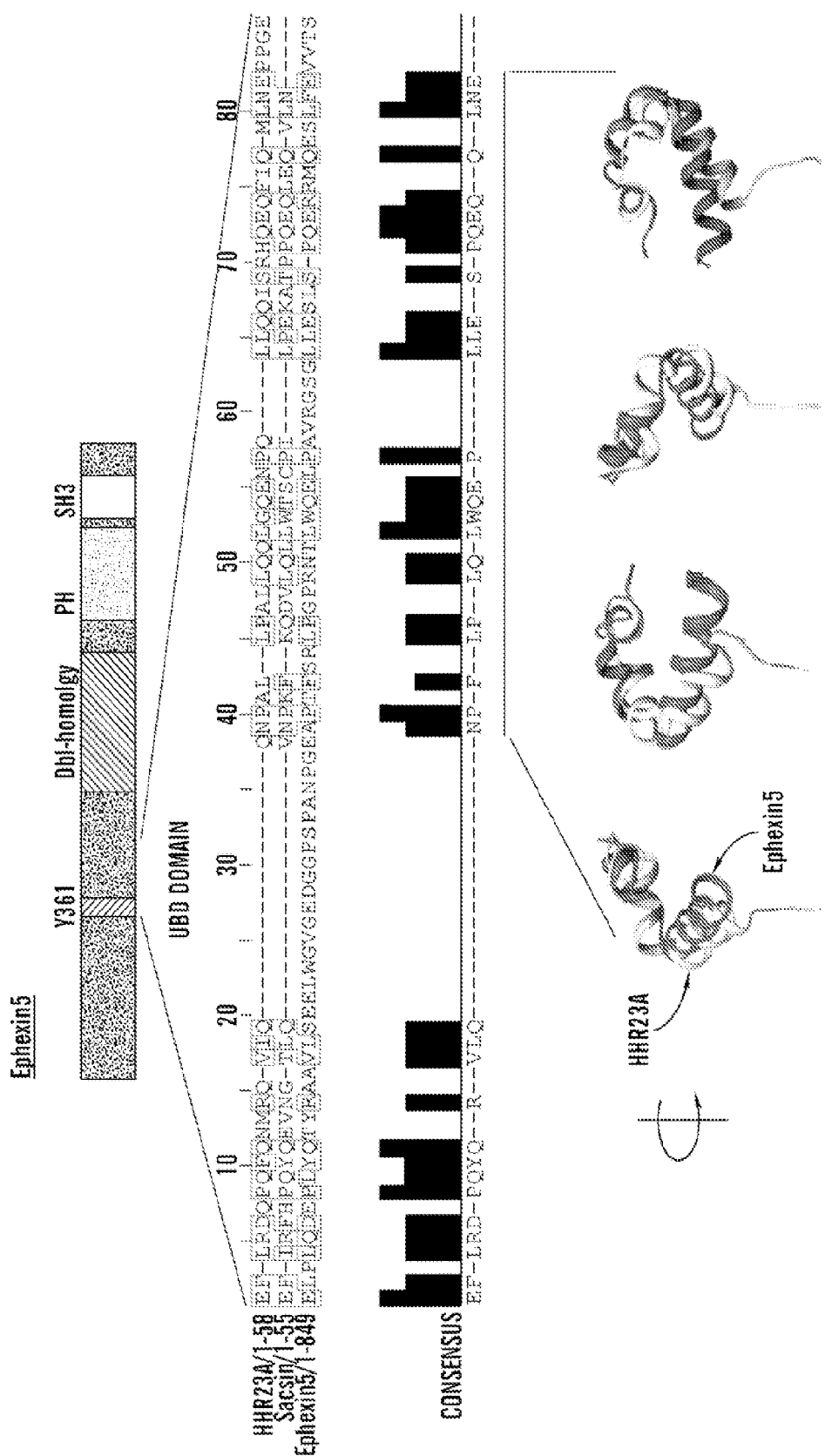
FIG. 14 shows the Ephexin5 Ube3A binding domain (UBD). Schematic of Ephexin5 showing Dbl-homology (GEF) domain, PH domain, SH3 domain, and Y361 phosphorylation site followed by location of predicted UBD. Comparing Ephexin5 to HHR23A through protein sequence alignment programs, ClustalW (which can be accessed on the web at www.ebi.ac.uk/Tools/clustalw2/index.html) and ModBase (which can be accessed on the web at modbase.compbio.ucsf.edu/modbase-cgi/search_form.cgi), inventors discovered a UBD in Ephexin5, consistent with its predicted tertiary structure. Sequences are EFLRDQPQFQNMRQVIQQNPALL-PALLQQLGQENPQLLQQISRHQEQFIQMLNEPPG E (SEQ ID NO: 14, HHR32A/1-58), EFIRFH-PQYQEVNGTLQVNPKFKQDVLQLL-WTSCPILPEKATPPQEQLEQVLN (SEQ ID NO: 15, Sacsin/1-55), ELPLQDEPLYQTYRAAVLSEEL-WGVGEDGGPSPANPGEAPTFSRLPGPRNTLWQELP AVRGSGLLESLSPQERRMQESLFEVVTS (SEQ ID NO: 16, Ephexin5/1-849), and EFLRDPQYQRVLQNPFLPLQL-WQEPLLESPQEQQLNE (SEQ ID NO: 17, consensus).

During proteasome-dependent degradation of proteins, specificity is conferred by E3 ligases or E2 conjugating enzymes that recognize the substrate to be degraded. The E3 ligase binds to the substrate and catalyzes the addition of polyubiquitin side chains to the substrate thereby promoting degradation via the proteasome (Hershko and Ciechanover, 1998). The inventors considered several E3 ligases that have recently been implicated in synapse development as candidate E3 ligases that catalyze Ephexin5 degradation. One of these E3 ligases, Cbl-b, has previously been implicated in the degradation of EphAs and EphBs (Fasen et al., 2008; Sharfe et al., 2003). A second E3 ligase, Ube3A, has been shown to regulate synapse number. To determine if Ube3A and/or Cbl-b catalyze Ephexin5 degradation the inventors first asked if either of these E3 ligases interacts with and degrades Ephexin5 in HEK293T cells. When these E3 ligases were epitope-tagged and expressed in HEK293T cells together with Ephexin5 the inventors found that Ephexin5 co-immunoprecipitates with Ube3A but not with Cbl-b (FIG. 7A). The coimmunoprecipitation of Ube3A with Ephexin5 was specific in that Ube3A was not coimmunoprecipitated with two other neuronal proteins, the Ephexin family member Ephexin1 or the transcription factor MEF2. In a previous study the inventors had shown that Ube3A binds to substrates via a Ube3A binding domain (hereafter referred to as UBD (Greer et al., 2010). Using protein sequence alignment programs, ClustalW and ModBase, the inventors identified a UBD in Ephexin5, providing further support for the idea that Ephexin5 might be a substrate of Ube3A (FIG. 14). Consistent with this hypothesis, the inventor found that the level of Ephexin5 expression was reduced in HEK293T cells co-transfected with Ube3A compared to cells co-transfected with Cblb (FIG. 7B).

Figure 7C:
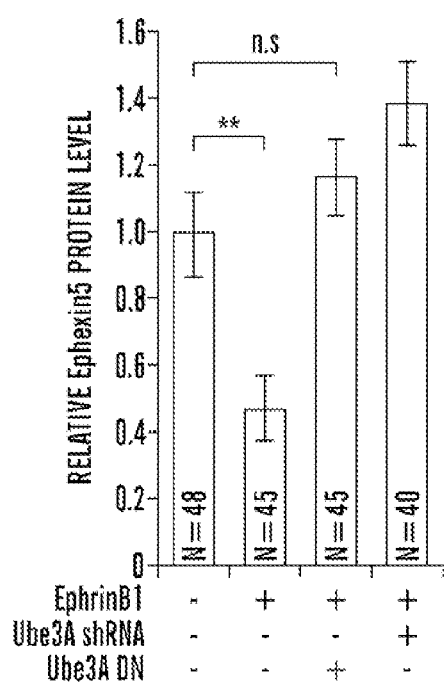
Figure 7D:
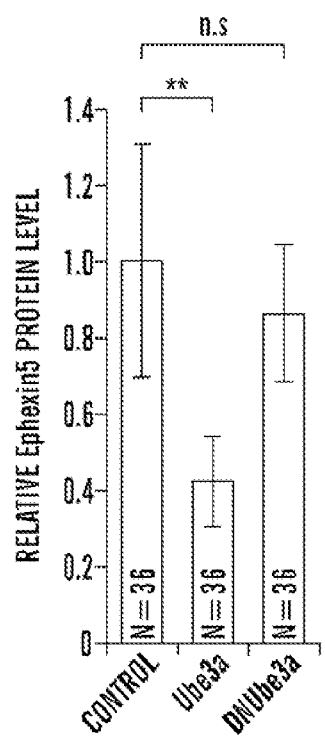

The inventors next asked whether EphrinB1/EphB-mediated Ephexin5 degradation in neurons is catalyzed by Ube3A. To inhibit Ube3A activity the inventors introduced into neurons a dominant interfering form of Ube3A (dnUbe3A) that contained a mutation in the ubiquitin ligase domain rendering Ube3A inactive. The inventors had previously shown that even though dnUbe3A is catalytically inactive it still binds to E2 ligases and to its substrates and functions in a dominant negative manner to block the ability of wild type Ube3A to ubiquitinate its substrates (Greer et al., 2010). The inventors found that when introduced into HEK293T cells dnUbe3A bound to Ephexin5 (FIG. 7A). They also found by immunofluorescence microscopy that when overexpressed in neurons, dnUbe3A, but not WT Ube3A, blocked EphrinB1/EphB stimulation of Ephexin5 degradation (FIG. 7C). EphrinB/EphB stimulation of Ephexin5 degradation was also attenuated when Ube3A expression was knocked down by a shRNA that specifically targets the Ube3A mRNA (FIG. 7C, Greer et al., 2010). Notably, the presence of the dnUbe3A did not affect Ephexin5 expression in neurons in the absence of EphrinB stimulation, indicating that EphrinB stimulation of Ephexin5 Y361 phosphorylation may be required for Ube3A-mediated degradation of Ephexin5 (FIG. 7D).

Figure 7G:
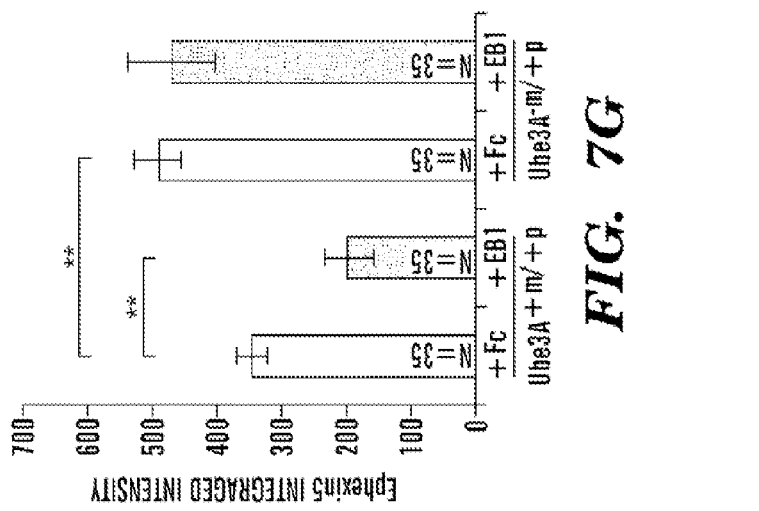
Figure 7F:
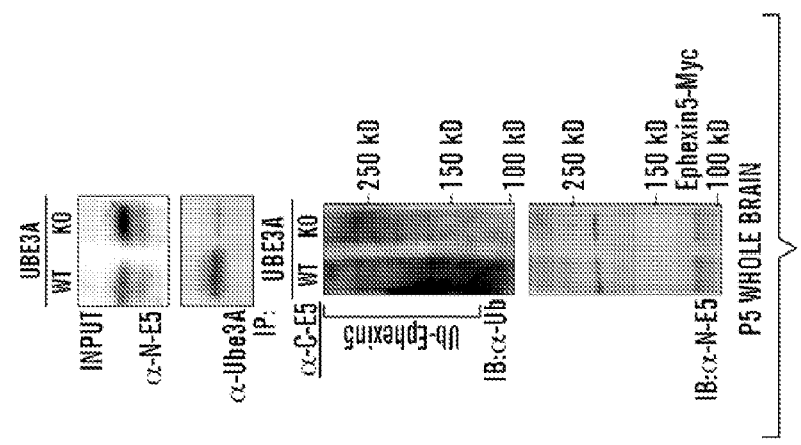
Figure 7E:
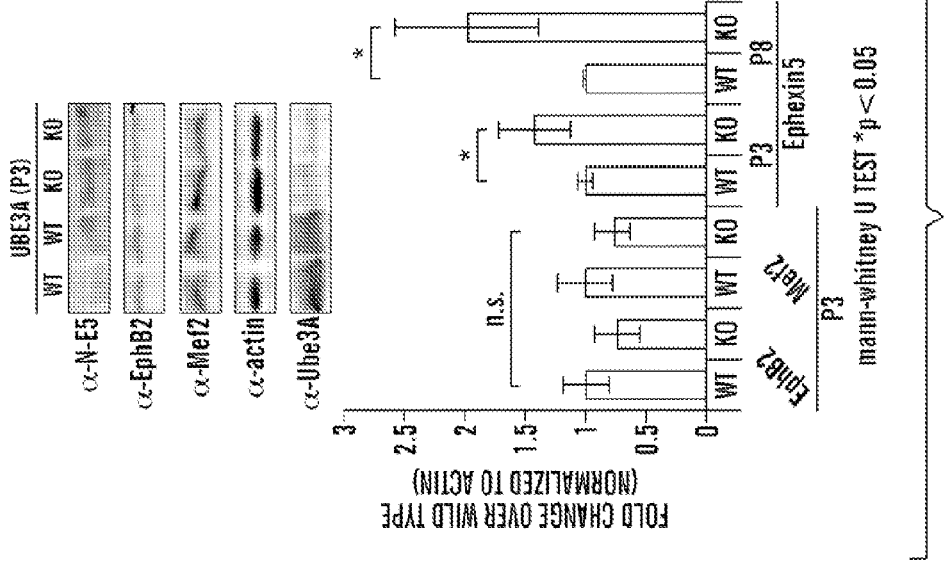

To begin to determine if Ube3A-dependent degradation of Ephexin5 might be relevant to the etiology of Angelman syndrome the invnetors asked if the absence of Ube3A in a mouse model of Angelman syndrome affects the level of Ephexin5 expression in the brain. Towards this end, they analyzed the level of Ephexin5 protein expression in the brains of wild type mice and compared the level of Ephexin5 protein to that expressed in the brains of mice in which the maternally inherited Ube3A was disrupted (Ube3A$^{m-/p+}$). Because the paternally inherited copy of Ube3A is silenced in the brain due to imprinting, the level of Ube3A expression in Ube3A$^{m-/p+}$ neurons is very low. The inventors found that the level of Ephexin5 expression in the brains of Ube3A$^{m-/p+}$ mice was significantly higher than that detected in the brains of wild type mice (FIG. 7E). Moreover, the level of ubiquitinated Ephexin5 in brains of Ube3A$^{m-/p+}$ mice was significantly reduced compared to the brains of litter mate controls (FIG. 7F). In addition the inventors found that when neurons from wild type and Ube3A$^{m-/p+}$ brains were cultured and then treated with EphrinB1 the level of Ephexin5 protein was reduced upon EphrinB1 treatment in wild type but not in Ube3A$^{m-/p+}$ neurons (FIG. 7G). Taken together, these findings indicate that in response to EphrinB treatment Ephexin5 is tyrosine phosphorylated by an EphB-dependent mechanism, and that this leads to Ephexin5 degradation by a Ube3A-dependent mechanism. Accordingly, if Ephexin5 degradation is disrupted due to a loss of Ube3A as occurs in Angelman syndrome the result is an increase in Ephexin5 expression and possibly a disruption of the proper control of excitatory synapse number during brain development.

Discussion

Figure 15A:
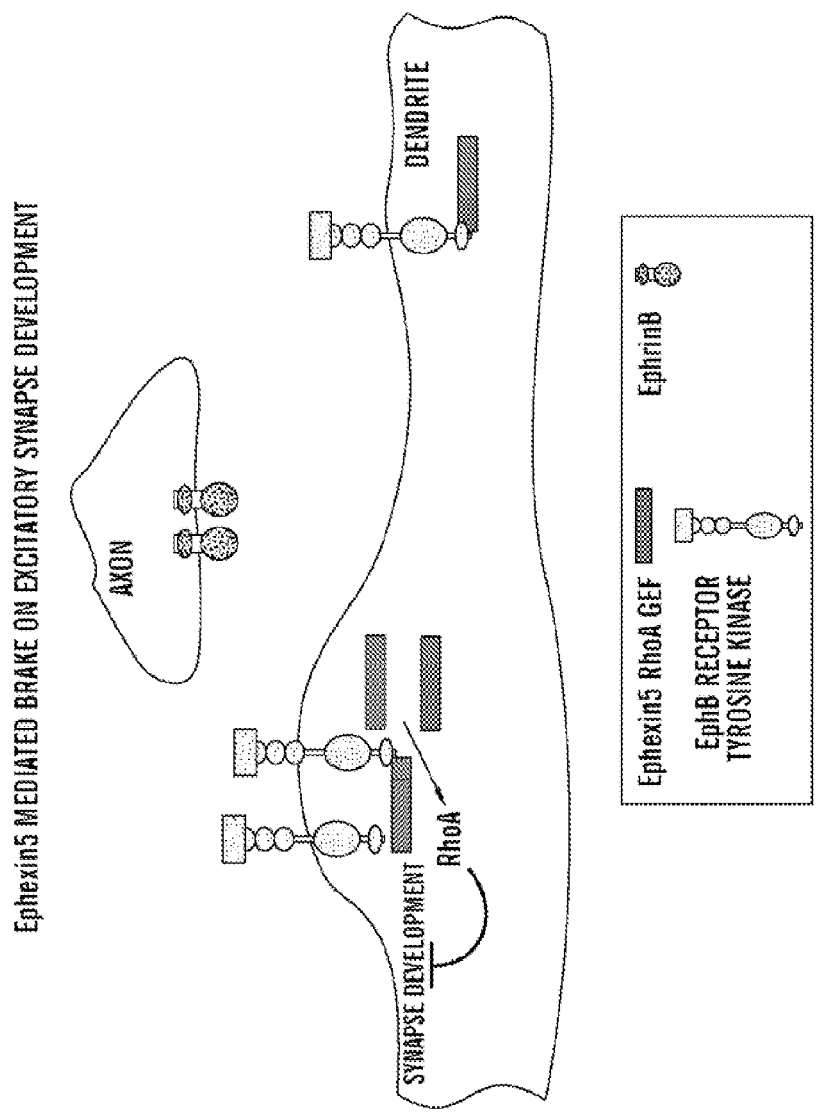
FIGS. 15A and 15B show a model of EphB- and Ephexin5-dependent synapse formation.
Figure 15B:
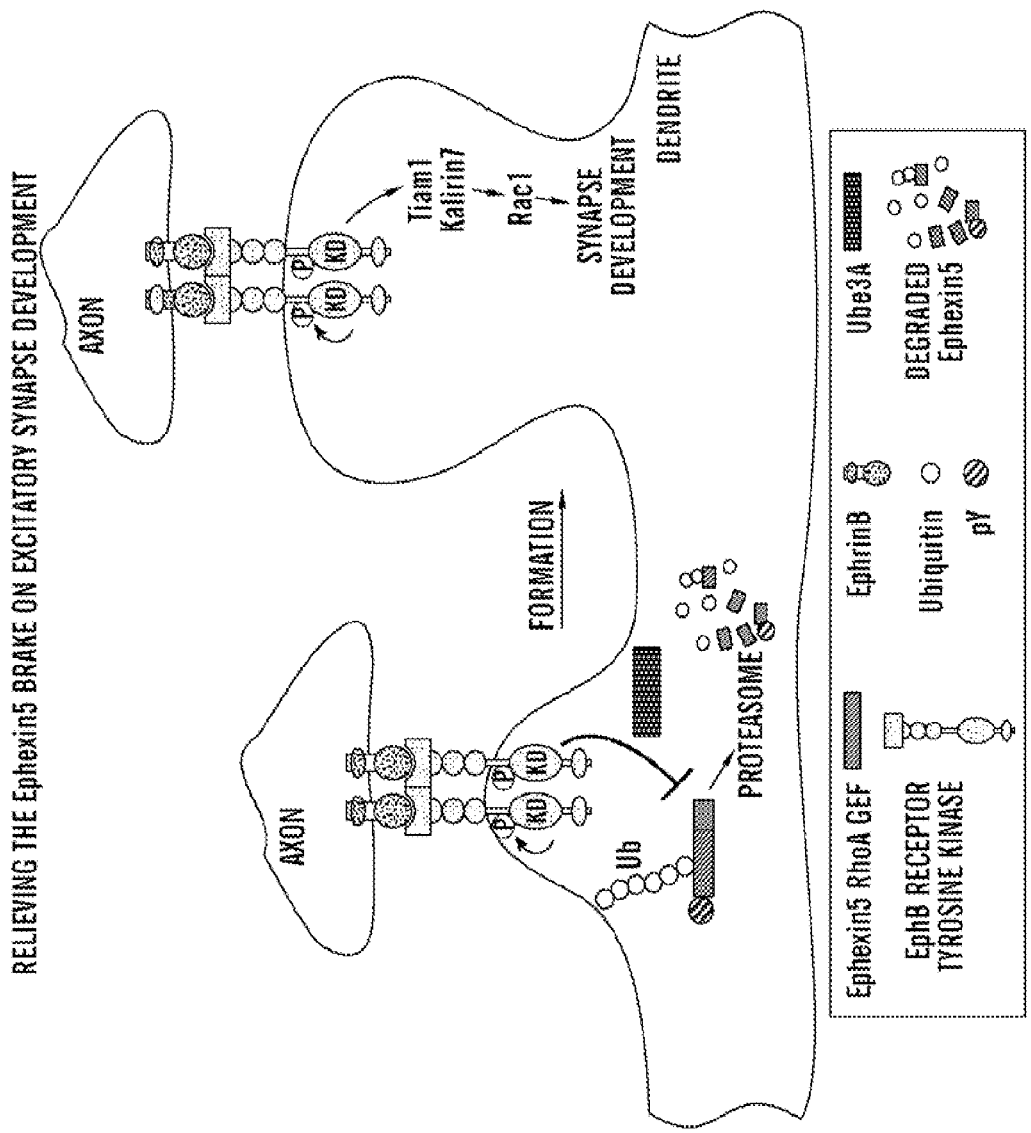

Previous studies have revealed a key role for EphrinB/EphB signaling in the development of excitatory synapses (Klein, 2009). However, the regulatory constraints that temper EphB-dependent synapse development so that excitatory synapses form at the right time and place, and in the correct number were not known. In this study, the inventors have discovered a RhoA GEF, Ephexin5, which functions to restrict EphB-dependent excitatory synapse development. Without wishing to be bound by a theory, Ephexin5 interacts with EphB prior to EphrinB binding, and by activating RhoA serves to inhibit synapse development. The binding of EphrinB to EphB as synapses form triggers the phosphorylation and degradation of Ephexin5 by a Ube3A-dependent mechanism. The reduction in Ephexin5 expression can then allow EphB to promote excitatory synapse development by activating Rac and other components of the synapse (FIG. 15).

The discovery that Ephexin5 functions to restrict excitatory synapse number indicates that, even though EphB is well known to promote excitatory synapse development, there are constraints on the activity of EphB so that synapse number is effectively controlled. Witkhout wishing to be bound by theory, there are several steps in the process of synapse development where Ephexin5 may function to restrict synapse number. Ephexin5 can function early in development as a barrier to excitatory synapse formation by activating RhoA and restricting the motility or growth of dendritic filopodia that are the sites of contact by the presynaptic neuron. For example, by inhibiting dendritic filopodia formation or motility, Ephexin5 may decrease the number of contacts the filopodia make with the presynaptic neuron, thus resulting in the formation of fewer synapses. This can explain why the knocking out of Ephexin5 function, or the degradation of Ephexin5 in response to EphrinB stimulation, leads to an increase in excitatory synapse number. In addition to or alternatively, Ephexin5 functions to restrict synapse number later in development perhaps to counterbalance the positive effects of EphB on Rac that promote dendritic spine development. An additional possibility is that Ephexin5 functions after excitatory synapse development as a regulator of synapse elimination.

Without wishing to be bound by a particular mechanistic model, the inventors' analyses of Ephexin5 function are most consistent with the possibility that Ephexin5 functions early in the process of synapse development. First, the inventors found that Ephexin5 is expressed, active, and bound to EphB prior to synapse formation. Second, the interaction of EphrinB with EphB, a process that is thought to be an early step in excitatory synapse development, triggers the degradation of Ephexin5. Third, time-lapse imaging studies indicate that Ephexin5 is localized to newly formed filopodia prior to synapse development where it appears to restrict filopodia motility and growth (Margolis et al. unpublished). As discussed above, Ephexin5 might function as an initial barrier to synapse formation until it is degraded upon EphrinB binding to EphB.

Without wishing to be bound by a theory, through its interaction with EphB, Ephexin5 marks the sites where synapses will form, and that the degradation of Ephexin5 is a critical early step in excitatory synapse development. While the biochemical mechanisms by which Ephexin5 is degraded are not fully understood, the inventors discovered that the ubiquitin E3 ligase Ube3A functions in this process. The inventors discovered that Ube3A interacts with and degrades Ephexin5, and that disrupting Ube3A function in neurons leads to enhanced levels of Ephexin5 expression. The inventors' data indicates that the phosphorylation of the N-terminus of Ephexin5 at Y361 triggers the Ube3A-mediated proteasomal degradation of Ephexin5. Again, without wishing to be bound by a theory, prior to Y361 phosphorylation, the N- and C-terminal portions of Ephexin5 interact, thereby protecting Ephexin5 from degradation. The phosphorylation of Ephexin5 at Y361 may relieve this inhibitory constraint allowing for Ephexin5 ubiquitination and degradation. A similar mechanism has been shown to regulate the activation of the Rac GEF Vav, a GEF that the inventors have previously shown to regulate the endocytosis of EphA receptors during axon guidance (Aghazadeh et al., 2000; Cowan et al., 2005). During EphrinA/EphA signaling it has been proposed that Vav-mediated endocytosis of the EphrinA/EphA complex may allow the conversion of the initial adhesive interaction between EphrinA and EphA-expressing cells into a repulsive interaction that results in growth cone collapse and axon repulsion. It is possible that Ephexin5 has a related function during EphB signaling at synapses. Typically the EphrinB/EphB interaction is thought to be repulsive. This has been well documented in studies of EphB's role in the process of axon guidance (Egea and Klein, 2007; Flanagan and Vanderhaeghen, 1998). However, during synapse development the EphrinB/EphB interaction is thought to result in synapse formation, a process that requires an interaction between the developing pre- and post-synaptic specialization. Without wishing to be bound by theory, when EphrinB and EphB mediate the interaction between the incoming axon and the developing dendrite, the interaction can be facilitated by the degradation of Ephexin5 by Ube3A. Since Ephexin5 is a RhoA GEF, its presence may initially lead to repulsion between the incoming axon and the dendrite. However, the EphB-dependent degradation of Ephexin5 can convert this initial repulsive interaction into an attractive one.

The finding that Ube3A is the ubiquitin ligase that controls EphB-mediated Ephexin5 degradation is of considerable interest given the role of Ube3A in human cognitive disorders such as Angelman syndrome and autism. The absence of Ube3A function in Angelman syndrome would be predicted to result in an increase in Ephexin5 protein expression, and thus a decrease in EphB-dependent synapse formation. Consistent with this, the inventors found in a mouse model for Angelman syndrome that the level of Ephexin5 protein expression is elevated and that in response to EphrinB treatment Ephexin5 is not degraded. Likewise, several studies have indicated that synapse development and function is disrupted in these mice (Cooper et al., 2004; Dindot et al., 2008; Jiang et al., 1998; Yashiro et al., 2009).

The recent finding that the Ube3A gene lies within a region of chromosome 15 that is sometimes duplicated in autism raises the possibility that altered levels of Ephexin5 and the resulting defects in excitatory synapse restriction might also be a mechanism relevant to the etiology of autism (Glessner et al., 2009). Accordingly, the inventors' discovery that reduced levels of Ube3A activity restores the level of Ephexin5 expression can be used in the treatment of disorders such as Angelman syndrome and autism.

REFERENCES

1. Aghazadeh, B., Lowry, W. E., Huang, X. Y., and Rosen, M. K. (2000). Structural basis for relief of autoinhibition of the Dbl homology domain of proto-oncogene Vav by tyrosine phosphorylation. Cell 102, 625-633.
2. Cabo, L., Cinque, C., Patane, M., Schillaci, D., Battaglia, G., Melchiorri, D., Nicoletti, F., and Bruno, V. (2006). Interaction between ephrins/Eph receptors and excitatory amino acid receptors: possible relevance in the regulation of synaptic plasticity and in the pathophysiology of neuronal degeneration. J Neurochem 98, 1-10.
3. Contractor, A., Rogers, C., Maron, C., Henkemeyer, M., Swanson, G. T., and Heinemann, S. F.
4. (2002). Trans-synaptic Eph receptor-ephrin signaling in hippocampal mossy fiber LTP. Science 296, 1864-1869.
5. Cooper, E. M., Hudson, A. W., Amos, J., Wagstaff, J., and Howley, P. M. (2004). Biochemical analysis of Angelman syndrome-associated mutations in the E3 ubiquitin ligase E6-associated protein. J Biol Chem 279, 41208-41217.
6. Cowan, C. W., Shao, Y. R., Sahin, M., Shamah, S. M., Lin, M. Z., Greer, P. L., Gao, S., Griffith, E. C., Brugge, J. S., and Greenberg, M. E. (2005). Vav family GEFs link activated Ephs to endocytosis and axon guidance. Neuron 46, 205-217.
7. Dalva, M. B., McClelland, A. C., and Kayser, M. S. (2007). Cell adhesion molecules: signalling functions at the synapse. Nat Rev Neurosci 8, 206-220.
8. Dalva, M. B., Takasu, M. A., Lin, M. Z., Shamah, S. M., Hu, L., Gale, N. W., and Greenberg, M. E. (2000). EphB receptors interact with NMDA receptors and regulate excitatory synapse formation. Cell 103, 945-956.
9. Dindot, S. V., Antalffy, B. A., Bhattacharjee, M. B., and Beaudet, A. L. (2008). The Angelman syndrome ubiquitin ligase localizes to the synapse and nucleus, and maternal deficiency results in abnormal dendritic spine morphology. Hum Mol Genet 17, 111-118.
10. Egea, J., and Klein, R. (2007). Bidirectional Eph-ephrin signaling during axon guidance. Trends Cell Biol 17, 230-238.
11. Ethell, I. M., Irie, F., Kalo, M. S., Couchman, J. R., Pasquale, E. B., and Yamaguchi, Y. (2001). EphB/syndecan-2 signaling in dendritic spine morphogenesis. Neuron 31, 1001-1013.
12. Fasen, K., Cerretti, D. P., and Huynh-Do, U. (2008). Ligand binding induces Cbl-dependent EphB1 receptor degradation through the lysosomal pathway. Traffic 9, 251-266.
13. Flanagan, J. G., and Vanderhaeghen, P. (1998). The ephrins and Eph receptors in neural development. Annu Rev Neurosci 21, 309-345.
14. Flavell, S. W., Cowan, C. W., Kim, T. K., Greer, P. L., Lin, Y., Paradis, S., Griffith, E. C., Hu, L. S., Chen, C., and Greenberg, M. E. (2006). Activity-dependent regulation of MEF2 transcription factors suppresses excitatory synapse number. Science 311, 1008-1012.
15. Fu, W. Y., Chen, Y., Sahin, M., Zhao, X. S., Shi, L., Bikoff, J. B., Lai, K. O., Yung, W. H., Fu, A. K., Greenberg, M. E., et al. (2007). Cdk5 regulates EphA4-mediated dendritic spine retraction through an ephexin1-dependent mechanism. Nat Neurosci 10, 67-76.
16. Glessner, J. T., Wang, K., Cai, G., Korvatska, O., Kim, C. E., Wood, S., Zhang, H., Estes, A., Brune, C. W., Bradfield, J. P., et al. (2009). Autism genome-wide copy number variation reveals ubiquitin and neuronal genes. Nature 459, 569-573.
17. Greer, P. L., and Greenberg, M. E. (2008). From synapse to nucleus: calcium-dependent gene transcription in the control of synapse development and function. Neuron 59, 846-860.
18. Greer, P. L., Hanayama, R., Bloodgood, B. L., Mardinly, A. R., Lipton, D. M., Flavell, S. W., Kim, T. K., Griffith, E. C., Waldon, Z., Maehr, R., et al. The Angelman Syndrome protein Ube3A regulates synapse development by ubiquitinating arc. Cell 140, 704-716.
19. Grunwald, I. C., Korte, M., Adelmann, G., Plueck, A., Kullander, K., Adams, R. H., Frotscher, M., Bonhoeffer, T., and Klein, R. (2004). Hippocampal plasticity requires postsynaptic ephrinBs. Nat Neurosci 7, 33-40.
20. Grunwald, I. C., Korte, M., Wolfer, D., Wilkinson, G. A., Unsicker, K., Lipp, H. P., Bonhoeffer, T., and Klein, R. (2001). Kinase-independent requirement of EphB2 receptors in hippocampal synaptic plasticity. Neuron 32, 1027-1040.
21. Henkemeyer, M., Itkis, O. S., Ngo, M., Hickmott, P. W., and Ethell, I. M. (2003). Multiple EphB receptor tyrosine kinases shape dendritic spines in the hippocampus. J Cell Biol 163, 13131326.
22. Hershko, A., and Ciechanover, A. (1998). The ubiquitin system. Annu Rev Biochem 67, 425479.
23. Jiang, Y. H., Armstrong, D., Albrecht, U., Atkins, C. M., Noebels, J. L., Eichele, G., Sweatt, J. D., and Beaudet, A. L. (1998). Mutation of the Angelman ubiquitin ligase in mice causes increased cytoplasmic p53 and deficits of contextual learning and long-term potentiation. Neuron 21, 799811.
24. Jontes, J. D., Buchanan, J., and Smith, S. J. (2000). Growth cone and dendrite dynamics in zebrafish embryos: early events in synaptogenesis imaged in vivo. Nat Neurosci 3, 231-237.
25. Kayser, M. S., McClelland, A. C., Hughes, E. G., and Dalva, M. B. (2006). Intracellular and trans-synaptic regulation of glutamatergic synaptogenesis by EphB receptors. J Neurosci 26, 1215212164.
26. Kayser, M. S., Nolt, M. J., and Dalva, M. B. (2008). EphB receptors couple dendritic filopodia motility to synapse formation. Neuron 59, 56-69.
27. Kishino, T., Lalande, M., and Wagstaff, J. (1997). UBE3A/E6-AP mutations cause Angelman syndrome. Nat Genet 15, 70-73.
28. Klein, R. (2009). Bidirectional modulation of synaptic functions by Eph/ephrin signaling. Nat Neurosci 12, 15-20.
29. Kopec, C. D., Li, B., Wei, W., Boehm, J., and Malinow, R. (2006). Glutamate receptor exocytosis and spine enlargement during chemically induced long-term potentiation. J Neurosci 26, 20002009.
30. Lai, K. O., and Ip, N. Y. (2009). Synapse development and plasticity: roles of ephrin/Eph receptor signaling. Curr Opin Neurobiol 19, 275-283.
31. Lim, B. K., Matsuda, N., and Poo, M. M. (2008). Ephrin-B reverse signaling promotes structural and functional synaptic maturation in vivo. Nat Neurosci 11, 160-169.
32. Lin, Y., Bloodgood, B. L., Hauser, J. L., Lapan, A. D., Koon, A. C., Kim, T. K., Hu, L. S., Malik, A. N., and Greenberg, M. E. (2008). Activity-dependent regulation of inhibitory synapse development by Npas4. Nature 455, 1198-1204.
33. Lois, C., Hong, E. J., Pease, S., Brown, E. J., and Baltimore, D. (2002). Germline transmission and tissue-specific expression of transgenes delivered by lentiviral vectors. Science 295, 868872.
34. Matsuzaki, M., Honkura, N., Ellis-Davies, G. C., and Kasai, H. (2004). Structural basis of long-term potentiation in single dendritic spines. Nature 429, 761-766.
35. Micheva, K. D., and Smith, S. J. (2007). Array tomography: a new tool for imaging the molecular architecture and ultrastructure of neural circuits. Neuron 55, 25-36.
36. Murai, K. K., Nguyen, L. N., Irie, F., Yamaguchi, Y., and Pasquale, E. B. (2003). Control of hippocampal dendritic spine morphology through ephrin-A3/EphA4 signaling. Nat Neurosci 6, 153-160.
37. Ogita, H., Kunimoto, S., Kamioka, Y., Sawa, H., Masuda, M., and Mochizuki, N. (2003). EphA4mediated Rho activation via Vsm-RhoGEF expressed specifically in vascular smooth muscle cells. Circ Res 93, 23-31.
38. Pak, D. T., Yang, S., Rudolph-Correia, S., Kim, E., and Sheng, M. (2001). Regulation of dendritic spine morphology by SPAR, a PSD-95-associated RapGAP. Neuron 31, 289-303.
39. Paradis, S., Harrar, D. B., Lin, Y., Koon, A. C., Hauser, J. L., Griffith, E. C., Zhu, L., Brass, L. F., Chen, C., and Greenberg, M. E. (2007). An RNAi-based approach identifies molecules required for glutamatergic and GABAergic synapse development. Neuron 53, 217-232.
40. Penzes, P., Beeser, A., Chernoff, J., Schiller, M. R., Eipper, B. A., Mains, R. E., and Huganir, R. L.
41. (2003). Rapid induction of dendritic spine morphogenesis by trans-synaptic ephrinB-EphB receptor activation of the Rho-GEF kalirin. Neuron 37, 263-274.
42. Rossman, K. L., Der, C. J., and Sondek, J. (2005). GEF means go: turning on RHO GTPases with guanine nucleotide-exchange factors. Nat Rev Mol Cell Biol 6, 167-180.
43. Sahin, M., Greer, P. L., Lin, M. Z., Poucher, H., Eberhart, J., Schmidt, S., Wright, T. M., Shamah, S. M., O'Connell, S., Cowan, C. W., et al. (2005). Eph-dependent tyrosine phosphorylation of ephexin1 modulates growth cone collapse. Neuron 46, 191-204.
44. Schaeren-Wiemers, N., and Gerfin-Moser, A. (1993). A single protocol to detect transcripts of various types and expression levels in neural tissue and cultured cells: in situ hybridization using digoxigenin-labelled cRNA probes. Histochemistry 100, 431-440.
45. Shamah, S. M., Lin, M. Z., Goldberg, J. L., Estrach, S., Sahin, M., Hu, L., Bazalakova, M., Neve, R. L., Corfas, G., Debant, A., et al. (2001). EphA receptors regulate growth cone dynamics through the novel guanine nucleotide exchange factor ephexin. Cell 105, 233-244.
46. Sharfe, N., Freywald, A., Toro, A., and Roifman, C. M. (2003). Ephrin-A1 induces c-Cbl phosphorylation and EphA receptor down-regulation in T cells. J Immunol 170, 6024-6032.
47. Snyder, J. T., Worthylake, D. K., Rossman, K. L., Betts, L., Pruitt, W. M., Siderovski, D. P., Der, C. J., and Sondek, J. (2002). Structural basis for the selective activation of Rho GTPases by Dbl exchange factors. Nat Struct Biol 9, 468-475.
48. Stoppini, L., Buchs, P. A., and Muller, D. (1991). A simple method for organotypic cultures of nervous tissue. J Neurosci Methods 37, 173-182.
49. Takasu, M. A., Dalva, M. B., Zigmond, R. E., and Greenberg, M. E. (2002). Modulation of NMDA receptor-dependent calcium influx and gene expression through EphB receptors. Science 295, 491-495.
50. Tashiro, A., Minden, A., and Yuste, R. (2000). Regulation of dendritic spine morphology by the rho family of small GTPases: antagonistic roles of Rac and Rho. Cereb Cortex 10, 927-938.
51. Tolias, K. F., Bikoff, J. B., Burette, A., Paradis, S., Harrar, D., Tavazoie, S., Weinberg, R. J., and Greenberg, M. E. (2005). The Rac1-GEF Tiam1 couples the NMDA receptor to the activity-dependent development of dendritic arbors and spines. Neuron 45, 525-538.
52. Tolias, K. F., Bikoff, J. B., Kane, C. G., Tolias, C. S., Hu, L., and Greenberg, M. E. (2007). The Rac1 guanine nucleotide exchange factor Tiam1 mediates EphB receptor-dependent dendritic spine development. Proc Natl Acad Sci USA 104, 7265-7270.
53. Xia, Z., Dudek, H., Miranti, C. K., and Greenberg, M. E. (1996). Calcium influx via the NMDA receptor induces immediate early gene transcription by a MAP kinase/ERK-dependent mechanism. J Neurosci 16, 5425-5436.
54. Yashiro, K., Riday, T. T., Condon, K. H., Roberts, A. C., Bernardo, D. R., Prakash, R., Weinberg, R. J., Ehlers, M. D., and Philpot, B. D. (2009). Ube3a is required for experience-dependent maturation of the neocortex. Nat Neurosci 12, 777-783.
55. Yen, H. C., Xu, Q., Chou, D. M., Zhao, Z., and Elledge, S. J. (2008). Global protein stability profiling in mammalian cells. Science 322, 918-923.
56. Ziv, N. E., and Smith, S. J. (1996). Evidence for a role of dendritic filopodia in synaptogenesis and spine formation. Neuron 17, 91-102.

All patents and other publications identified in the specification are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

We claim:

1. A method of promoting spine-excitatory synapse formation, the method comprising decreasing the level of Ephexin5 or inhibiting the activity of Ephexin 5 in a neuron comprising contacting the neuron with an Ephexin5 inhibitor, wherein the inhibitor is a nucleic acid.

2. The method of claim 1, wherein the nucleic acid is an antisense oligonucleotide, an aptamer, a siRNA, a shRNA, or a ribozym.

3. The method of claim 1, wherein the nucleic acid is a shRNA comprising a nucleotide sequence selected from the group consisting of TAGCCGCCTTATGGATACAAA (SEQ ID NO: 11, Ephexin5 shRNA 5"), CCCTGCAGGACGAAC-CTTTAT (SEQ ID NO: 12, Ephexin5 shRNA 6"), and TCCGAAAGCACTTCCTCAAAT (SEQ ID NO: 13, Ephexin5 shRNA 7").

4. The method of claim 1, wherein said contacting is in vitro.

5. The method of claim 1, wherein said activity is RhoA GEF activity of Ephexin5.

* * * * *

SEQUENCE LISTING

```
<160> NUMBER OF SEQ ID NOS: 20

<210> SEQ ID NO 1
<211> LENGTH: 12
<212> TYPE: PRT
<213> ORGANISM: Unknown
<220> FEATURE:
<223> OTHER INFORMATION: Description of Unknown: DH domain
      peptide from Ephexin5

<400> SEQUENCE: 1

Phe Leu Leu Leu Pro Phe Gln Arg Ile Thr Arg Leu
1               5                   10

<210> SEQ ID NO 2
<211> LENGTH: 12
<212> TYPE: PRT
<213> ORGANISM: Unknown
<220> FEATURE:
<223> OTHER INFORMATION: Description of Unknown: DH domain
      peptide from NET1

<400> SEQUENCE: 2

Phe Leu Asp Ile Pro Arg Ser Arg Leu Val Lys Tyr
1               5                   10

<210> SEQ ID NO 3
<211> LENGTH: 12
<212> TYPE: PRT
<213> ORGANISM: Unknown
<220> FEATURE:
<223> OTHER INFORMATION: Description of Unknown: DH domain
      peptide from LARG

<400> SEQUENCE: 3

Ile Ile Pro Thr Gln Met Gln Arg Leu Thr Lys Tyr
1               5                   10

<210> SEQ ID NO 4
<211> LENGTH: 12
<212> TYPE: PRT
<213> ORGANISM: Unknown
<220> FEATURE:
<223> OTHER INFORMATION: Description of Unknown: DH domain
      peptide from TECH
```

-continued

```
<400> SEQUENCE: 4

Met Leu Ala Lys Pro His Gln Arg Leu Thr Lys Tyr
1               5                   10

<210> SEQ ID NO 5
<211> LENGTH: 12
<212> TYPE: PRT
<213> ORGANISM: Unknown
<220> FEATURE:
<223> OTHER INFORMATION: Description of Unknown: DH domain
      peptide from LBC

<400> SEQUENCE: 5

Cys Ile Leu Leu Val Thr Gln Arg Ile Thr Lys Tyr
1               5                   10

<210> SEQ ID NO 6
<211> LENGTH: 12
<212> TYPE: PRT
<213> ORGANISM: Unknown
<220> FEATURE:
<223> OTHER INFORMATION: Description of Unknown: DH domain
      peptide from DBS

<400> SEQUENCE: 6

Tyr Leu Leu Lys Pro Val Gln Arg Ile Thr Lys Tyr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (4)..(4)
<223> OTHER INFORMATION: Leu, Ile, Thr or Lys
<220> FEATURE:
<221> NAME/KEY: MOD_RES
<222> LOCATION: (6)..(6)
<223> OTHER INFORMATION: Phe, Arg, Met, His, Thr or Val
<220> FEATURE:
<221> NAME/KEY: MOD_RES
<222> LOCATION: (9)..(9)
<223> OTHER INFORMATION: Ile or Leu

<400> SEQUENCE: 7

Phe Leu Leu Xaa Pro Xaa Gln Arg Xaa Thr Lys Tyr
1               5                   10

<210> SEQ ID NO 8
<211> LENGTH: 22
<212> TYPE: PRT
<213> ORGANISM: Unknown
<220> FEATURE:
<223> OTHER INFORMATION: Description of Unknown: Ephexin1 tyrosine
      phosphorylation site peptide

<400> SEQUENCE: 8

Arg Asn Leu Ile Glu Gln Ile Gly Leu Leu Tyr Gln Thr Tyr Arg Asp
1               5                   10                  15

Lys Ser Thr Leu Gln Glu
            20

<210> SEQ ID NO 9
```

-continued

```
<211> LENGTH: 22
<212> TYPE: PRT
<213> ORGANISM: Unknown
<220> FEATURE:
<223> OTHER INFORMATION: Description of Unknown: Ephexin5 tyrosine
      phosphorylation site peptide

<400> SEQUENCE: 9

Trp Glu Leu Pro Leu Gln Asp Glu Pro Leu Tyr Gln Glu Tyr His Ala
1               5                   10                  15

Ala Val Leu Ser Glu Glu
            20

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Arg or Trp
<220> FEATURE:
<221> NAME/KEY: MOD_RES
<222> LOCATION: (2)..(2)
<223> OTHER INFORMATION: Asn or Glu
<220> FEATURE:
<221> NAME/KEY: MOD_RES
<222> LOCATION: (4)..(4)
<223> OTHER INFORMATION: Ile or Pro
<220> FEATURE:
<221> NAME/KEY: MOD_RES
<222> LOCATION: (5)..(5)
<223> OTHER INFORMATION: Glu or Leu
<220> FEATURE:
<221> NAME/KEY: MOD_RES
<222> LOCATION: (7)..(7)
<223> OTHER INFORMATION: Ile or Asp
<220> FEATURE:
<221> NAME/KEY: MOD_RES
<222> LOCATION: (8)..(8)
<223> OTHER INFORMATION: Gly or Glu
<220> FEATURE:
<221> NAME/KEY: MOD_RES
<222> LOCATION: (9)..(9)
<223> OTHER INFORMATION: Leu or Pro
<220> FEATURE:
<221> NAME/KEY: MOD_RES
<222> LOCATION: (13)..(13)
<223> OTHER INFORMATION: Thr or Glu
<220> FEATURE:
<221> NAME/KEY: MOD_RES
<222> LOCATION: (15)..(15)
<223> OTHER INFORMATION: Arg or His
<220> FEATURE:
<221> NAME/KEY: MOD_RES
<222> LOCATION: (16)..(16)
<223> OTHER INFORMATION: Asp or Ala
<220> FEATURE:
<221> NAME/KEY: MOD_RES
<222> LOCATION: (17)..(17)
<223> OTHER INFORMATION: Lys or Ala
<220> FEATURE:
<221> NAME/KEY: MOD_RES
<222> LOCATION: (18)..(18)
<223> OTHER INFORMATION: Ser or Val
<220> FEATURE:
<221> NAME/KEY: MOD_RES
<222> LOCATION: (19)..(19)
<223> OTHER INFORMATION: Thr or Leu
<220> FEATURE:
<221> NAME/KEY: MOD_RES
<222> LOCATION: (20)..(20)
<223> OTHER INFORMATION: Leu or Ser
```

```
<220> FEATURE:
<221> NAME/KEY: MOD_RES
<222> LOCATION: (21)..(21)
<223> OTHER INFORMATION: Gln or Glu

<400> SEQUENCE: 10

Xaa Xaa Leu Xaa Xaa Gln Xaa Xaa Xaa Leu Tyr Gln Xaa Tyr Xaa Xaa
1               5                   10                  15

Xaa Xaa Xaa Xaa Xaa Glu
            20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tagccgcctt atggatacaa a                                          21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ccctgcagga cgaaccttta t                                          21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tccgaaagca cttcctcaaa t                                          21

<210> SEQ ID NO 14
<211> LENGTH: 58
<212> TYPE: PRT
<213> ORGANISM: Unknown
<220> FEATURE:
<223> OTHER INFORMATION: Description of Unknown: HHR32A
      polypeptide

<400> SEQUENCE: 14

Glu Phe Leu Arg Asp Gln Pro Gln Phe Gln Asn Met Arg Gln Val Ile
1               5                   10                  15

Gln Gln Asn Pro Ala Leu Leu Pro Ala Leu Leu Gln Gln Leu Gly Gln
            20                  25                  30

Glu Asn Pro Gln Leu Leu Gln Gln Ile Ser Arg His Gln Glu Gln Phe
        35                  40                  45

Ile Gln Met Leu Asn Glu Pro Pro Gly Glu
    50                  55

<210> SEQ ID NO 15
<211> LENGTH: 53
<212> TYPE: PRT
```

```
<213> ORGANISM: Unknown
<220> FEATURE:
<223> OTHER INFORMATION: Description of Unknown: Sacsin
      polypeptide

<400> SEQUENCE: 15

Glu Phe Ile Arg Phe His Pro Gln Tyr Gln Glu Val Asn Gly Thr Leu
1               5                   10                  15

Gln Val Asn Pro Lys Phe Lys Gln Asp Val Leu Gln Leu Leu Trp Thr
            20                  25                  30

Ser Cys Pro Ile Leu Pro Glu Lys Ala Thr Pro Pro Gln Glu Gln Leu
        35                  40                  45

Glu Gln Val Leu Asn
    50

<210> SEQ ID NO 16
<211> LENGTH: 85
<212> TYPE: PRT
<213> ORGANISM: Unknown
<220> FEATURE:
<223> OTHER INFORMATION: Description of Unknown: Ephexin5
      polypeptide

<400> SEQUENCE: 16

Glu Leu Pro Leu Gln Asp Glu Pro Leu Tyr Gln Thr Tyr Arg Ala Ala
1               5                   10                  15

Val Leu Ser Glu Glu Leu Trp Gly Val Gly Glu Asp Gly Gly Pro Ser
            20                  25                  30

Pro Ala Asn Pro Gly Glu Ala Pro Thr Phe Ser Arg Leu Pro Gly Pro
        35                  40                  45

Arg Asn Thr Leu Trp Gln Glu Leu Pro Ala Val Arg Gly Ser Gly Leu
    50                  55                  60

Leu Glu Ser Leu Ser Pro Gln Glu Arg Arg Met Gln Glu Ser Leu Phe
65                  70                  75                  80

Glu Val Val Thr Ser
            85

<210> SEQ ID NO 17
<211> LENGTH: 86
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Phe or Leu
<220> FEATURE:
<221> NAME/KEY: MOD_RES
<222> LOCATION: (3)..(3)
<223> OTHER INFORMATION: May or may not be present
<220> FEATURE:
<221> NAME/KEY: MOD_RES
<222> LOCATION: (4)..(4)
<223> OTHER INFORMATION: Leu or Ile
<220> FEATURE:
<221> NAME/KEY: MOD_RES
<222> LOCATION: (5)..(5)
<223> OTHER INFORMATION: Arg or Gln
<220> FEATURE:
<221> NAME/KEY: MOD_RES
<222> LOCATION: (6)..(6)
<223> OTHER INFORMATION: Asp or Phe
<220> FEATURE:
<221> NAME/KEY: MOD_RES
<222> LOCATION: (7)..(7)
```

```
<223> OTHER INFORMATION: Gln, His or Glu
<220> FEATURE:
<221> NAME/KEY: MOD_RES
<222> LOCATION: (9)..(9)
<223> OTHER INFORMATION: Gln or Leu
<220> FEATURE:
<221> NAME/KEY: MOD_RES
<222> LOCATION: (10)..(10)
<223> OTHER INFORMATION: Phe or Tyr
<220> FEATURE:
<221> NAME/KEY: MOD_RES
<222> LOCATION: (12)..(12)
<223> OTHER INFORMATION: Asn, Glu or Thr
<220> FEATURE:
<221> NAME/KEY: MOD_RES
<222> LOCATION: (13)..(13)
<223> OTHER INFORMATION: Met, Val or Tyr
<220> FEATURE:
<221> NAME/KEY: MOD_RES
<222> LOCATION: (14)..(14)
<223> OTHER INFORMATION: Arg or Asn
<220> FEATURE:
<221> NAME/KEY: MOD_RES
<222> LOCATION: (15)..(15)
<223> OTHER INFORMATION: Gln, Gly or Ala
<220> FEATURE:
<221> NAME/KEY: MOD_RES
<222> LOCATION: (16)..(16)
<223> OTHER INFORMATION: May or may not be present
<220> FEATURE:
<221> NAME/KEY: MOD_RES
<222> LOCATION: (17)..(17)
<223> OTHER INFORMATION: Val or Thr
<220> FEATURE:
<221> NAME/KEY: MOD_RES
<222> LOCATION: (18)..(18)
<223> OTHER INFORMATION: Ile or Leu
<220> FEATURE:
<221> NAME/KEY: MOD_RES
<222> LOCATION: (19)..(19)
<223> OTHER INFORMATION: Gln or Ser
<220> FEATURE:
<221> NAME/KEY: MOD_RES
<222> LOCATION: (20)..(37)
<223> OTHER INFORMATION: May or may not be present
<220> FEATURE:
<221> NAME/KEY: MOD_RES
<222> LOCATION: (38)..(38)
<223> OTHER INFORMATION: Gln, Val or Glu
<220> FEATURE:
<221> NAME/KEY: MOD_RES
<222> LOCATION: (39)..(39)
<223> OTHER INFORMATION: Asn or Ala
<220> FEATURE:
<221> NAME/KEY: MOD_RES
<222> LOCATION: (41)..(41)
<223> OTHER INFORMATION: Ala, Lys or Thr
<220> FEATURE:
<221> NAME/KEY: MOD_RES
<222> LOCATION: (42)..(42)
<223> OTHER INFORMATION: Leu or Phe
<220> FEATURE:
<221> NAME/KEY: MOD_RES
<222> LOCATION: (43)..(44)
<223> OTHER INFORMATION: May or may not be present
<220> FEATURE:
<221> NAME/KEY: MOD_RES
<222> LOCATION: (45)..(45)
<223> OTHER INFORMATION: Leu or Lys
<220> FEATURE:
<221> NAME/KEY: MOD_RES
<222> LOCATION: (46)..(46)
<223> OTHER INFORMATION: Pro or Gln
<220> FEATURE:
<221> NAME/KEY: MOD_RES
<222> LOCATION: (47)..(47)
<223> OTHER INFORMATION: Ala, Asp or Gly
<220> FEATURE:
<221> NAME/KEY: MOD_RES
```

```
<222> LOCATION: (48)..(48)
<223> OTHER INFORMATION: Leu, Val or Pro
<220> FEATURE:
<221> NAME/KEY: MOD_RES
<222> LOCATION: (49)..(49)
<223> OTHER INFORMATION: Leu or Arg
<220> FEATURE:
<221> NAME/KEY: MOD_RES
<222> LOCATION: (50)..(50)
<223> OTHER INFORMATION: Gln or Asn
<220> FEATURE:
<221> NAME/KEY: MOD_RES
<222> LOCATION: (51)..(51)
<223> OTHER INFORMATION: Gln, Leu or Thr
<220> FEATURE:
<221> NAME/KEY: MOD_RES
<222> LOCATION: (53)..(53)
<223> OTHER INFORMATION: Gly or Trp
<220> FEATURE:
<221> NAME/KEY: MOD_RES
<222> LOCATION: (54)..(54)
<223> OTHER INFORMATION: Gln or Thr
<220> FEATURE:
<221> NAME/KEY: MOD_RES
<222> LOCATION: (55)..(55)
<223> OTHER INFORMATION: Glu or Ser
<220> FEATURE:
<221> NAME/KEY: MOD_RES
<222> LOCATION: (56)..(56)
<223> OTHER INFORMATION: Asn, Cys or Leu
<220> FEATURE:
<221> NAME/KEY: MOD_RES
<222> LOCATION: (58)..(58)
<223> OTHER INFORMATION: Gln, Ile or Ala
<220> FEATURE:
<221> NAME/KEY: MOD_RES
<222> LOCATION: (59)..(63)
<223> OTHER INFORMATION: May or may not be present
<220> FEATURE:
<221> NAME/KEY: MOD_RES
<222> LOCATION: (65)..(65)
<223> OTHER INFORMATION: Leu or Pro
<220> FEATURE:
<221> NAME/KEY: MOD_RES
<222> LOCATION: (66)..(66)
<223> OTHER INFORMATION: Gln or Glu
<220> FEATURE:
<221> NAME/KEY: MOD_RES
<222> LOCATION: (67)..(67)
<223> OTHER INFORMATION: Gln, Lys or Ser
<220> FEATURE:
<221> NAME/KEY: MOD_RES
<222> LOCATION: (68)..(68)
<223> OTHER INFORMATION: Ile, Ala or Leu
<220> FEATURE:
<221> NAME/KEY: MOD_RES
<222> LOCATION: (69)..(69)
<223> OTHER INFORMATION: Ser or Thr
<220> FEATURE:
<221> NAME/KEY: MOD_RES
<222> LOCATION: (70)..(70)
<223> OTHER INFORMATION: Arg, Pro or not present
<220> FEATURE:
<221> NAME/KEY: MOD_RES
<222> LOCATION: (71)..(71)
<223> OTHER INFORMATION: His or Pro
<220> FEATURE:
<221> NAME/KEY: MOD_RES
<222> LOCATION: (74)..(74)
<223> OTHER INFORMATION: Gln or Arg
<220> FEATURE:
<221> NAME/KEY: MOD_RES
<222> LOCATION: (75)..(75)
<223> OTHER INFORMATION: Phe, Leu or Arg
<220> FEATURE:
<221> NAME/KEY: MOD_RES
<222> LOCATION: (76)..(76)
<223> OTHER INFORMATION: Ile, Glu or Met
<220> FEATURE:
```

```
<221> NAME/KEY: MOD_RES
<222> LOCATION: (78)..(78)
<223> OTHER INFORMATION: May or may not be present
<220> FEATURE:
<221> NAME/KEY: MOD_RES
<222> LOCATION: (79)..(79)
<223> OTHER INFORMATION: Met, Val or Ser
<220> FEATURE:
<221> NAME/KEY: MOD_RES
<222> LOCATION: (81)..(81)
<223> OTHER INFORMATION: Asn or Phe
<220> FEATURE:
<221> NAME/KEY: MOD_RES
<222> LOCATION: (82)..(82)
<223> OTHER INFORMATION: May or may not be present
<220> FEATURE:
<221> NAME/KEY: MOD_RES
<222> LOCATION: (83)..(84)
<223> OTHER INFORMATION: Pro, Val or not present
<220> FEATURE:
<221> NAME/KEY: MOD_RES
<222> LOCATION: (85)..(85)
<223> OTHER INFORMATION: Gly, Thr or not present
<220> FEATURE:
<221> NAME/KEY: MOD_RES
<222> LOCATION: (86)..(86)
<223> OTHER INFORMATION: Glu, Ser or not present

<400> SEQUENCE: 17

Glu Xaa Pro Xaa Xaa Xaa Xaa Pro Xaa Xaa Gln Xaa Xaa Xaa Xaa Ala
1               5                   10                  15

Xaa Xaa Xaa Glu Glu Leu Trp Gly Val Gly Glu Asp Gly Gly Pro Ser
            20                  25                  30

Pro Ala Asn Pro Gly Xaa Xaa Pro Xaa Xaa Ser Arg Xaa Xaa Xaa Xaa
            35                  40                  45

Xaa Xaa Xaa Leu Xaa Xaa Xaa Xaa Pro Xaa Val Arg Gly Ser Gly Leu
    50                  55                  60

Xaa Xaa Xaa Xaa Xaa Xaa Xaa Gln Glu Xaa Xaa Xaa Gln Glu Xaa Leu
65                  70                  75                  80

Xaa Xaa Xaa Xaa Xaa Xaa
                85

<210> SEQ ID NO 18
<211> LENGTH: 407
<212> TYPE: PRT
<213> ORGANISM: Mus sp.

<400> SEQUENCE: 18

Pro Thr Leu Lys Pro Pro Arg Ile Ile Arg Pro Arg Pro Ser Arg
1               5                   10                  15

His Arg Ala Pro His Ser Pro Gly Pro Leu His Asn Gly Ser Ser Pro
            20                  25                  30

Lys Ala Leu Pro Gln Ile Ser Asn Asp Ala Ser Ala Ser Val Cys Thr
            35                  40                  45

Ser Ile Phe Trp Glu Pro Pro Thr Ala Ser Leu Lys Pro Pro Ala Leu
    50                  55                  60

Leu Pro Pro Ser Val Ser Arg Thr Ser Leu Asp Ser Gln Thr Ser Pro
65                  70                  75                  80

Asp Ser Pro Ser Ser Thr Pro Ser Pro Ser Pro Val Ser Arg Arg Ser
                85                  90                  95

Ile Ser Pro Glu Pro Ala Pro Cys Ser Pro Val Pro Pro Lys Pro
            100                 105                 110

Ser Gly Ser Ser Arg Thr Pro Leu Pro Ser Gly Pro Thr Pro Leu Gln
            115                 120                 125
```

```
Asp Gly Ser Ala Ser Ala Pro Gly Thr Val Arg Arg Leu Ala Gly Lys
            130                 135                 140
Phe Glu Trp Gly Ala Glu Gly Lys Ala Gln Ser Ser Asp Ser Leu Glu
145                 150                 155                 160
Arg Cys Ser Gln Gly Ser Thr Glu Val Asn Gly Glu Lys Glu Thr Pro
                165                 170                 175
Glu Ala Ala Leu Ser Gly Asn Gly Ser Gln Glu Asn Gly Thr Pro Asp
            180                 185                 190
Ala Ala Leu Ala Cys Pro Pro Cys Pro Cys Pro Val Cys His Val Ala
        195                 200                 205
Lys Pro Gly Leu Glu Leu Arg Trp Val Pro Val Gly Ser Ser Glu Asp
210                 215                 220
Ile Leu Arg Ile Pro Cys Arg Ala Ser Pro Leu Arg Ala Ser Arg Ser
225                 230                 235                 240
Arg Ile Asn Pro Pro Val Ile Ser His Pro Pro Val Val Leu Thr Ser
                245                 250                 255
Tyr Arg Ser Thr Ala Glu Arg Lys Leu Leu Pro Pro Leu Lys Pro Pro
            260                 265                 270
Lys Pro Thr Lys Val Arg Gln Asp Ile Ser Thr Ser Glu Glu Leu Pro
        275                 280                 285
Gln Pro Asp Leu Lys Leu Pro Ser Glu Asp Gly Ile Gln Thr Ala Thr
290                 295                 300
Lys Ala Trp Glu Gly Asp Arg Pro Glu Gly Ala Pro Leu Asn Ala Pro
305                 310                 315                 320
Pro Val Ala Leu Glu Gly Arg Glu Glu Gly Leu Asp Gly Leu Lys
                325                 330                 335
Gly Leu Gln Trp Glu Leu Pro Leu Gln Asp Glu Pro Leu Tyr Gln Thr
            340                 345                 350
Tyr Arg Ala Ala Val Leu Ser Glu Glu Leu Trp Gly Val Gly Glu Asp
        355                 360                 365
Gly Gly Pro Ser Pro Ala Asn Pro Gly Glu Ala Pro Thr Phe Ser Arg
370                 375                 380
Leu Pro Gly Pro Arg Asn Thr Leu Trp Gln Glu Leu Pro Ala Val Arg
385                 390                 395                 400
Gly Ser Gly Leu Leu Glu Ser
                405

<210> SEQ ID NO 19
<211> LENGTH: 13
<212> TYPE: PRT
<213> ORGANISM: Mus sp.

<400> SEQUENCE: 19

Glu His Glu Arg Arg Lys His Leu Arg Gln His Gln Lys
1               5                   10

<210> SEQ ID NO 20
<211> LENGTH: 15
<212> TYPE: PRT
<213> ORGANISM: Mus sp.
<220> FEATURE:
<221> NAME/KEY: MOD_RES
<222> LOCATION: (8)..(8)
<223> OTHER INFORMATION: Phospho-Tyr

<400> SEQUENCE: 20

Pro Leu Gln Asp Glu Pro Leu Tyr Gln Thr Tyr Arg Ala Ala Val
```